United States Patent
Osaki et al.

(10) Patent No.: US 12,280,153 B2
(45) Date of Patent: *Apr. 22, 2025

(54) ENTERIC HARD CAPSULE

(71) Applicant: QUALICAPS CO., LTD., Nara (JP)

(72) Inventors: Yoshiro Osaki, Nara (JP); Makoto Aso, Nara (JP); Koki Ueno, Nara (JP)

(73) Assignee: QUALICAPS CO., LTD., Nara (JP)

( * ) Notice: Subject to any disclaimer, the term of this patent is extended or adjusted under 35 U.S.C. 154(b) by 473 days.

This patent is subject to a terminal disclaimer.

(21) Appl. No.: 17/254,449

(22) PCT Filed: Jun. 21, 2019

(86) PCT No.: PCT/JP2019/024713
§ 371 (c)(1),
(2) Date: Dec. 21, 2020

(87) PCT Pub. No.: WO2019/245031
PCT Pub. Date: Dec. 26, 2019

(65) Prior Publication Data
US 2021/0228491 A1    Jul. 29, 2021

(30) Foreign Application Priority Data

Jun. 22, 2018 (JP) ................... 2018-118980
Jan. 11, 2019 (JP) ................... 2019-003117

(51) Int. Cl.
*A61K 9/48* (2006.01)
*A61K 47/32* (2006.01)
*A61K 47/38* (2006.01)

(52) U.S. Cl.
CPC ............ *A61K 9/4816* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | |
|---|---|---|
| 630,966 A | 8/1899 | Bohm et al. |
| 2,196,768 A | 4/1940 | Hiatt et al. |
| 2,718,667 A | 9/1955 | Malm et al. |
| 3,826,666 A | 7/1974 | Hiai et al. |
| 3,853,594 A | 12/1974 | Moroff et al. |
| 3,927,195 A | 12/1975 | Messora |
| 4,138,013 A | 2/1979 | Okajima |
| 4,365,060 A | 12/1982 | Onda et al. |
| 4,644,031 A | 2/1987 | Lehmann et al. |
| 5,644,011 A | 7/1997 | Lehmann et al. |
| 5,756,123 A | 5/1998 | Yamamoto et al. |
| 6,309,666 B1 | 10/2001 | Hatano et al. |
| 7,094,425 B2 | 8/2006 | Scott et al. |
| 9,107,451 B2 | 8/2015 | Skalsky et al. |
| 2003/0104047 A1 | 6/2003 | Chen et al. |
| 2005/0079216 A1 | 4/2005 | Petereit et al. |
| 2005/0152977 A1 | 7/2005 | Petereit et al. |
| 2006/0177496 A1 | 8/2006 | McAllister et al. |
| 2010/0074947 A1 | 3/2010 | Brown et al. |
| 2012/0161364 A1 | 6/2012 | Son et al. |
| 2013/0203868 A1 | 8/2013 | Son et al. |
| 2017/0119681 A1 | 5/2017 | Bravo Gonzalez et al. |
| 2020/0375910 A1 | 12/2020 | Osaki et al. |

FOREIGN PATENT DOCUMENTS

| | | |
|---|---|---|
| CA | 2 769 046 | 2/2011 |
| CN | 102119026 | 7/2011 |
| CN | 102198114 | 9/2011 |

(Continued)

OTHER PUBLICATIONS

Li et al. (The use of hypromellose in oral drug delivery, Journal of Pharmacy and Pharmacology, Jan. 21, 2005). (Year: 2005).*
Office Action dated Jul. 14, 2021 in Indian Application No. 202047005393.
Li et al. "The use of hypromellose in oral drug delivery", Journal of Pharmacy and Pharmacology, 2005, vol. 57, pp. 533-546.
Ashland, Product Grades Available, 2016, 4 pages.
Microcarrier drug delivery system, 2009, p. 408, with English translation.
International Search Report dated Sep. 17, 2019 in International (PCT) Application No. PCT/JP2019/024713.

(Continued)

*Primary Examiner* — Melissa S Mercier
(74) *Attorney, Agent, or Firm* — Wenderoth, Lind & Ponack, L.L.P.

(57) ABSTRACT

To provide a hard capsule composed of a hard capsule film that can be molded by a cold gelation method and has enteric properties. The problem is solved by an enteric hard capsule comprising a film (a) containing a first component and a second component, or (b) containing a first component and a second component, and further containing at least one component selected from a third component and a fourth component, wherein the first component is methylcellulose and/or hydroxypropyl methylcellulose having a viscosity value of 6 mPa·s or more, the second component is an enteric methacrylic acid copolymer, the third component is a water-insoluble alkyl (meth)acrylate ester copolymer and/or ethyl cellulose, and the fourth component is at least one selected from the group consisting of a plasticizer and a surfactant acceptable pharmaceutically or as a food additive, and wherein the first component is contained at a rate of 30 to 70% by mass and the second component is contained at a rate of 30 to 60% by mass with the sum of the rates of the first component and the second component being 70% by mass or more based on the total mass of the first component, the second component, the third component and the fourth component contained in the film, which is taken as 100% by mass.

26 Claims, 8 Drawing Sheets

(56) References Cited

FOREIGN PATENT DOCUMENTS

| | | |
|---|---|---|
| CN | 106456559 | 2/2017 |
| DE | 2135073 | 2/1973 |
| DE | 2157435 | 6/1973 |
| EP | 2 283 830 | 2/2011 |
| EP | 3332775 | 6/2018 |
| GB | 2 087 235 | 5/1982 |
| JP | 47-003547 | 2/1972 |
| JP | 53-052619 | 5/1978 |
| JP | 55-136061 | 10/1980 |
| JP | 57-032230 | 2/1982 |
| JP | 57-109716 | 7/1982 |
| JP | 60-190725 | 9/1985 |
| JP | 62-10023 | 1/1987 |
| JP | 8-81392 | 3/1996 |
| JP | 8-208458 | 8/1996 |
| JP | 2001-506692 | 5/2001 |
| JP | 2003-325642 | 11/2003 |
| JP | 2004-522746 | 7/2004 |
| JP | 2005194218 * | 7/2005 |
| JP | 2005-526546 | 9/2005 |
| JP | 2006-016372 | 1/2006 |
| JP | 2006-052819 | 2/2006 |
| JP | 2006-528197 | 12/2006 |
| JP | 2007-500176 | 1/2007 |
| JP | 2009-507875 | 2/2009 |
| JP | 2009-196961 | 9/2009 |
| JP | 2009-532331 | 9/2009 |
| JP | 2009-538315 | 11/2009 |
| JP | 2010-202550 | 9/2010 |
| JP | 2010-270039 | 12/2010 |
| JP | 2011-500871 | 1/2011 |
| JP | 2011-503048 | 1/2011 |
| JP | 2013-500293 | 1/2013 |
| JP | 2013-504565 | 2/2013 |
| JP | 2013-540149 | 10/2013 |
| JP | 2013-540806 | 11/2013 |
| JP | 2015-515962 | 6/2015 |
| JP | 2015-518005 | 6/2015 |
| WO | 98/27151 | 6/1998 |
| WO | 02/060384 | 8/2002 |
| WO | 02/060385 | 8/2002 |
| WO | 2004/010978 | 2/2004 |
| WO | 2005/011647 | 2/2005 |
| WO | 2007/031326 | 3/2007 |
| WO | 2007/103200 | 9/2007 |
| WO | 2007/139886 | 12/2007 |
| WO | 2008/050209 | 5/2008 |
| WO | 2009/087483 | 7/2009 |
| WO | 2011/012369 | 2/2011 |
| WO | 2011/036601 | 3/2011 |
| WO | 2012/053703 | 4/2012 |
| WO | 2012/056321 | 5/2012 |
| WO | 2013/164121 | 11/2013 |
| WO | 2013/164122 | 11/2013 |
| WO | WO-2013164122 A1 * 11/2013 ............. A61K 47/10 |  |
| WO | 2017/022248 | 2/2017 |
| WO | 2019/013260 | 1/2019 |

OTHER PUBLICATIONS

Moghimipour et al., "In vivo evaluation of pH and time-dependent polymers as coating agent for colonic delivery using central composite design", Journal of Drug Delivery Science and Technology, 2017, vol. 43, pp. 50-56.

Zhang et al., "Formulation and preparation of rabeprazole sodium enteric-coated capsules", Central South Pharmacy, 2016, vol. 14, No. 7, pp. 712-716, with English Abstract.

Ranip et al., "Development and In-Vitro Drug Release Studies of Satranidazole Capsules for Colon Specific Drug Delivery", Asian Journal of Pharmaceutical and Clinical Research, 2014, Vo. 7, Issue 3, pp. 203-211.

Felton et al., "Mechanical Properties of Polymeric Films Prepared from Aqueous Dispersions", Aqueous Polymeric Coatings for Pharmaceutical Dosage Forms, 4th edition, CRC Press, 2017, Chapter 4, Chapter 9, Chapter 10 (Table 10.5).

Cole et al., "Enteric coated HPMC capsules designed to achieve intestinal targeting", International Journal of Pharmaceutics, 2002, vol. 231, pp. 83-95.

Dvorackova et al., "Coated hard capsules as the pH-dependent drug transport systems to ileo-colonic compartment", Drug Development and Industrial Pharmacy, 2011, vol. 37, No. 10, pp. 1131-1140.

Zema et al., "Gastroresistant capsular device prepared by injection molding", International Journal of Pharmaceutics, 2013, vol. 440, pp. 264-272.

Hibino et al., "Development of Formulation Considering the Intake Easiness", 2008 Mie Prefectural Industrial Research Institute Research Report, No. 33, 2009, pp. 59-64, with Partial English-language translation.

Brogmann et al., "Enteric Targeting Through Enteric Coating", Drug Targeting Technology, CRC press, 2001, Part 1, pp. 1-29.

Nigam et al., "Effect of Wheat ARF Treatment on the Baking Quality of Whole Wheat Flours of the Selected Varieties of Wheat", Journal of Applied Pharmaceutical Science, 2013, vol. 3, pp. 139-145.

Sharma et al., "Solid-State Interactions at the Core-Coat Interface: Physicochemical Characterization of Enteric-Coated Omeprazole Pellets Without a Protective Sub-Coat", AAPS PharmSciTech, 2015, vol. 16, No. 4, pp. 934-943.

"Formulation Study of Lanzoprazole Fast-disintegrating Tablets Containing Enteric-coated Microgranules", J. Soc. Powder Technol., Japan, 2005, vol. 42, p. 811, with English-language translation.

Tagawa et al., "Adsorption Treatment of Polymer at Lower Critical Solution Temperature (LCST) and its Effect on the Stability of Polystyrene Latices", Japanese Journal of Polymer Science and Technology, 1983, vol. 40, pp. 273-278, with English Abstract.

Wong et al., "Flocculation of an Aqueous Colloidal Ethyl Cellulose Dispersion (Aquacoat) with a Water-Soluble Polymer, Hydroxypropyl Methylcellulose", Eur. J. Pharm. Biopharm., 1996, vol. 42, pp. 12-15.

Ohyagi et al., "Synergetic Role of Hypromellose and Methacrylic Acid Copolymer in the Dissolution Improvement of Amorphous Solid Dispersions", Journal of Pharmaceutical Science, 2017, vol. 106, pp. 1042-1050.

Ronbunshu et al., "Temperature-Viscosity Relationships of Aqueous Solutions of Cellulose Ethers", Mar. 1981, vol. 38, No. 3, pp. 133-137, with English abstract.

Klug et al., "Some Properties of Water-Soluble Hydroxyalkyl Cellulose and Their Derivatives", J. Polymer Sci: Part C, 1971, No. 36, pp. 491-508.

Extended European Search Report dated May 26, 2020 in European Application No. 18832265.5.

International Search Report dated Sep. 4, 2018 in International (PCT) Application No. PCT/JP2018/026216.

Extended European Search Report dated Jun. 3, 2022 in corresponding European Patent Application No. 19822248.1.

"Formulation Study of Lanzoprazole Fast-disintegrating Tablets Containing Enteric-coated Microgranules", J. Soc. Powder Technol., Japan, 2005, vol. 42, pp. 811, with English-language translation.

Office Action issued Feb. 29, 2024, for corresponding Chinese Patent Application No. 201980053922.X, with English translation.

* cited by examiner

ENTERIC HARD CAPSULE

TECHNICAL FIELD

The present invention relates to an enteric hard capsule, an enteric hard capsule preparation liquid, a method for preparing an enteric hard capsule preparation liquid, and a method for preparing an enteric hard capsule.

BACKGROUND ART

The term "enteric" generally means a characteristic of a dosage form of formulations that are administered orally and hardly dissolve in the stomach. Also, the formulation has a characteristic of being easily dissolved after being transferred into the intestine. An enteric formulation does not release a drug active component in the stomach, which has a strong acidic environment, and releases a drug active component after the formulation is moved into the intestine. For this reason, an enteric formulation is mainly used for the purpose of protecting a drug active component from the gastric acid or gastric enzymes, or for the purpose of continuously releasing a drug active component utilizing the time during which the formulation is moved from the stomach to the small intestine.

In the field of pharmaceutical formulations, "enteric" is defined in almost the same way in Japan (Japanese Pharmacopoeia 17th Edition, 6.10 Dissolution Test, 4.3 Enteric Preparation), the United States (US Pharmacopeia Monograph <711> Dissolution 7, Delayed-Release Dosage Forms), and Europe (European Pharmacopeia, 2.9.3, Delayed-release dosage forms). In particular, Japan, Europe and the United States agree in that the formulations are required to have such a level of acid resistance that they are not substantially dissolved for two hours at 37° C. in an acidic environment (pH about 1.2, diluted hydrochloric acid solution). On the other hand, there is no particular regulation regarding the temporal dissolution characteristics in the intestine. The dissolution characteristics required vary depending, for example, on whether the release target site is the small intestine, colon or large intestine and whether the drug release characteristics are immediate-release or sustained-release.

When the formulation dosage form is a tablet, an "enteric" formulation that satisfies the above requirements is prepared by coating a tablet with a so-called enteric polymer (Non-Patent Document 1, Chapters 9 and 10).

Also, when the formulation dosage form is a hard capsule, preparing an enteric hard capsule formulation by a method in which a coating of an enteric polymer similar to that for a tablet is applied to a non-enteric hard capsule filled with a content (coating method), and, in some cases, a method in which an enteric coating is applied by a dipping method to an empty non-enteric capsule before removal from an dipping pin have been conventionally employed (Patent Documents 1 to 6, Non-Patent Documents 2 and 3).

In addition, an attempt has been made to make a hard capsule film itself enteric. Such related arts include the following:

(1) A gelling agent capable of imparting acid resistance, such as gellan gum, is used instead of or in conjunction with an acid-resistant enteric polymer to maintain acid resistance as well as to improve gelation properties and film performance (Patent Documents 7 to 10);
(2) A solvent-based dipping solution is used instead of a water-based solution (Patent Document 11);
(3) A poorly water-soluble acid-resistant enteric polymer is used as a primary component and a conventional polymer that is water-soluble and has a high film-forming ability, such as gelatin or water-soluble cellulose, is partially used (Patent Documents 12, 13);
(4) In order to obtain a water-soluble derivative containing a poorly water-soluble enteric polymer, almost all acid groups (in particular, carboxyl groups) of an enteric polymer are salified, or a non-salified polymer is at least partially neutralized with a basic neutralizing agent to dissolve it in water, or a non-salified emulsion dispersion is utilized (Patent Documents 12 to 20, 26 to 28); and,
(5) An alternative technique that does not require solubilization of a polymer, such as injection molding, is used (Patent Documents 21 to 25, Non-Patent Document 4).

CONVENTIONAL ART DOCUMENT

Patent Literature

[Patent Document 1] U.S. Pat. No. 2,196,768
[Patent Document 2] U.S. Pat. No. 6,309,666
[Patent Document 3] U.S. Pat. No. 7,094,425
[Patent Document 4] U.S. Pat. No. 3,927,195
[Patent Document 5] Japanese Unexamined Patent Application No. 2003-325642
[Patent Document 6] Japanese Translation of PCT International Application Publication No. 2013-500293
[Patent Document 7] Japanese Unexamined Patent Application No. 2006-16372
[Patent Document 8] Japanese Unexamined Patent Application No. 2010-202550
[Patent Document 9] Japanese Unexamined Patent Application No. 2009-196961
[Patent Document 10] WO2011/036601
[Patent Document 11] U.S. Pat. No. 4,365,060
[Patent Document 12] U.S. Pat. No. 3,826,666
[Patent Document 13] U.S. Pat. No. 4,138,013
[Patent Document 14] U.S. Pat. No. 2,718,667
[Patent Document 15] Japanese Unexamined Patent Application No. 2013-504565
[Patent Document 16] Japanese Translation of PCT International Application Publication No. 2013-540149
[Patent Document 17] Japanese Translation of PCT International Application Publication No. 2015-518005
[Patent Document 18] Japanese Translation of PCT International Application Publication No. 2013-540806
[Patent Document 19] Japanese Translation of PCT International Application Publication No. 2015-515962
[Patent Document 20] Japanese Unexamined Patent Application No. Sho 55-136061
[Patent Document 21] Japanese Unexamined Patent Application No. Sho 47-3547
[Patent Document 22] Japanese Unexamined Patent Application No. Sho 53-52619
[Patent Document 23] Japanese Translation of PCT International Application Publication No. 2006-52819
[Patent Document 24] Japanese Translation of PCT International Application Publication No. 2011-503048
[Patent Document 25] Japanese Translation of PCT International Application Publication No. 2004-522746
[Patent Document 26] German Patent No. 2157435
[Patent Document 27] Japanese Unexamined Patent Application No. Sho 62-010023

[Patent Document 28] Japanese Unexamined Patent Application No. Sho 60-190725

[Patent Document 29] Japanese Unexamined Patent Application No. Sho 57-109716

Non-Patent Document

[Non-Patent Document 1] Aqueous Polymeric Coating For Pharmaceutical Dosage Forms, 4th edition, CRC Press, 2017, Chapter 4, Chapter 9, Chapter 10 (Table 10.5)

[Non-Patent Document 2] International Journal of Pharmaceutics; 231 (2002), p. 83-95

[Non-Patent Document 3] Drug Dev. Ind. Pharm.; 27(2011) p. 1131-1140

[Non-Patent Document 4] International Journal of Pharmaceutics; 440 (2013), p. 264-272

[Non-Patent Document 5] Reports of the Mie Prefecture Industrial Research Institute No. 33 (2009), p. 59-64

[Non-Patent Document 6] Drug Targeting Technology, CRC press, 2001, Part I-1, pp. 1-29

[Non-Patent Document 7] Journal of Applied Pharmaceutical Science 3 (2013), pp. 139-144

[Non-Patent Document 8] AAPS Pharam Scie Tech, 16(2015), pp. 934-943

[Non-Patent Document 9] J. Soc. Powder Technol., Japan, 42(2005), pp. 811

[Non-Patent Document 10] Japanese Journal of Polymer Science and Technology 40(1983), pp. 273-278

[Non-Patent Document 11] Eur. J. Pharm. Biopharm. 42(1996), pp. 12-15

[Non-Patent Document 12] Journal of Pharmaceutical Sciences, 106(2017), pp. 1042-1050.

SUMMARY OF INVENTION

Technical Problem

However, in general, preparation of an enteric hard capsule formulation by a coating method is a complicated preparation process that requires filling a content, fitting the cap and body together and sealing the fitted portions before the surface coating. Also, the burden of operation resulting from the complicated preparation process is placed not on the manufacturer of the hard capsules but on the manufacturer that fills the content. This impairs the convenience of hard capsules as a formulation form. When an empty capsule is coated in advance, the capsule production process itself is complicated because both the capsule film and the coating film require a separate drying time or an undercoat must be applied to increase the adhesion between the capsule film and the coating film.

Because of these reasons, it is desired that the hard capsule film itself is enteric.

A hard capsule is usually prepared by a dipping (soaking) method. Specifically, in a dipping method, a capsule film polymer material is dissolved to prepare an aqueous solution, and a molding pin (in general, a molding pin made of stainless steel) is dipped into the aqueous polymer solution. Then, the molding pin is pulled up from the dipping liquid and inverted, and the aqueous polymer solution adhering to a surface of the molding pin is dried to form a film with a thickness of about 100 μm. Then, the dried capsule film is removed from the molding pin, cut to a desired length before the content is filled and the cap and the body are fitted together. Then, printing is performed on a surface of the hard capsule, and the hard capsule is packaged.

Also, in a dipping method, in order to obtain an aqueous preparation liquid for dipping, it is desired that the polymer as a primary component of the hard capsule film is water-soluble, or is in the form of a fluid dispersion in which very fine colloids or solid fine particles are dispersed. Also, it is desired that the polymer has a property of gelating to exhibit an abrupt increase in viscosity with an abrupt increase or decrease in temperature when the molding pin dipped into the preparation liquid is pulled up, in other words, a hot or cold gelation ability. In addition, it is required that the aqueous preparation liquid for dipping can prevent liquid dripping that may occur immediately after the molding pin is pulled up and can be finally molded into a film having sufficient hardness and toughness as a hard capsule through subsequent dry solidification by evaporation of moisture.

However, general enteric polymers (also referred to as "enteric bases") for coating do not have physical properties suitable for preparation of a hard capsule by a dipping method. Enteric polymers that are commercially available for coating of tablets, or films formed from a coating fluid containing such an enteric polymer can function as a film on a tablet, that is, a surface of a solid, but do not necessarily have sufficient film forming properties and strength to be self-supporting as a single film. Thus, it is difficult to form a film from an enteric polymer alone and, even if a self-supporting film can be formed, the film has a problem with strength and cannot be utilized on its own as a hard capsule.

Also, the related arts have the following problems.

In the above-mentioned related art (I), the hard capsule film has improved moldability but has insufficient acid resistance. In addition, when a gelling agent is used to gelate the polymer, in particular, in a cold gelation method that requires cations as a gelation aid, there is a problem in that the stability of the aqueous polymer solution or fluid dispersion and the cold gelation performance of the gelling agent are impaired due to the pH of the aqueous solution containing the polymer or the interaction between the cations and ionic groups of the enteric polymer.

Next, in the above-mentioned related art (2), it is required to take measures against working environment contamination and fire and explosion caused by an organic solvent or the like that volatilizes during the preparation process, and to recover waste solvent. In addition, there is a problem in that the solvent may remain in the final product.

In the above-mentioned related art (3), when gelatin is used as a water-soluble polymer or a cold gelling agent, turbidity often occurs in the capsule film because of its insufficient compatibility with the acid-resistant enteric polymer.

Next, in the above-mentioned related art (4), in order to obtain an aqueous preparation liquid for dipping, the acid groups of the enteric polymer are salified or the enteric polymer is neutralized (or salified) almost completely. However, these treatments impart undesirable water sensitivity to the molded hard capsule film itself. There is a problem in that the stability of the aqueous polymer solution or fluid dispersion and the cold gelation performance of the gelling agent are impaired due to the pH of the aqueous solution containing the polymer or the interaction between the cations and the ionic groups of the enteric polymer. Also, because an excess amount of a neutralizing agent (for example, alkaline agent) is contained, when the hard capsule composed primarily of the enteric polymer subjected to the treatment is stored under a severe high temperature condition, salt precipitation, that is, gradual escape of the neutralizing agent component from the capsule, may occur and cause the hard capsule to turn yellow in appearance. In particular, the influence is significant when ammonia is used for neutralization. In addition, because ammonia volatilizes during the capsule production process, in particular in the drying step, measures must be taken against exposure thereto during the operation.

In particular, when an enteric cellulose compound alone is used as an enteric base, even when used not in a completely neutralized and dissolved state but as a partially neutralized fine fluid dispersion, it is necessary to neutralize a majority of carboxyl groups in order to sufficiently reduce the particle size of the enteric cellulose compound. Then, there occurs a problem in that the concentration of residual salt in the film may be as high as 1 to 10% by mass. In addition, when an enteric cellulose compound is used as an enteric polymer, its hot gelation property is often utilized and a preparation liquid for dipping suitable for molding by a cold gelation method is not known.

An acidic (meth)acrylic acid copolymer containing carboxyl groups and a neutral alkyl (meth)acrylate ester copolymer form an aqueous dispersion (emulsion) containing colloidal particles with a diameter of several tens nm in each emulsion polymerization process. Although capsule formation by a dipping method using a colloid-mixed fluid dispersion of such a (meth)acrylic acid copolymer and a neutral alkyl (meth)acrylate ester copolymer has been also proposed, mechanical strength as a hard capsule is not necessarily sufficient even when a capsule shape can be achieved. Also, because the fluid dispersion itself has no cold gelation ability and is therefore solidified simply by drying, it drips significantly and is not suitable for mass production of hard capsules by a dipping method.

Next, in the above-mentioned related art (5), a general production apparatus for a dipping method cannot be used in the first place. In addition, because thermoplasticity of a polymer is utilized to mold a capsule in injection molding, there is a concern of thermal denaturation of the polymer itself caused by a heat treatment at about 100° C. in the molding process. Polymers that can be used to maintain thermoplasticity are limited. In particular, hydroxypropyl cellulose is preferred among cellulose compounds because of its good processability, but tends to have insufficient hardness as a capsule film. In addition, in injection molding, because excessive stress caused by thermal contraction is applied to the film when the film is cooled to room temperature after the shape of a capsule is molded under heating and because the capsule after molding contains almost no moisture, there is a concern of cracking in the capsule after molding.

Also, films of currently generally available hard capsules have a thickness of about 100 μm, and the capsules are filled with a content by a capsule filling machine. On the other hand, in injection molding, it is necessary to take measures such as mixing a plasticizer in the film in such an amount that the acid resistance is sacrificed to prevent cracking or forming a thick film with a thickness of about several hundred μm to keep mechanical strength. Thus, there may occur a problem of interaction between a large amount of additives and the contained drug. Also, because there is no choice but to make the film of a hard capsule molded by injection molding thicker than those of currently available hard capsules, it is difficult to prepare an enteric hard capsule that maintains compatibility with commonly used capsule filling machines.

It is, therefore, an object of the present invention to provide an enteric capsule that can be molded by a cold gelation method. Another object of the present invention is to provide an enteric hard capsule having compatibility with commonly used non-enteric hard capsules in terms of workability in filling operation, for example.

Solution to Problem

The present inventors conducted intensive studies, and found that an enteric hard capsule as described below has good enteric properties and good mechanical strength as a hard capsule. The present inventors also found that an enteric hard capsule preparation liquid containing the following components can be prepared into a hard capsule by a cold gelation method.

The present invention can include the following embodiments.

Embodiment 1. An enteric hard capsule comprising a film
(a) containing a first component and a second component, or
(b) containing a first component and a second component, and further containing at least one component selected from a third component and a fourth component,
in which the first component is methylcellulose and/or hydroxypropyl methylcellulose having a viscosity value of 6 mPa·s or more,
the second component is an enteric methacrylic acid copolymer,
the third component is a water-insoluble alkyl (meth)acrylate ester copolymer and/or ethyl cellulose, and
the fourth component is at least one selected from the group consisting of a plasticizer and a surfactant acceptable pharmaceutically or as a food additive, and
in which the first component is contained at a rate of 30 to 70% by mass and the second component is contained at a rate of 30 to 60% by mass with the sum of the rates of the first component and the second component being 70% by mass or more based on the total mass of the first component, the second component, the third component and the fourth component contained in the film, which is taken as 100% by mass.

Embodiment 2. The enteric hard capsule according to Embodiment 1, in which the first component has a viscosity value of 10 mPa·s or more.

Embodiment 3. The enteric hard capsule according to Embodiment 1 or 2, in which the first component is hydroxypropyl methylcellulose of substitution degree type 2910 or substitution degree type 2906.

Embodiment 4. The enteric hard capsule according to any one of Embodiments 1 to 3, in which the enteric methacrylic acid copolymer of the second component is a copolymer composed of 40 to 60% by mass of methacrylic acid and 60 to 40% by mass of ethyl acrylate.

Embodiment 5. The enteric hard capsule according to any one of Embodiments 1 to 4, in which the film has a moisture content of 2 to 10% by mass.

Embodiment 6. The enteric hard capsule according to any one of Embodiments 1 to 5, in which the third component is contained at a rate of 0 to 30% by mass based on the total mass of the first component, the second component, the third component and the fourth component contained in the film, which is taken as 100% by mass.

Embodiment 7. The enteric hard capsule according to any one of Embodiments 1 to 6, in which the fourth component is contained at a rate of 0 to 12% by mass based on the total mass of the first component, the second component, the third component and the fourth component contained in the film, which is taken as 100% by mass.

Embodiment 8. The enteric hard capsule according to any one of Embodiments 1 to 7, in which at least some of carboxyl groups contained in the second component form a salt thereof that is acceptable pharmaceutically or as a food additive.

Embodiment 9. The enteric hard capsule according to Embodiment 8, in which the carboxyl groups forming a salt is contained at a rate of 2 to 20 mol % based on the total number of moles of the carboxyl groups forming a salt and carboxyl groups not forming a salt in the second component contained in the film, which is taken as 100 mol %.

Embodiment 10. The enteric hard capsule according to any one of Embodiments 8 or 9, in which the salt is a sodium salt.

Embodiment 11. The enteric hard capsule according to any one of Embodiments 1 to 10, in which the film has a thickness of 50 to 250 µm.

Embodiment 12. The enteric hard capsule according to any one of Embodiments 1 to 11, in which the film has an elastic modulus of 1 GPa to 5 GPa after humidity conditioning at a relative humidity of 63% at 25° C.

Embodiment 13. The enteric hard capsule according to any one of Embodiments 1 to 11, in which the film has a rate of elongation at break of 2% to 30% after humidity conditioning at a relative humidity of 22% at 25° C.

Embodiment 14. The enteric hard capsule according to any one of Embodiments 1 to 13, in which the film of the enteric hard capsule contains a sea-island structure including island phases composed substantially of the first component and a sea phase that is a mixed phase of the first component and the second component.

Embodiment 15. The enteric capsule according to Embodiment 14, in which the sea phase further contains the third and fourth components.

Embodiment 16. The enteric hard capsule according to Embodiment 14 or 15, in which the island phases have a minor axis with a length of 0.1 µm or more and less than 30 µm.

Embodiment 17. The enteric hard capsule according to any one of Embodiments 1 to 16, in which the enteric hard capsule has a dissolution rate of 10% or less after the elapse of two hours in a dissolution test using a solution having a pH of 1.2.

Embodiment 18. The enteric hard capsule according to Embodiment 17, in which the enteric hard capsule has a dissolution rate of 75% or more after the elapse of 45 minutes in a dissolution test using a solution having a pH of 6.8.

Embodiment 19. The enteric hard capsule according to Embodiment 17, in which the enteric hard capsule takes 60 minutes or more before reaching a dissolution rate of 75% or more in a dissolution test using a solution having a pH of 6.8.

Embodiment 20. The enteric hard capsule according to Embodiment 18 or 19, in which the enteric hard capsule has a dissolution rate of 30% or less after the elapse of two hours in a dissolution test using a solution having a pH of 4.0.

Embodiment 21. An enteric hard capsule preparation liquid, comprising a component i, a component ii, a basic neutralizing agent acceptable pharmaceutically or as a food additive, and a solvent,
  in which the component i is methylcellulose and/or hydroxypropyl methylcellulose having a viscosity value of 6 mPa·s or more, and
  in which the component ii is an enteric methacrylic acid copolymer.

Embodiment 22. The enteric hard capsule preparation liquid according to Embodiment 21, in which the component i has a viscosity value of 10 mPa·s or more.

Embodiment 23. The enteric hard capsule preparation liquid according Embodiment 21 or 22, in which the component i is dispersed as solid particles.

Embodiment 24. The enteric capsule preparation liquid according to any one of Embodiments 20 to 22, in which the component i is hydroxypropyl methylcellulose of substitution degree type 2910 or 2906.

Embodiment 25. The enteric hard capsule preparation liquid according to any one of Embodiments 21 to 24, in which some of the component ii has been partially neutralized with the basic neutralizing agent.

Embodiment 26. The enteric hard capsule preparation liquid according to Embodiment 25, in which the degree of neutralization of the partial neutralization is 2 to 20% based on an equivalent necessary for complete neutralization of the component ii.

Embodiment 27. The enteric hard capsule preparation liquid according to Embodiment 26, in which degree of neutralization of the partial neutralization is 5 to 15% based on an equivalent necessary for complete neutralization of the component ii.

Embodiment 28. The enteric hard capsule preparation liquid according to any one of Embodiments 21 to 27, in which the component ii is dispersed as colloidal particles.

Embodiment 29. The enteric hard capsule preparation liquid according to any one of Embodiments 21 to 28, in which the enteric methacrylic acid copolymer is a copolymer composed of 40 to 60% by mass of methacrylic acid and 60 to 40% by mass of ethyl acrylate.

Embodiment 30. The enteric hard capsule preparation liquid according to any one of Embodiments 21 to 29, containing a water-insoluble alkyl (meth)acrylate ester copolymer and/or ethyl cellulose as a component iii.

Embodiment 31. The enteric hard capsule preparation liquid according to Embodiment 30, in which the component iii is dispersed as colloidal particles.

Embodiment 32. The enteric hard capsule preparation liquid according to any one of Embodiments 21 to 31, further comprising at least one selected from the group consisting of a plasticizer and a surfactant acceptable pharmaceutically or as a food additive and as a component iv.

Embodiment 33. The enteric hard capsule preparation liquid according to Embodiment 32, in which the component i is contained at a rate of 30 to 70% by mass based on the total mass of the component i, the component ii, the component iii and the component iv contained in the enteric hard capsule preparation liquid, which is taken as 100% by mass.

Embodiment 34. The enteric hard capsule preparation liquid according to Embodiment 32 or 33, in which the component ii is contained at a rate of 30 to 60% by mass based on the total mass of the component i, the component ii, the component iii and the component iv contained in the enteric hard capsule preparation liquid, which is taken as 100% by mass Embodiment 35. The enteric hard capsule preparation liquid according to any one of Embodiments 32 to 34, in which the component iii is contained at a rate of 0 to 30% by mass based on the total mass of the component i, the component ii, the component iii and the component iv contained in the enteric hard capsule preparation liquid, which is taken as 100% by mass.

Embodiment 36. The enteric hard capsule preparation liquid according to any one of Embodiments 32 to 35, in which the component iv is contained at a rate of 0 to 12% by mass based on the total mass of the component i, the component ii, the component iii and the component iv contained in the enteric hard capsule preparation liquid, which is taken as 100% by mass.

Embodiment 37. The enteric hard capsule preparation liquid according to any one of Embodiments 21 to 36, in which the basic neutralizing agent is at least one selected from the group consisting of sodium hydroxide, potassium hydroxide, calcium hydroxide and magnesium hydroxide.

Embodiment 38. The preparation liquid according to any one of Embodiments 32 to 37, in which the total amount of the component i, the component ii, the component iii and the component iv is 12 to 30% by mass based on the enteric hard capsule preparation liquid, which is taken as 100% by mass.

Embodiment 39. The enteric hard capsule preparation liquid according to any one of Embodiments 21 to 38, having a viscosity of 100 to 10,000 mPa·s.

Embodiment 40. A method for preparing an enteric hard capsule preparation liquid, comprising a step of mixing a component i and a component ii under a condition where a basic neutralizing agent acceptable pharmaceutically or as a food additive is present in a solvent, in which the component i is methylcellulose and/or hydroxypropyl methylcellulose having a viscosity value of 6 mPa·s or more, and the component ii is an enteric methacrylic acid copolymer.

Embodiment 41. The method for preparing an enteric hard capsule preparation liquid according to Embodiment 40, in which the component i has a viscosity value of 10 mPa·s or more.

Embodiment 42. The method for preparing an enteric hard capsule preparation liquid according to any one of Embodiment 40 or 41, in which the component i is hydroxypropyl methylcellulose of substitution degree type 2910 or substitution degree type 2906.

Embodiment 43. The method for preparing an enteric hard capsule preparation liquid according to any one of Embodiments 40 to 42, in which the enteric methacrylic acid copolymer is a copolymer composed of 40 to 60% by mass of methacrylic acid and 60 to 40% by mass of ethyl acrylate.

Embodiment 44. The method for preparing an enteric hard capsule preparation liquid according to any one of Embodiments 40 to 43, in which the basic neutralizing agent is at least one selected from the group consisting of sodium hydroxide, potassium hydroxide, calcium hydroxide, and magnesium hydroxide.

Embodiment 45. The method for preparing an enteric hard capsule preparation liquid according to any one of Embodiments 40 to 44, comprising:
a step A: a step of providing a partially neutralized solution of the component ii, and
a step B: a step of providing a partially dissolved solution of the component i.

Embodiment 46. The method for preparing an enteric hard capsule preparation liquid according to Embodiment 45, in which the step A is a step of neutralizing the component ii at least partially with a basic neutralizing agent acceptable pharmaceutically or as a food additive to dissolve the component ii in the solvent to prepare a partially neutralized solution, and the component ii in the partially neutralized solution has a degree of neutralization of 2 to 20% based on a neutralization equivalent necessary for complete neutralization of the component ii.

Embodiment 47. The method for preparing an enteric hard capsule preparation liquid according to Embodiment 46, in which the degree of neutralization is 5 to 15%.

Embodiment 48. The method for preparing an enteric hard capsule preparation liquid according to any one of Embodiments 45 to 47, in which the step A is a step of adding a basic neutralizing agent to a fluid dispersion of colloidal particles of the component ii to obtain a partially neutralized solution.

Embodiment 49. The method for preparing an enteric hard capsule preparation liquid according to any one of Embodiments 45 to 47, in which the step A is a step of dispersing a solid powder of the component ii in a solvent followed by adding a basic neutralizing agent to obtain a partially neutralized solution.

Embodiment 50. The method for preparing an enteric hard capsule preparation liquid according to any one of Embodiments 45 to 49, in which the step B is a step of preparing a partially dissolved solution in which the component i is partially dissolved in the partially neutralized solution containing the component ii, and the step of preparing a partially dissolved solution is a step of preparing a fluid dispersion by adding the component i to the partially neutralized solution containing the component ii at a first temperature T1 that is equal to or higher than a cloud point T0 of the component i and partially dissolving the component i at a second temperature T2 that is lower than the cloud point.

Embodiment 51. The method for preparing an enteric hard capsule preparation liquid according to Embodiment 50, further comprising a step of holding the solution obtained in the step of mixing at a third temperature T3 that is lower than the cloud point of the component i.

Embodiment 52. The method for preparing an enteric hard capsule preparation liquid according to Embodiment 51, in which the temperature T3 is equal to or higher than T2.

Embodiment 53. The method for preparing an enteric hard capsule preparation liquid according to Embodiment 52, in which the third temperature T3 is in the range of 30° C. to 65° C.

Embodiment 54. The method for preparing an enteric hard capsule preparation liquid according to any one of Embodiments 50 to 53, in which the first temperature T1 is in the range of 60° C. to 90° C.

Embodiment 55. The method for preparing an enteric hard capsule preparation liquid according to any one of Embodiments 40 to 54, in which the enteric hard capsule preparation liquid has a viscosity of 100 to 10,000 mPa·s.

Embodiment 56. A method for preparing an enteric hard capsule comprising:
a first step of dipping a mold pin into an enteric hard capsule preparation liquid according to any one of Embodiments 21 to 39 or an enteric hard capsule preparation liquid obtained by a preparation method according to any one of Embodiments 40 to 55, the mold pin having a surface temperature that is lower than a temperature of the enteric hard capsule preparation liquid; and
a second step of pulling up the mold pin from the enteric hard capsule preparation liquid and drying the enteric hard capsule preparation liquid adhering to the mold pin.

Embodiment 57. The method for preparing an enteric hard capsule according to Embodiment 56, in which the enteric hard capsule preparation liquid has a temperature of 30 to 65° C.

Embodiment 58. The method for preparing an enteric hard capsule according to Embodiment 56 or 57, in which the mold pin has a surface temperature of 5 to 30° C. before being dipped into the preparation liquid.

Embodiment 59. The method for preparing an enteric hard capsule according to any one of Embodiments 56 to 58, in which the enteric hard capsule preparation liquid adhering to the mold pin is dried at a temperature lower than 40° C.

Embodiment 60. An enteric hard capsule formulation, comprising an enteric hard capsule according to any one of Embodiments 1 to 20 sealed with a sealing liquid, the sealing liquid being composed primarily of a solution obtained by diluting an enteric methacrylic acid copolymer which has been partially neutralized and triethyl citrate with a water/ethanol or water/isopropanol mixed solvent.

Embodiment 61. An enteric hard capsule formulation, comprising an enteric hard capsule according to any one of Embodiments 1 to 20 sealed with a sealing liquid composed primarily of a solution obtained by diluting non-neutralized hydroxypropyl methylcellulose acetate succinate with a water/ethanol or water/isopropanol mixed solvent.

Embodiment 62. A hard capsule formulation, comprising an enteric hard capsule according to any one of Embodiments 1 to 20 filled with an active drug, and adapted to have a dissolution rate of the active drug of 10% or less after the elapse of two hours in a dissolution test using a solution having a pH of 1.2.

Embodiment 63. The hard capsule formulation according to Embodiment 62, comprising an enteric hard capsule according to any one of Embodiments 1 to 20 filled with an active drug, and adapted to have a dissolution rate of the active drug of 75% or more after the elapse of 45 minutes in a dissolution test using a solution having a pH of 6.8.

Embodiment 64. The hard capsule formulation according to Embodiment 62, comprising an enteric hard capsule according to any one of Embodiments 1 to 20 filled with an active drug, and adapted to take 60 minutes or more before having a dissolution rate of the active drug of 75% or more in a dissolution test using a solution having a pH of 6.8.

Embodiment 65. The hard capsule formulation according to Embodiment 63 or 64, comprising an enteric hard capsule according to any one of Embodiments 1 to 20 filled with an active drug, adapted to have a dissolution rate of the active drug of 30% or less after the elapse of two hours in a dissolution test using a solution having a pH of 4.0, provides Embodiment 66. A double hard capsule formulation, comprising an enteric hard capsule according to any one of Embodiments 1 to 20, and a hard capsule containing the enteric hard capsule and dissolvable under an acidic condition.

Embodiment 67. A hard capsule, comprising a hard capsule film having a two-phase structure consisting of core particle phases composed of fine particles of a water-soluble polymer free of an active drug and acceptable pharmaceutically or as a food additive, and a binding phase covering surfaces of the core particles and/or binding the core particles, in which the binding phase primarily contains a functional polymer that is different from the water-soluble polymer and can control dissolution characteristics of the core particle phases.

Embodiment 68. The hard capsule according to Embodiment 67, in which the water-soluble polymer is a water-soluble cellulose compound prepared from a dry ingredient powder with an average particle size of 1 to 100 μm and having a lower critical solution temperature.

Embodiment 69. The hard capsule according to Embodiment 68, in which the water-soluble polymer is methylcellulose and/or hydroxypropyl methylcellulose having a viscosity value of 6 mPa·s or more.

Embodiment 70. The hard capsule according to Embodiment 67, in which the functional polymer is an enteric coating base and/or sustained-release coating base that are water-soluble or form an aqueous dispersion of colloidal particles.

Embodiment 71. The hard capsule according to Embodiment 70, in which the functional polymer is a colloidal dispersion of an enteric methacrylic acid copolymer.

Embodiment 72. An enteric or sustained-release hard capsule, comprising a film containing a component i and a component ii,
in which the component i is a water-soluble cellulose polymer prepared from a dry ingredient powder with an average particle size of 1 to 100 μm and having a lower critical solution temperature, and the component ii is an enteric coating base and/or a sustained-release coating base that are water-soluble or form an aqueous dispersion of colloidal particles, and
in which the enteric or sustained-release hard capsule is formed through a process including at least a first step of dipping a mold pin into an enteric or sustained-release hard capsule preparation liquid maintained at a temperature close to the lower critical solution temperature of the component i, the mold pin having a surface temperature that is lower than the temperature of the preparation liquid and the preparation liquid being an aqueous dispersion containing undissolved fine particles of the component i and the component ii; and a second step of pulling up the mold pin from the preparation liquid and drying the preparation liquid adhering to the mold pin.

Embodiment 73. An enteric hard capsule, comprising a film containing a component i and a component ii,
in which the component i is methylcellulose and/or hydroxypropyl methylcellulose with a viscosity value of 6 mPa·s or more, and the component ii is an enteric methacrylic acid copolymer, and
in which the enteric hard capsule is formed through a process including at least a first step of dipping a mold pin into an enteric hard capsule preparation liquid maintained at 30 to 65° C., the mold pin having a surface temperature that is lower than a temperature of the preparation liquid and the enteric hard capsule preparation liquid being composed of an aqueous dispersion containing undissolved fine particles of the component i and component ii and further containing a basic neutralizing agent with a concentration sufficient to partially neutralize the component ii, and, and a second step of pulling up the mold pin from the preparation liquid and drying the preparation liquid adhering to the mold pin.

Embodiment 74. A hard capsule preparation liquid, comprising an aqueous solvent in which fine particles of a water-soluble polymer free of an active drug and acceptable pharmaceutically or as a food additive are dispersed, and in which a functional polymer different from the water-soluble polymer is further dissolved and/or colloidal particles of a functional polymer different from the water-soluble polymer are further dispersed.

Advantageous Effects of Invention

According to the present invention, it is possible to provide a hard capsule composed of a hard capsule film that can be molded by a cold gelation method and has enteric properties. Also, according to the present invention, it is possible to prepare an enteric hard capsule without using a gelling agent. In addition, the hard capsule can be filled with a content using a conventionally used capsule filling machine.

BRIEF DESCRIPTION OF DRAWINGS

FIG. 8 shows SEM images of cross-sections of cast films of Reference Example 4.

DESCRIPTION OF EMBODIMENTS

1. Description of Terms and Materials

Figure 1:
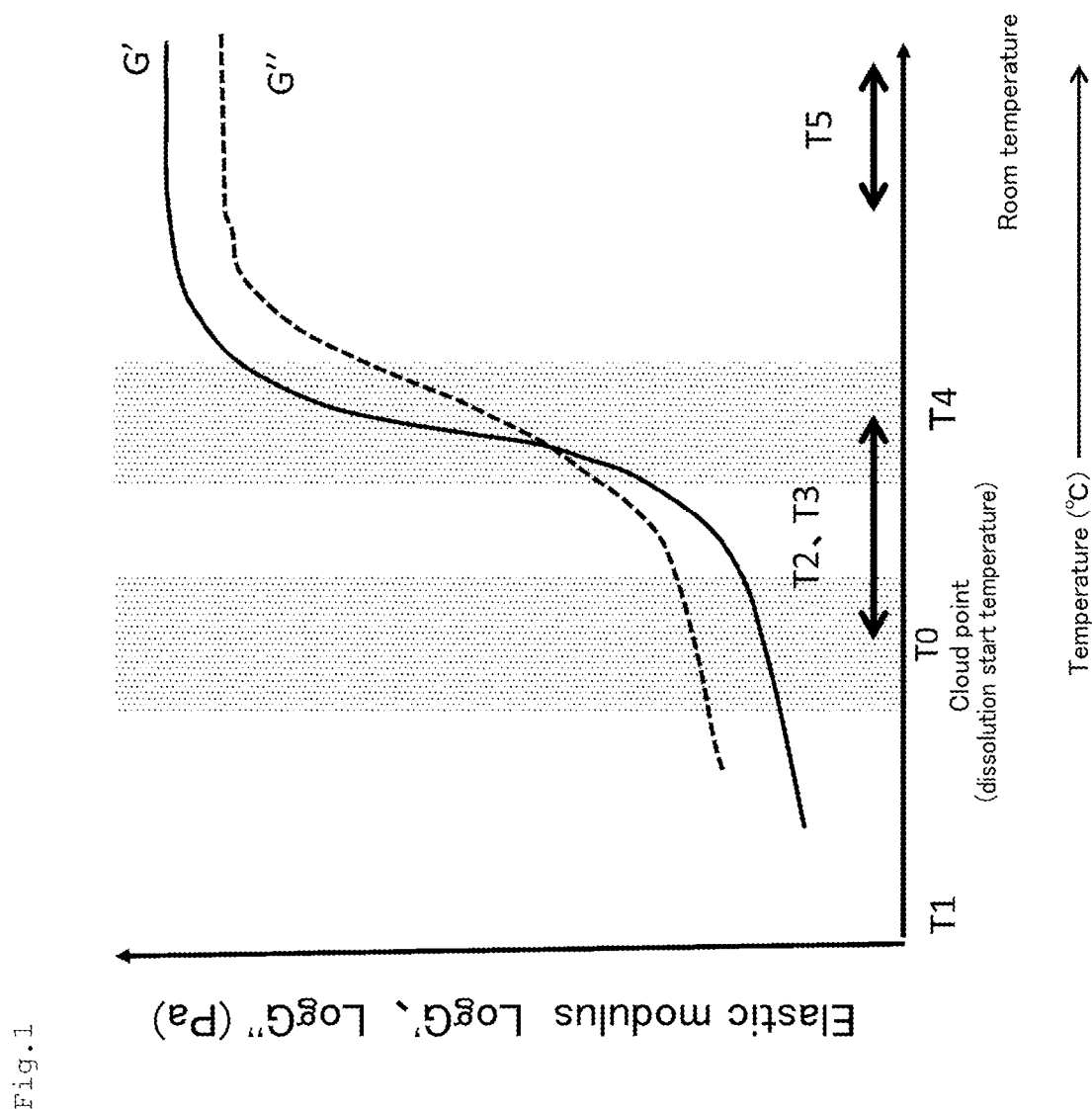
FIG. 1 is a diagram illustrating a schematic diagram of a dynamic viscoelasticity behavior of an enteric hard capsule preparation liquid during a temperature decreasing process. T0 indicates a cloud point or a dissolution start temperature. T1, T2 and T3 indicate a first temperature, a second temperature and a third temperature, respectively, described in the specification. T4 indicates a temperature at which an abrupt increase in viscosity starts. T5 indicates room temperature (20° C. to 25° C.).

First, the terms and materials used in the present specification, claims etc. are described. The terms and materials relating to the present invention complies with the description in this section unless otherwise stated.

In the present invention, a "hard capsule" is an empty capsule of a produced capsule film to be filled with a content. Usually, a hard capsule consists of a cap portion and a body portion, and is also referred to as "hard capsule" or "two-piece capsule." A "hard capsule" in the present invention has a shape identical or similar to that of a commercially-available conventional hard capsule intended for oral administration to a human or animal subject.

The "hard capsule" of the present invention does not include a soft capsule produced by filling a content between two films and bonding the films to each other, a seamless capsule produced by dropping a content together with a film solution into a coagulating liquid, and a microcapsule prepared by incorporating therein an active ingredient by precipitation or emulsification of a base material.

Also, in the present invention, an empty hard capsule is simply referred to as "hard capsule" or "capsule," and a capsule filled with a content is referred to as "hard capsule formulation."

In the present invention, an "enteric hard capsule" referred to a hard capsule in which the film itself of the capsule body has "enteric" properties that meet the following conditions.

In other words, "enteric" refers to properties that satisfy at least the following condition (i).

(i) In a dissolution test described in Japanese Pharmacopoeia revised 17th Edition (hereinafter sometimes referred to simply as "17th Pharmacopoeia"), the dissolution rate of the content is 25% or less, preferably 10% or less, when the test subject is immersed in a first liquid at 37° C.±0.5° C. for two hours. The first liquid has a pH of about 1.2. The first liquid can be prepared by adding 7.0 ml of hydrochloric acid and water to 2.0 g of sodium chloride to make 1000 ml, for example.

In addition to the above-mentioned condition (i), being "enteric" preferably also satisfies the following condition (ii). (ii) In the above-mentioned dissolution test, the content is dissolved out when the test subject is immersed in a second liquid at 37° C.±0.5° C. The second liquid has a pH of about 6.8. The second liquid can be prepared by adding 1 volume of water to 1 volume of a phosphate buffer solution obtained by dissolving 3.40 g of potassium dihydrogen phosphate and 3.55 g of anhydrous disodium hydrogen phosphate in water to make 1000 mL, for example. Here, there is no limitation on the time at which the dissolution rate of the content in the second liquid is measured. For example, when the content is required to be dissolved out relatively quickly in an upper intestinal tract (small intestine) after reaching the intestine, the dissolution rate should reach 75% or more, preferably 80%, more preferably 90% or more 45 minutes after the test subject is immersed in the second liquid. In addition, the dissolution rate should reach 75% or more, preferably 80%, more preferably 90/or more one hour after the test subject is immersed in the second liquid, for example.

On the other hand, for a formulation intended to be prevented from dissolving until reaching the lower intestinal tract (such as the large intestine) in order to deliver the drug to the lower intestinal tract, it is preferred that it takes 60 minutes or more before the dissolution rate reaches 75% after test subject is immersed in the second liquid. It is preferred that 75% or more of the content is dissolved out within 12 hours in order to prevent the content from being directly discharged out of the body.

In addition, in view of the fact that the variation of the pH of the human gastric juice is about 1.2 to 4, there is a case where the acid resistance in an intermediate pH range is evaluated. For a dissolution test in this case, a buffer solution having a pH in an intermediate range may be used. In the present invention, evaluation may be performed with a buffer solution having a pH of about 4 as described below. The composition of the buffer solution can be prepared by dissolving 3.378 g of citric acid hydrate and 2.535 g of anhydrous disodium hydrogen phosphate in water to make 1000 mL, for example.

In the present invention, as a condition for a particularly excellent acid resistance, the dissolution rate preferably reaches 30% or less, more preferably 25% or less, still more preferably 20% or less two hours after the test subject is immersed in the above-mentioned buffer solution.

Figure 6:
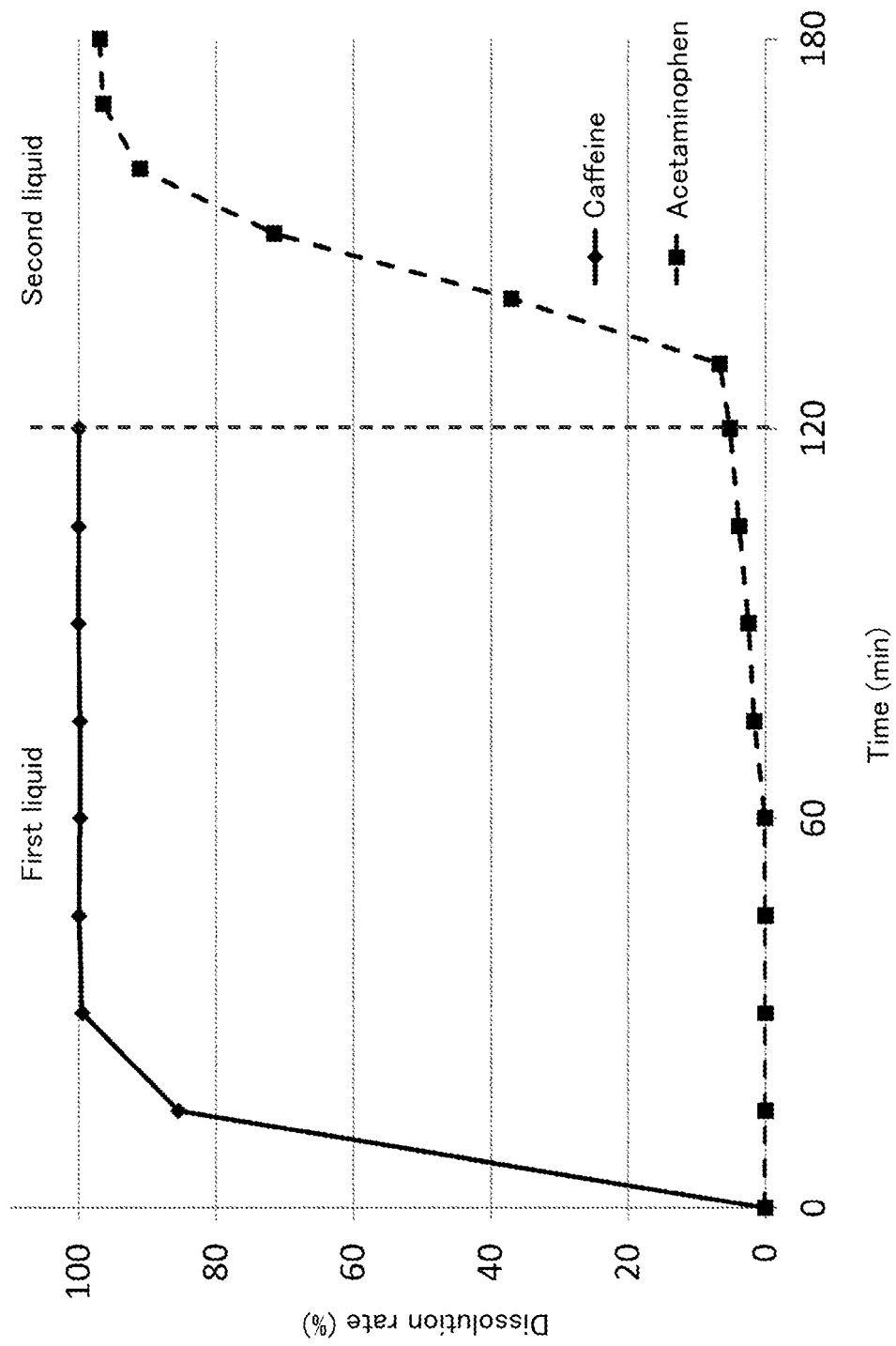
FIG. 6 is a diagram showing the dissolution characteristics of a double capsule using therein an enteric hard capsule according to the present disclosure.

The dissolution test can be conducted in accordance with the dissolution test method specified in the 17th Pharmacopoeia (the 17th Pharmacopoeia, 6.10-1.2 Paddle Method (paddle rotational speed 50 revolutions/min), with a sinker corresponding to FIG. 6. 10-2a).

The content for use in the dissolution test are not limited as long as it is dissolved quickly in the test solution and can be quantified by a known method. Examples include acetaminophen.

In the present invention, among cellulose ethers which are cellulose compounds (polymers) that have no ionic group in the molecule but become water-soluble by having a nonionic hydrophilic group such as —OH or =O, and in which some of hydroxyl groups on the glucose ring of the cellulose are etherified, methylcelluloses (MC) and/or hydroxypropyl methylcellulose (sometimes referred to as "hypromellose" or "HPMC" in this specification), in particular, is contained as a first component. These are nonionic and particularly water-soluble. These have a higher hardness (elastic modulus) than hydroxypropyl cellulose (HPC), which is a water-soluble cellulose ether, and preferred mechanical strength as a hard capsule can be obtained More specifically, hydroxypropyl methylcelluloses and methylcelluloses specified in Japanese Pharmacopoeia are used. For example, the degree of substitution of methoxy groups of the hydroxypropyl methylcelluloses is preferably 16.5 to 30.0% by mass, more preferably 19.0 to 30.0% by mass, particularly preferably 28.0 to 30.0% by mass, and the degree of substitution of hydroxypropoxy groups is preferably 4.0 to 32.0% by mass, more preferably 4.0 to 12.0% by mass, particularly preferably 7.0 to 12.0% by mass. Also, the degree of substitution of methoxy groups of the methylcellulose is preferably 26.0 to 33.0% by mass, more preferably 28.0 to 31.0% by mass. These degrees of substitution can be measured by a method in accordance with the method for measuring the degree of substitution of hydroxypropyl methylcelluloses and methylcelluloses described in the 17th Pharmacopoeia.

Above all, hydroxypropyl methylcellulose represented by the following formula is a cellulose compound that is optimum in that it has excellent film moldability and mechanical strength even with a low moisture content.

[Chemical Formula 1]

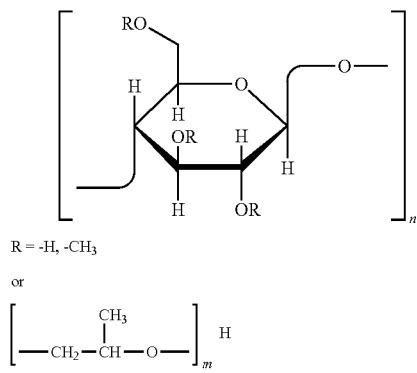

$R = -H, -CH_3$ or (wherein n and m each represent an arbitrary integer).

The hydroxypropyl methylcellulose for use in the present invention include hypromelloses of substitution degree grades (types) 2910, 2906 and 2208 specified in the 17th Pharmacopoeia. Among them, substitution degree types 2910 and 2906 are more preferred.

TABLE 1

| Substitution degree type | Methoxy group (%) | | Hydroxypropoxy group (%) | |
|---|---|---|---|---|
| | Lower limit | Upper limit | Lower limit | Upper limit |
| 1828 | 16.5 | 20.0 | 23.0 | 32.0 |
| 2208 | 19.0 | 24.0 | 4.0 | 12.0 |
| 2906 | 27.0 | 30.0 | 4.0 | 7.5 |
| 2910 | 28.0 | 30.0 | 7.0 | 12.0 |

Also, the hydroxypropyl methylcellulose of the present invention include hypromellose with the following molecular weight that is approved for use as a food additive in Japan.

<Molecular Weight>
Unsubstituted structural unit: 162.14
Substituted structural unit: about 180 (degree of substitution 1.19), about 210 (degree of substitution 2.37)
Polymer: about 13.000 (n=about 70) to about 200,000 (n=about 1000).

Commercially available methylcelluloses and hydroxypropyl methylcelluloses include Japanese Pharmacopoeia METOLOSE (trademark) series and METOLOSE series for food additives from Shin-Etsu Chemical Co., Ltd., AnyCoat-C or AnyAddy (trademark) series from Lotte (former Samsung) Fine Chemicals Co., Ltd., METHOCEL (trademark) series from DOW Chemical Company, and Benecel (trademark) series from Ashland.

In the present disclosure, methylcellulose (MC) or hydroxypropyl methylcellulose (hypromellose, HPMC) having a viscosity value of 6 mPa·s or more, and a mixture of these are each hereinafter referred to as "water-soluble cellulose compound."

In the present disclosure, it is preferred to use water-soluble cellulose having a "viscosity value" of 6 mPa·s or more when in the form of a 2% by mass aqueous solution at 20° C. In the following, this viscosity value may be sometimes referred to simply as "viscosity value." The "viscosity value" can be measured in accordance with the section of methylcellulose and hypromellose, which was formulated based on the International Harmonization Plan in and after the 15th Pharmacopoeia. In other words, the "viscosity value" refers to the value of viscosity (mPa·s) of a 2% by mass aqueous solution of the water-soluble cellulose at 20° C.±0.1° C. For measurement of the "viscosity value," the first method (Ubbelohde method) in General Test Method 2.53 Viscosity Measurement Method is used when the "viscosity value" is less than 600 mPa·s, and the second method, 2.1.2 Single Cylindrical Rotary Viscometer (Brookfield type viscometer) in General Test Method 2.53 Viscosity Measurement Method is used when the "viscosity value" is 600 mPa·s or more.

Also, the viscosity labeled by the compound manufacturer (sometimes referred to as "viscosity grade value") may be employed as the "viscosity value." With regard to the labeled viscosity and the range of the labeled viscosity, for example, METOLOSE (tradename) series from Shin-Etsu Chemical Co., Ltd. are described to have a viscosity value that is 80 to 120% of the labeled viscosity when the labeled viscosity is less than 600 mPa·s and a viscosity value that is 75 to 140% of the labeled viscosity when the labeled viscosity is 600 mPa·s or more. With regard to the lower limit value of 100 mPa·s in the present invention, the labeled viscosity can be directly used as the "viscosity value" as long as the intent of the present invention is not impaired.

In the present disclosure, a preferred lower limit value of the "viscosity value" is 6 mPa·s, more preferably 10 mPa·s.

A preferred upper limit value of the "viscosity value" is 1000 mPa·s, more preferably 500 mPa·s, still more preferably 100 mPa·s. The weight-average molecular weight (g/Mol) corresponding to a "viscosity value" of 6 to 1000 mPa·s is approximately 35,000 to 200,000.

A water-soluble cellulose compound in a solid state is usually supplied as solid fine particles having a particle size on the order of 1 to several hundred μm. The average grain size (average particle size) thereof is preferably in the range of 1 to 100 μm. Here, the average grain size means the volume average particle size (MV) of the primary particles thereof, and can be obtained with a generally used laser diffraction type grain size distribution measuring device (such as "Microtrack grain size distribution meter MT3300II EX" manufactured by MicrotrackBEL Corp.), for example. Preferably, the volume fraction of the particles with a particle size of 100 μm or less is 50% or more, more preferably 60% or more. Also, as the first component of the present invention, a mixture of MCs or HPMCs may be used or MCs and/or HPMCs having different viscosity values may be used in mixture as long as at least one of these has a viscosity value of 6 mPa·s or more.

Also, this compound is characterized by having a lower critical solution temperature (LCST), that is, T0. The LCST refers to such a temperature that the compound start dissolving when the water temperature becomes lower than T0 during a temperature decreasing process and the polymer in a solution gelates or undergoes phase separation when the water temperature becomes higher than T0 during a temperature increasing process (Non-Patent Document 7).

When a water-soluble cellulose compound is dissolved in a solvent at around room temperature, the solution turns transparent. In the process of increasing the temperature of the solution again, gelation or phase separation from the solvent is observed as turbidity of the aqueous solution at T0. This is the reason that T0 is referred to as "cloud point." In the case where undissolved water-soluble cellulose particles (usually 1 to 100 μm in diameter) are dissolved in water, when the particles are first dispersed at the cloud point T0 or higher and then dissolved by decreasing the water temperature, the particles gradually start dissolving from the surfaces but do not dissolve completely and keep a dispersed state of solid fine particles until the temperature reaches about 40° C. In other words, the solution turns into a fluid dispersion (suspension). When the temperature is further decreased to around room temperature, a completely transparent solution is obtained. When the temperature of this solution is increased again, gelation or phase separation from the solvent occurs at around the cloud point but the water-soluble cellulose compound does not return to the original fluid dispersion of undissolved solid fine particles. MC and HPMC tend to form a gel in which water molecules are incorporated in a network of cellulose polymer, and HPC tends to undergo a phase separation into a solid phase of the cellulose polymer and an aqueous phase. The lower critical solution temperature (hereinafter sometimes referred to also as "dissolution temperature") and the cloud point are named focusing on the temperature decreasing process or the temperature increasing process, respectively, and generally agree with each other although there may be slight difference therebetween depending on the history of the temperature decreasing or temperature increasing process. In the following description, these are dealt with equivalently.

The cloud point of a water-soluble cellulose compound is usually in the range of 40 to 70° C. although it depends, for example, on the pH of the aqueous solution (Japanese Journal of Polymer Science and Technology, Vol. 38(1981), p. 133-137, J. Polym. Sci. C, Vol. 36(1971), p. 491-508). For example, the cloud point is about 60° C. for HPMC and about 40° C. for MC.

In the present invention, as an enteric polymer for ensuring an "enteric" function, an enteric methacrylic acid copolymer is used as a second component. Conventionally, enteric hard capsules mainly using an enteric cellulose compound as an enteric polymer, specifically, hydroxypropyl methylcellulose phthalate (HPMCP), hydroxypropyl methylcellulose acetate succinate (HPMCAS) or cellulose acetate phthalate (CAP), are known (Patent Documents 12 to 19). However, as an intrinsic property of enteric polymers, enteric cellulose compounds have a disadvantage of being liable to undergo generation of a free carboxylic acid resulting from decomposition of carboxyl groups when stored under a high humidity condition for a long time (Non-Patent Document 6, in particular FIG. 3). On the other hand, enteric methacrylic acid copolymers have an advantage of being very stable during extended storage and having a low water vapor permeation rate, in other words, having an excellent moisture-proof property as a film (Non-Patent Document 6, in particular Table 2).

The "methacrylic acid copolymer" is also referred to as "methacrylate copolymer." The methacrylic acid copolymer is a polymer containing methacrylic acid monomer units in its skeleton.

More preferably, the methacrylic acid copolymer is composed of methacrylic acid monomer units as anionic groups and alkyl ester monomer units of acrylic acid or methacrylic acid that are neutral (collectively referred to as "alkyl (meth)acrylate ester monomer"). Alkyls that form an ester bond with acrylic acid or methacrylic acid include alkyls having 1 to 4 carbon atoms, preferably alkyls having 1 to 3 carbon atoms. A more specific alkyl ester of acrylic acid or methacrylic acid is at least one selected from the group consisting of methyl methacrylate, ethyl methacrylate, butyl methacrylate, methyl acrylate, ethyl acrylate and butyl acrylate.

More preferred enteric methacrylic acid copolymer includes a copolymer of methacrylic acid (formula (I)) shown below with ethyl acrylate (formula (IV)), or a copolymer of methacrylic acid (formula (I)) with methyl methacrylate (formula (II)) and methyl acrylate (formula (III)).

[Chemical Formula 2]

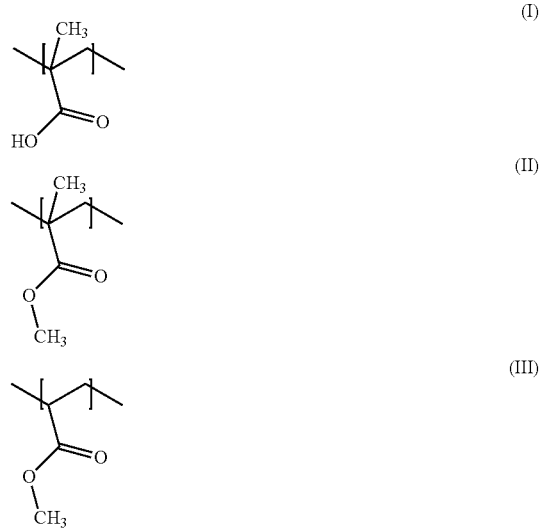

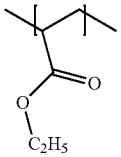
(IV)

The methacrylic acid copolymer is preferably enteric. In other words, it is preferred that the methacrylic acid copolymer has such a threshold property that it is hardly soluble in an aqueous solution with a pH of less than about 5 but immediately start dissolving when the pH is about 5 or more. Specifically, this property is adjusted by the blending ratio between the methacrylic acid monomer and the other alkyl (meth)acrylate ester monomer units in the copolymer.

The copolymer preferably contains at least 5%, preferably 5 to 70%, particularly 8 to 60%, more preferably 30 to 60%, of the methacrylic acid monomer units based on the total number of monomers (total number of units, or total number of groups) forming the copolymer, which is taken as 100, The percentage of each monomer unit can be easily converted to % by mass using the molecular weight of each monomer unit.

A preferred methacrylic acid copolymer is a polymer composed of 40 to 60% by mass of methacrylic acid (molecular weight 86.04) and 60 to 40% by mass of methyl methacrylate (molecular weight 100.05) or 60 to 40% by mass of ethyl acrylate (molecular weight 100.05) (such as EUDRAGIT (trademark) L100 or EUDRAGIT (trademark) L100-55). EUDRAGIT (trademark) L100-55, which is a copolymer of 50% by mass of methacrylic acid with 50% by mass of ethyl acrylate, is particularly suitable. EUDRAGIT (trademark) L30D-55 is an aqueous dispersion containing about 30% by mass of EUDRAGIT (trademark) 100-55. In the following, L30D-55 and 1100-55 may be sometimes referred to as L30D55 and L1.0055, respectively. These methacrylic acid copolymers are set to dissolve at a pH of about 5.5 or more.

Another preferred example is a copolymer composed of 5 to 15% by mass of methacrylic acid, 10 to 30% by mass of methyl methacrylate, and 50 to 70% by mass of methyl acrylate (molecular weight 86.04). More specifically, preferred is EUDRAGIT (trademark) FS, which is a copolymer composed of 10% by mass of methacrylic acid, 25% by mass of methyl methacrylate, and 65% by mass of methyl acrylate. EUDRAGIT (trademark) FS30D is a fluid dispersion containing about 30% by mass of EUDRAGIT (trademark) FS. This methacrylic acid copolymer is set to dissolve at a pH of about 7 or more, and may be used in the case where delivery to the large intestine, which is an environment with a higher pH, is intended.

In general, the above-mentioned enteric methacrylic acid copolymer first produces an aqueous dispersion containing very small colloidal particles (sometimes referred to as "aqueous emulsion" or "latex") through a copolymerization process from a monomer level in an aqueous solution by an emulsion polymerization process. Thus, because an aqueous dispersion (emulsion) of very fine and stable colloidal particles with an average particle size of less than 1 μm is obtained without a dissolution step by neutralization of the solid polymer component with a basic neutralizing agent, it is suitable for use as an aqueous dispersion (Non-Patent Document 1, Chapter. 9).

Water dispersions and commercialized methacrylic acid copolymers equivalent to EUDRAGIT series (Evonik Industries AG) L30D-55 also include, but are not necessarily limited to, Kollicoat series (BASF) MAE30D/DP, and Polykid series (Sanyo Chemical Industries, Ltd.) PA-30. Although these water dispersions (aqueous emulsions) usually contain less than 0.3% of residual monomers and trace amounts of polysorbate 80 and sodium lauryl sulfate from the production process thereof and for stabilization, these may be acceptable as impurities inevitably contained in the hard capsule film and the hard capsule preparation liquid of the present invention.

The above-mentioned L30D-55 and its equivalents fall under the category of methacrylic acid copolymer LD specified in Japanese Pharmaceutical Excipients 2018. In other words, it is described as an emulsion of a copolymer of methacrylic acid with ethyl acrylate obtained in an aqueous solution of polysorbate 80 (Japanese Pharmacopoeia) and sodium lauryl sulfate (Japanese Pharmacopoeia), and containing 11.5 to 15.5% of methacrylic acid ($C_4H_6O_2$: 86.09) as a copolymer constituent.

Additionally, as copolymers that are not necessarily commercialized but have a blend ratio that is sufficiently known to be able to be put into practical use, materials as disclosed in Japanese Translation of PCT International Application Publication No. 2005-526546, H08-81392 and DE2135073 can be also used as appropriate for control of dissolution characteristics (such as pH (threshold) dependency, dissolving rate in a neutral to alkaline region) and mechanical strength of the present capsule. In other words, it is also described in DE2135073 that the polymers are harder as the amount of carboxyl group monomers, such as methacrylic acid (MAA) and acrylic acid (AA), among monomer units is large, and are softer as the proportion of such units as ethyl acrylate (EA) and methyl acrylate (MA) is high. It is also known that hardness, fragility (brittleness) and dissolution characteristics can be controlled by changing the blend ratios of three components among AA. MAA, MA and EA. For example, it is possible to improve crack resistance or prevent dissolution up to a pH of about 5.5 or more by replacing some of L30D55 with FS30D55.

The capsule film of the present invention contains an alkyl (meth)acrylate ester copolymer and/or ethyl cellulose as a water-insoluble polymer as a third component.

The "alkyl (meth)acrylate ester copolymer" is a substantially neutral (meth)acrylic acid copolymer, and is composed primarily of alkyl ester neutral monomer units of methacrylic acid or acrylic acid. Alkyls that form an ester bond with acrylic acid or methacrylic acid include alkyls having 1 to 4 carbon atoms, preferably alkyls having 1 to 3 carbon atoms. A more specific alkyl ester of acrylic acid or methacrylic acid is at least one selected from the group consisting of methyl methacrylate, ethyl methacrylate, butyl methacrylate, methyl acrylate, ethyl acrylate, and butyl acrylate. To be substantially neutral, the proportion of the neutral monomer is more than 95% by mass, more than 98% by mass, more than 99% by mass, or 100% by mass, for example. However, the presence of ionic groups in the polymer is not completely excluded, and a methacrylic acid copolymer containing less than 5% by mass, preferably less than 2% by mass, more preferably less than 1% by mass of ionic groups, in particular anionic groups, may be contained.

These substantially neutral alkyl (meth)acrylate ester copolymers are also water-insoluble.

More preferably, EUDRAGIT (trademark) NE or EUDRAGIT (trademark) NM type, both of which are a copolymer composed of 20 to 40% by mass of methyl methacrylate (molecular weight 100.05) and 60 to 80% by mass of ethyl acrylate (molecular weight 100.05), is suitable. Above all, EUDRAGIT (trademark) NE30D or NM30D, both of which are a copolymer (ethyl acrylate-methyl methacrylate copolymer) composed of 70% by mass of ethyl acrylate and 30% by mass of methyl methacrylate, is suitable. In each case, the copolymer may contain less than 5% by mass, preferably less than 2% by mass, preferably 1% by mass, of methacrylic acid (molecular weight 86.04).

These can first produce an aqueous emulsion (latex) containing very small colloidal particles through a copolymerization from a monomer level in an aqueous solution by an emulsion polymerization process. Thus, an aqueous dispersion (emulsion) of very fine colloidal particles with an average particle size of less than 1 μm can be obtained without a dissolution step using an organic solvent or the like despite of being water-insoluble (Non-Patent Document 1, Chapter. 9).

NE30D falls under the category of "ethyl acrylate-methyl methacrylate copolymer fluid dispersion" specified in Japanese Pharmaceutical Excipients 2018, and is described as an emulsion of a copolymer resin that is obtained by polymerization of ethyl acrylate and methyl methacrylate in an aqueous solution using a polyoxyethylene nonylphenyl ether (100 E.O.) as an emulsifier and may contain a trace amount of "dimethylpolysiloxane (for internal use)." On the other hand, NM30D may contain a trace amount of a macrogol stearyl ether as an emulsifier.

These water-insoluble alkyl (meth)acrylate ester copolymers have a glass transition temperature of lower than 100° C. or a film forming temperature (minimum film-forming temperature. MFT) of lower than 50° C., and are effective in promoting fusion-bonding between particles to provide a dry film that is transparent and does not break easily when a fluid dispersion containing colloidal particles of an enteric methacrylic acid copolymer is dried to form a film, in particular. Also, the water-insoluble alkyl (meth)acrylate ester copolymers have an advantage of not impairing acid resistance when added in an appropriate amount.

The ethyl cellulose is ethyl cellulose with a high degree of etherification of about 2.6 obtained by ethyl etherification of hydroxyl groups of cellulose, and is hardly soluble in water. ETHOCEL (trademark) series from DOW Chemical Company are available.

The ethyl cellulose also prepared into an aqueous dispersion of very fine particles with a diameter on the order of 0.01 to 0.1 μm by, for example, dissolving it in an organic solvent, finely dispersing the solution in water in the presence of an emulsifier and distilling off the organic solvent from the fluid dispersion. Usable commercially available products include Aquacoat ECD30 (FMC Technologies Inc.) and Surelease (Colorcon Inc.).

In Japanese Pharmaceutical Excipients 2018, it is specified as ethyl cellulose and an ethyl cellulose fluid dispersion. The ethyl cellulose contains 46.5 to 51.0% of ethoxy groups ($-OC_2H_5$). Also, the ethyl cellulose fluid dispersion, which is a water suspension agent composed primarily of ethyl cellulose, is a water-based polymer dispersion of ethyl cellulose fine particles (0.1 to 0.3 μm) and a mixture of the "ethyl cellulose," cetanol (Japanese Pharmacopoeia) and sodium lauryl sulfate (Japanese Pharmacopoeia). This product has a solid content concentration of 28 to 32%, and defined as containing 24.5 to 29.5% of ethyl cellulose as well as 1.7 to 3.3% of cetanol ($C_{16}H_{34}O$: 242.44) and 0.9 to 1.7% of sodium lauryl sulfate ($C_{12}H_{25}NaO_4S$: 288.38) when quantified.

The enteric hard capsule film of the present invention may further contain a plasticizer, a surfactant (emulsifier), a base, a binder, a coating agent and so on, each of which is acceptable pharmaceutically or as a food additive. Also, the enteric hard capsule film may contain a release-sustaining agent, a dissolution aid, a solubilizing agent and so on for controlling solubility, in particular, dissolution characteristics in a neutral pH range. Usable examples of the above-mentioned additives acceptable as pharmaceutical additives include, but are not limited to, those described according to application in Pharmaceutical Excipients Directory 2016 Edition (edited by Japan Pharmaceutical Excipients Association. Yakuji Nippo, Ltd.). These additives may be redundantly classified into a plurality of applications.

The plasticizer is not necessarily limited to specific substances shown in the above-mentioned Pharmaceutical Excipients Directory, and is not particularly limited as long as it can be used in pharmaceutical products or food compositions and can be added to a capsule film to impart flexibility thereto. Suitable substances are those which generally have a molecular weight (Mw) of 100 to 20,000 and have one or more hydrophilic groups, such as hydroxyl groups, ester groups or amino groups, in one molecule.

Examples include dioctyl adipate, polyester adipate, epoxidized soybean oil, epoxyhexahydrophthalic acid diesters, kaolin, triethyl citrate, glycerin, glycerin fatty acid esters, sesame oil, dimethylpolysiloxane-silicon dioxide mixtures, D-sorbitol, medium-chain fatty acid triglyceride, corn starch-derived sugar alcohol liquid, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, polysorbate 80, macrogol 1500, macrogol 400, macrogol 4000, macrogol 600, macrogol 6000, isopropyl myristate, cottonseed oil-soybean oil mixtures, glycerin monostearate and isopropyl linoleate. From the viewpoint of being excellent in compatibility and imparting high gloss, propylene glycol and polyethylene glycol are particularly preferred. The weight-average molecular weight of the polyethylene glycol is not particularly limited, but is preferably 200 to 35000 from the viewpoint of imparting high gloss. Hydroxypropyl cellulose (HPC), which is safer than MC and HPMC, can be used as a plasticizer.

The surfactant (also referred to as emulsifier) may be also used as a solubilizing agent, suspending agent, emulsifier, dispersant, dissolution aid, stabilizing agent, base or the like, and is basically a polymer having a hydrophilic group and a lipophilic group (hydrophobic group) in the molecule.

Specific examples include benzalkonium chloride, benzethonium chloride polyoxyethylene (40) monostearate (polyoxyl 40 stearate*), sorbitan sesquioleate (sorbitan sesquioleate*), polyoxyethylene (20) sorbitan monooleate (polysorbate 80*), glyceryl monostearate (glycerin monostearate*), sodium lauryl sulfate, and polyoxyethylene lauryl ether (lauromacrogol*) (*: notation in Japanese Pharmacopoeia). Other examples include sodium alkyl benzene sulfonate, sucrose fatty acid esters, polyethylene glycol monooleate, polyethylene glycol dioleate, propylene glycol fatty acid esters (such as propylene glycol monostearate and propylene glycol monocaprylate), polyoxyethylene hydrogenated castor oil, polyoxyethylene glycerin monostearate, polyoxyethylene (160) polyoxypropylene (30) glycol, and polyoxyethylene nonylphenyl ethers. The surfactant (or emulsifier) may, as described above, contain a component that inevitably remain after emulsion polymerization of a methacrylic acid copolymer or alkyl (meth)acrylate ester copolymer.

The enteric hard capsule film of the present invention may further contain a lubricant, a metal sequestering agent, a coloring agent, a light-shielding agent, a binder and so on in an amount of up to about 5% by mass. Example of the metal sequestering agent include ethylenediaminetetraacetic acid, acetic acid, boric acid, citric acid, gluconic acid, lactic acid, phosphoric acid, tartaric acid, or salts thereof, methaphosphates, dihydroxyethylglycine, lecithin, β-cyclodextrin, and combinations thereof.

The lubricant is not particularly limited as long as it can be used in pharmaceutical products or food compositions. Examples include calcium stearate, magnesium stearate, sodium stearyl fumarate, carnauba wax, starch, sucrose fatty acid esters, light anhydrous silicic acid, talc, and hydrogenated vegetable oils.

Examples of the metal sequestering agent include ethylenediaminetetraacetic acid, acetic acid, boric acid, citric acid, gluconic acid, lactic acid, phosphoric acid, tartaric acid, or salts thereof, methaphosphates, dihydroxyethylglycine, lecithin, f-cyclodextrin, or combinations thereof.

The coloring agent and light-shielding agent are not particularly limited as long as they can be used in pharmaceutical products or food compositions. Examples of the coloring agent include gambir tannin powder, turmeric extract, methylrosaniline chloride, yellow iron oxide, yellow ferric oxide, Opaspray K-1-24904, orange essence, brown iron oxide, carbon black, caramel, carmine, carotene liquid, β-carotene, photosensitizer 201, licorice extract, gold leaf, *Sasa veitchii* extract, black iron oxide, light anhydrous silicic acid, *Daemonorops draco*, zinc oxide, titanium oxide, iron sesquioxide, disazo yellow. Food Blue No. 1 and its aluminum lake, Food Blue No. 2 and its aluminum lake, Food Yellow No. 4 and its aluminum lake, Food Yellow No. 5 and its aluminum lake, Food Green No. 3 and its aluminum lake. Food Red No. 2 and its aluminum lake. Food Red No. 3 and its aluminum lake, Food Red No. 102 and its aluminum lake, Food Red No. 104 and its aluminum lake, Food Red No. 105 and its aluminum lake, Food Red No. 106 and its aluminum lake, sodium hydroxide, talc, sodium copper chlorophyllin, copper chlorophyll, hull-less barley green tea extract powder, hull-less barley green tea extract, phenol red, sodium fluorescein, d-borneol, malachite green, octyldodecyl myristate, methylene blue, medical carbon, riboflavin butyrate, riboflavin, green tea powder, ammonium manganese phosphate, sodium riboflavin phosphate, rose oil, turmeric color, chlorophyll, carminic acid color, Food Red No. 40 and its aluminum lake, water-soluble annatto, sodium iron chlorophyllin, *dunaliella* carotene, *capsicum* color, carrot carotene, potassium norbixin, sodium norbixin, palm oil carotene, beet red, grape pericarp color, black currant color, *monascus* color, safflower red color, safflower yellow color, marigold color, sodium riboflavin phosphate, madder color, alkanet color, aluminum, sweet potato carotene, shrimp color, krill color, orange color, cacao color, cacao carbon black, Japanese persimmon color, crayfish color, carob germ color, fish scale foil, silver, kusagi color, *gardenia* blue, *gardenia* red, *gardenia* yellow, kooroo color, chlorophyllin, kaoliang color, bone carbon black, bamboo grass color, shea nut color, shikon color, sandalwood red, vegetable carbon black, *sappan* color, *spirulina* color, onion color, tamarind color, corn color, tomato color, peanut color, *phaffia* color, pecan nut color, *monascus* yellow, powdered annatto, Haematococcus algae color, purple sweet potato color, purple corn color, purple yam color, vegetable oil soot color, lac color, rutin, enju extract, buckwheat whole-plant extract, logwood color, red cabbage color, red rice color, red radish color, adzuki bean color, *Hydrangea* leaves extract, sepia color, uguisukagura color, elderberry color, olive tea, cowberry color, gooseberry color, cranberry color, salmonberry color, strawberry color, dark sweet cherry color, cherry color, thimbleberry color, European dewberry color, pineapple juice, black huckleberry color, grape juice color, black currant color, blackberry color, plum color, blueberry color, berry juice, boysenberry color, whortleberry color, mulberry color, morello cherry color, raspberry color, red currant color, lemon juice, loganberry color, powdered *chlorella*, cocoa, saffron color, beefsteak plant color, chicory color, laver color, hibiscus color, malt extract, paprika, beet red juice, and carrot juice.

Examples of the light-shielding agent include titanium oxide, iron sesquioxide, yellow ferric oxide, black iron oxide, Food Blue No. 1 aluminum lake, Food Blue No. 2 aluminum lake, Food Yellow No. 4 aluminum lake, Food Yellow No. 5 aluminum lake, Food Green No. 3 aluminum lake, Food Red No. 2 aluminum lake, Food Red No. 3 aluminum lake, Food Red No. 102 aluminum lake, Food Red No. 104 aluminum lake, Food Red No. 105 aluminum lake, Food Red No. 106 aluminum lake, and Food Red No. 40 aluminum lake.

In a pharmaceutical hard capsule, in order to prevent deterioration of the content caused by ultraviolet rays, for example, titanium oxide can be added, in particular, as a light-shielding agent.

The binder includes polyvinyl alcohol. "Polyvinyl alcohol" (PVA) is a polymerization product obtained by saponifying polyvinyl acetate. Usually, there are completely saponified products having a degree of saponification of 97% or more and represented by the following formula (1) and partially saponified products having a degree of saponification of 78 to 96% and represented by the following formula (2). In the present disclosure, both of the above-mentioned completely saponified products and partially saponified products can be used. A partially saponified product having a degree of saponification, n/(n+m), of 78 to 90%, in particular about 87 to 90%, is preferably used although there is no particular limitation.

[Chemical Formula 3]

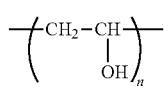
(1)

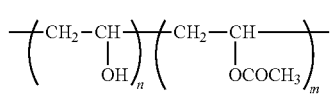
(2)

(wherein n and m each represent an arbitrary integer)

The average degree of polymerization (n) of PVA is not particularly limited as long as it is within a range in which a film forming ability can be exhibited, and is usually 400 to 3300, particularly preferably about 1000 to 3000. The weight-average molecular weight of PVA is not particularly limited although it is about 18000 to about 200000 when calculated from the average degree of polymerization and the degree of saponification described above. The addition of PVA can provide the capsule film with adequate mechanical strength (elastic modulus and crack resistance) with its enteric property maintained.

In the present disclosure, PVA and a PVA copolymer may be used in combination. The PVA copolymer includes a PVA copolymer obtained by copolymerization of the above-mentioned PVA with a polymerizable vinyl monomer. Preferred examples of the PVA copolymer include a macromolecule copolymer obtained by copolymerization of acrylic acid with methyl methacrylate using a partially saponified PVA as described above as a skeleton. Examples of commercially available PVA copolymers include POVACOAT (trademark) series (Nissin Kasei Co., LTD.).

2. Enteric Hard Capsule

A first aspect of the present invention relates to an enteric hard capsule.

Specifically, the enteric hard capsule is an enteric hard capsule composed of a film (a) containing a first component and a second component, or (b) containing a first component and a second component, and further containing at least one component selected from a third component and a fourth component. The first component is methylcellulose and/or hydroxypropyl methylcellulose having a viscosity value of 6 mPa·s or more. The second component is an enteric methacrylic acid copolymer. The third component is a water-insoluble alkyl (meth) acrylate ester copolymer and/or ethyl cellulose. The fourth component is at least one selected from the group consisting of a plasticizer and a surfactant acceptable pharmaceutically or as a food additive. Preferably, the enteric hard capsule is an enteric hard capsule in which the first component is contained at a rate of 30 to 70% by mass and the second component is contained at a rate of 30 to 60% by mass with the sum of the rates of the first component and the second component being 70% by mass or more based on the total mass of the first component, the second component, the third component and the fourth component contained in the film, which is taken as 100% by mass. Among them, the first component primarily helps formation of a film having a capsule shape that is self-supporting without a support, and the second component is a basic component for imparting an enteric function. The third and fourth components contribute to improvement of the mechanical strength and surface flatness on a submicron order of the capsule film.

The water-soluble cellulose compound for use as the first component of the present invention has a viscosity value of 6 mPa·s or more for the following reason.

Conventionally, for hypromellose hard capsules for oral administration that do not depend on pH and are focused on rapid dissolution without delay, water-soluble cellulose having a labeled viscosity (viscosity grade) value of 3 to 15 mPa·s, preferably 3 to 6 mPa·s, is used (Japanese Unexamined Patent Application Publication Nos. Hei 08-208458, 2001-506692, 2010-270039 and 2011-500871). In these, water-soluble cellulose, in particular, HPMC, accounts for almost 100% of the film (in some cases, about 0 to 5% by mass of a gelling agent, a gelation aid, a light-shielding agent, a colorant and so on and about 0 to 10% by mass of residual moisture are contained). In a dissolution test using acetaminophen as an indicator, the dissolving rate of the capsules hardly depends on pH and is determined by the molecular weight of the water-soluble cellulose, that is, the viscosity value thereof. Usually, they are rapidly disintegrating capsules from which 100% of acetaminophen therein is dissolved out within 30 minutes in a test liquid with a pH of 1.2, a test liquid with a pH of 6.8 and pure water. On the other hand, water-soluble cellulose having a viscosity value of 10 mPa·s or more is not virtually used because of its tendency to cause dissolution delay.

In the present invention, mechanical characteristics that are suitable for a hard capsule but cannot be achieved by a methacrylic acid copolymer alone can be achieved by adding a water-soluble cellulose compound having a viscosity value of 6 mPa·s or more, preferably 10 mPa·s or more, more preferably 15 mPa·s or more, in an amount equal to or greater than that of an enteric methacrylic acid copolymer. Although not bound by a theory, it is believed that the water-soluble cellulose compound generally exhibits a function as a filler for a relatively soft or brittle enteric methacrylic acid copolymer. In addition, the water-soluble cellulose compound, which has a relatively high molecular weight, appropriately prevent swelling caused by penetration of moisture and does not impair the acid resistance function of the enteric methacrylic acid copolymer as a primary component. Rather, in the case of a low viscosity value (low molecular weight) grade with a viscosity value of less than 6 mPa·s, dissolution occurs at a pH of 1.2, resulting in insufficient acid resistance performance. Also, the effectiveness as a filler is insufficient and cracks are liable to occur.

On the other hand, in a test liquid with a pH of 6.8, the enteric methacrylic acid copolymer promotes quick dissolution. Thus, dissolution delay is less liable to occur even if the viscosity value is 6 mPa·s or more, even 10m Pa·s or more.

The enteric methacrylic acid copolymer as the second component is preferably at least one selected from the group consisting of a copolymer of methacrylic acid with ethyl acrylate, a copolymer of methacrylic acid with methyl methacrylate and methyl acrylate, and a copolymer of methacrylic acid with ethyl acrylate. More preferably, it is a copolymer composed of 40 to 60% by mass of methacrylic acid and 60 to 40% by mass of ethyl acrylate. The enteric methacrylic acid copolymer hardly dissolves at a pH of about 5 or less and quickly dissolves at a pH of about 5.5 or more.

In the first aspect of the present invention, a water-insoluble alkyl (meth)acrylate ester copolymer and/or ethyl cellulose may be contained as the third component. A water-insoluble alkyl (meth)acrylate ester copolymer, in particular one having a low film forming temperature (glass transition point), binds particles of the enteric methacrylic acid copolymer and promotes formation of a smooth film. On the other hand, its water-insolubility can help to maintain good acid resistance. Ethyl cellulose also can improve the crack resistance of the film and maintain good acid resistance thereof due to its water-insolubility.

In addition, in order to improve mechanical strength, in particular, crack resistance, of the capsule film, at least one selected from the group consisting of a plasticizer and a surfactant (emulsifier) acceptable pharmaceutically or as a food additive may be contained as a fourth component.

When the rates of the first component, the second component, the third component and the fourth component based on the total mass thereof contained in the capsule film according to the first aspect, which is taken as 100% by mass, are defined as $\alpha$, $\beta$, $\gamma$ and $\delta$ (% by mass), respectively ($\alpha+\beta+\gamma+\delta=100$), the rate $\alpha$ of the water-soluble cellulose compound is preferably 30% by mass or more, more preferably 40% or more. When the rate is less than 30% by mass, the capsule film liable to crack. On the other hand, when the rate is more than 70% by mass, it may lead to deterioration of acid resistance at a pH of 1.2 or dissolution delay at a pH of 6.8 (neutral).

When the viscosity value exceeds about 100 mPa·s, if $\alpha$ is more than 30% by mass, the capsule film dissolves slowly even in a buffer solution with a pH of 6.8 and tends to be sustained-release after being transferred into the intestine (takes about 60 minutes or more to reach a dissolution rate of 75% or more). On the other hand, when the capsule film is required to dissolve quickly after being transferred into the intestine, it is preferred to use a water-soluble cellulose compound having a viscosity value of 10 to 100 mPa·s.

The upper limit of the rate α of the water-soluble cellulose compound is preferably 70% by mass, more preferably 60% by mass. When the rate α exceeds 70% by mass, the rare of the second component is inevitably lower than 30% by mass correspondingly and good enteric properties cannot be maintained.

The rate p of the enteric methacrylic acid copolymer as the second component is preferably 30% by mass or more to make the capsule film exhibit sufficient acid resistance as an enteric hard capsule. More preferably, the rare P is 35% by mass or more. On the other hand, in order to maintain appropriate hardness and crack resistance of the capsule film, the upper limit of β is 60% by mass or less, more preferably 50% by mass or less. In the present invention, the first component and the second component are essential, and the rate of the sum of the first component and the second component, i.e., $(\alpha+\beta)/(\alpha+\beta+\gamma+\delta)$, is preferably 70% by mass or more. Because the enteric hard capsule of the present invention has a characteristic fine structure as described later, good acid resistance (enteric properties) can be achieved even when α>β, in particular. More specifically, a composition in which α is 40 to 60% by mass and β is 30 to 50% by mass is more preferred.

The water-insoluble alkyl (meth)acrylate ester copolymer or ethyl cellulose as the third component is preferably 40% by mass or less, preferably 30% by mass or less. The third component also functions as a plasticizer, but is additionally used in place of some of the second component. In other words, γ/β is preferably 0.5 or less, preferably 0.4 or less.

In addition, the rate S of the fourth component contained in the film is 12% by mass or less, preferably 10% by mass or less, more preferably 5% by mass or less. When the fourth component is too much, the enteric properties tend to be impaired. Also, some of plasticizers tend to lower the hardness of capsule films under a high humidity.

In the present invention, a mixture of different types of MC or HPMC having a viscosity value of 6 mPa·s or more may be used, or MC and/or HPMC having different viscosity values may be used in mixture, in which case the total amount of these different types of water-soluble cellulose with a viscosity value of 6 mPa·s can be regarded as the first component and the rate thereof can be taken as α% by mass. In the following, the same applies to the second, third and fourth components. When a plurality of types of enteric methacrylic acid copolymers are used, the total amount thereof is regarded as the second component and the rate thereof is taken as β% by mass. When a plurality of types of water-insoluble alkyl (meth)acrylate ester copolymers and/or ethyl celluloses are used, the total amount thereof is regarded as the third component and the rate thereof is taken as γ% by mass. Regarding the fourth component as well, when a plurality of types of plasticizers and surfactants (emulsifiers) are used simultaneously, the total amount thereof is regarded as the fourth component and the rate thereof is taken as δ% by mass.

The enteric hard capsule film of the present disclosure may further contain a lubricant, a metal sequestering agent, a coloring agent, a light-shielding agent, a binder and so on in an amount of about 5% by mass.

In the capsule film of the present invention, the presence of a salt resulting from neutralization of the enteric methacrylic acid copolymer, and the presence of neutralization products of other film components associated therewith may be allowed. In other words, some of the enteric methacrylic acid copolymer may be present in the capsule film as a salt acceptable pharmaceutically or as a food additive. The salt is at least one selected from the group consisting of alkaline metal salts, alkaline-earth metal salts, and ammonium salts. Preferably, the salt is at least one salt selected from the group consisting of sodium salts and ammonium salts. An Na salt is particularly preferred. Specifically, the carboxyl groups of the enteric methacrylic acid copolymer are neutralized by ions of a metal such as Na and can be present stably as groups such as —COONa in the solid film. The rate of these neutralized acid (such as carboxylic acid) residues is preferably 20% or less, more preferably 15% or less, still more preferably 10% or less, for example, based on the number of moles (the number of groups) of the carboxyl residues contained in the enteric methacrylic acid copolymer before neutralization, which is taken as 100%. This is referred to as degree of neutralization (the detailed definition of degree of neutralization is described in Aspect 2). The presence of excessive salt is not preferred because it makes the film have a tendency to crack, or undergo deterioration due to salt precipitation or disintegration due to excessive permeation of water. On the other hand, the presence of an appropriate amount of salt helps water to permeate into and swell the capsule film containing the enteric methacrylic acid copolymer. The swelling of the capsule film is effective in closing the gap between the cap and the body to prevent dissolution thereof more completely. For this purpose, the degree of neutralization is preferably 2% or more, more preferably 5% or more. As a result, the salt contained in the capsule film is preferably 0.2% by mass or more, more preferably 0.5% by mass, in terms of its hydroxide (in the case of an Na salt, the mass of NaOH) based on the weight of the film. On the other hand, the salt is preferably 2% by mass or less, more preferably 1.5% by mass or less.

In order for the capsule film of the present disclosure to have appropriate plasticity and maintain crack resistance, the capsule film preferably contain 2 to 10% by mass of residual moisture (contained moisture). Usually, when the molded capsule is subjected to a drying treatment at a temperature in the range of 30° C. to 100° C., a predetermined saturated residual moisture value is reached. Naturally, the time before the saturation moisture value is reached is shorter when the dry treatment is carried out at a higher temperature. The residual moisture changes almost reversibly although it also depends on the environmental humidity at the time of storage of the capsule. In other words, the residual moisture value after a sufficient dry treatment at 30 to 100° C. converges to a certain saturation moisture value when the capsule is stored for several days at constant temperature and relative humidity. In the present invention, a saturation moisture value after storage for several days at room temperature and a relative humidity of 43% is used.

The saturation moisture value (moisture content) as the residual moisture in the film at room temperature and a relative humidity of 43% is preferably at least 2% or more, more preferably 3% or more, still more preferably 4% or more, based on the total mass of the capsule film. On the other hand, saturation moisture value is preferably 10% or less, more preferably 8% or less, still more preferably 6% or less because moisture may react with the drug filled in the capsule if the moisture content is too much when the capsule is stored for a long period time.

The saturation moisture amount can be represented by the percentage of water content at loss on drying and its measurement can be made as follows.

<Method for Measuring Moisture Content in Capsule Film by Loss-On-Drying Method>

A potassium carbonate saturated salt is placed in a desiccator to create a constant-humidity atmosphere therein, and a sample (hard capsule or film) is placed in the desiccator. Then, the desiccator is sealed and subjected to humidity conditioning at 25° C. for one week. For the humidity conditioning, the following saturated salts (aqueous solutions) are used. In other words, in the presence of a potassium acetate saturated salt, a potassium carbonate saturated salt and an ammonium nitrate saturated salt, atmospheres with a relative humidity of about 22%, 43% and 63%, respectively, can be created. After the mass (wet mass) of the sample after the humidity conditioning is measured, the sample is then dried by heating at 105° C. for two hours, and the mass (dry mass) of the sample is measured again. From the difference between the mass before drying (wet mass) and the mass after drying (dry mass), the rate of the amount of moisture decreased during the drying by heating at 105° C. for two hours (water content) is calculated according to the following equation, and is defined as water content (% by mass).

[Mathematical Formula 1]

$$\text{Water content (\%)} = \frac{\text{(Wet mass of sample)} - \text{(Dry mass of sample)}}{\text{Wet mass of sample}} \times 100$$

It is desired that the enteric hard capsule according to the present invention has a shape and mechanical strength (hardness and crack resistance) identical or similar to those of commercially available conventional hard capsules intended for oral administration to a human or animal subject. A commercially available hard capsule to be referenced is a gelatin or HPMC (hypromellose) capsule. Thus, the capsule film has a thickness of 50 µm or more, preferably 60 µm or more, more preferably 70 µm or more. On the other hand, the upper limit thereof is 250 µm or less, preferably 200 µm or less, more preferably 150 µm or less. In particular, the range of 70 to 150 µm is suitable for direct use in a commercially available filling machine. The capsule film is required to have such a thickness and mechanical strength equivalent to that of a commercially available hard capsule film. The mechanical strength can be evaluated by a "tensile strength test" that is usually applied to a polymer using a film prepared in a strip shape (Non-Patent Document 1, Chapter 4).

When mechanical strength of a hard capsule film is evaluated, it is important to compare test films having the same thickness. Thus, the mechanical strength of a film, which depends on the component composition of the hard capsule, can be evaluated using a cast film fabricated by a casting method using a preparation liquid having the same component composition as the component composition of the hard capsule preparation liquid.

The cast film is fabricated by placing a metal applicator on a surface of a glass or PET film held at room temperature, casting a preparation liquid at 50° C. to 60° C. and moving the metal applicator at a constant speed to form a uniform film with a thickness of 100 µm. After that, the film is dried at a temperature of room temperature to 30° C. for about ten hours.

In order to obtain a film with a uniform thickness of 100 µm, applicators having gaps ranging from 0.4 mm to 1.5 mm may be used appropriately.

Figure 5:
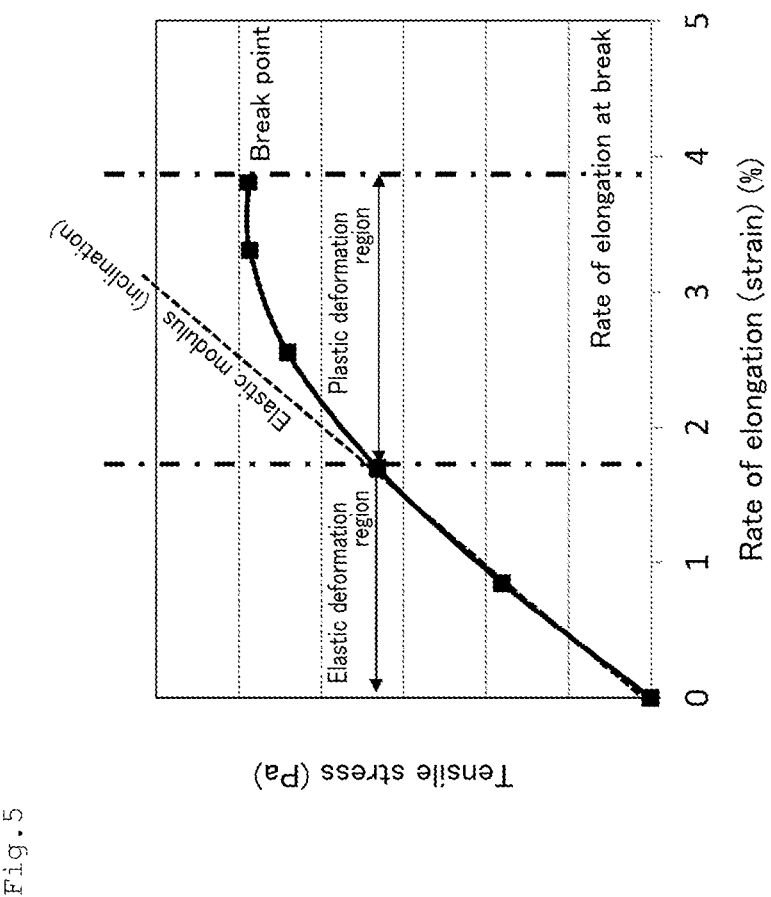
FIG. 5 shows an example of a typical tensile stress-rate of elongation (strain, %) curve in a tensile test, and explanation of elastic modulus (Young's modulus) and rate of elongation at break. The elastic modulus on the vertical axis indicates an inclination in a low-stress elastic region. Also, the rate of elongation at break on the horizontal axis is the rate of elongation (strain), %, at which the test piece breaks.

The fabricated film can be subjected to a tensile test using, for example, a compact tabletop tester (EZ-LX from Simadzu Corporation) after being cut into a dumbbell shape of 5 mm×75 mm (specified in JIS K-7161-2-1BA), for example. Specifically, both ends of the film are set on a holder (gap length 60 mm), and the film is pulled at a tension rate of 10 mm/min to show the elongation of the film and a curve showing the relation between the stress (tensile stress) that occurs in the film and the rate of elongation (strain). FIG. 5 shows a typical elongation-tensile stress test result. From the inclination in the elastic deformation region under low stress in the drawing, an elastic modulus that is an indicator of hardness can be obtained and a rate of elongation at break (%), which is the rate of elongation at the break point, can be obtained (Non-Patent Document 1, Chapter 4). When the film thickness is in the range of 100 µm±50 µm, the elastic modulus is obtained by standardizing to a film thickness value of 100 µm as being approximately proportional to the film thickness. It may be believed that the rate of elongation at break hardly depends on the film thickness when the film thickness is in this range.

It is desired that the above-mentioned mechanical strength is maintained in an environment under normal use conditions (temperature of about 5 to 30° C. and a relative humidity of about 20 to 60%). For example, a tensile test can be conducted to evaluate the mechanical strength after the fabricated film is subjected to humidity conditioning for one week or longer under humidity conditioning conditions at 25° C. and a relative humidity of 22% (potassium acetate saturated salt is used). The tensile test is preferably conducted in an environment with a temperature of 25° C. and a relative humidity of 22%.

The elastic modulus (Young's modulus), which is an indicator of hardness, is preferably 1 to 5 GPa, more preferably 2 to 5 GPa. The rate of elongation at break, which is an indicator of crack resistance evaluated by a tensile test, is preferably about 2 to 30%, more preferably about 3 to 20%. Usually, the hardness and crack resistance of the enteric hard capsule film of the present invention are often in a trade-off relationship in these ranges. Coating films or soft capsule films are often softer and have a larger rate of elongation at break. For example, a film having a rate of elongation at break of more than 30% is usually too soft in many cases to be suitable as a self-supporting hard capsule film. With regard to the hardness of the enteric hard capsule of the present invention, an elastic modulus in the range of 1 to 5 GPa, even 2 GPa or more, can be obtained in almost the entire relative humidity and temperature ranges in a room condition. On the other hand, the moisture present in the capsule film in an amount of about several % as described above may usually influence on the mechanical strength, in particular cracking properties, as a plasticizer. Under use and storage conditions with a low relative humidity, the capsule film has a tendency to crack easily when the water content is decreased to about 2 to 3%, for example. Usually, when the rate of elongation at break falls below 2%, the capsule is prominently liable to crack easily even under normal handling conditions. In the present invention, humidity conditioning and tensile tests are conducted, in particular, in an environment with a relatively low humidity of 22% and a temperature of 25° C. so that a film having a rate of elongation at break of 2 to 30%, even 3% or more, can be obtained.

The enteric hard capsule film according to the first aspect exhibits a multiphase structure separated into a phase composed primary of a water-soluble cellulose compound and a phase composed substantially of other components. This structure referred to as sea-island structure with the phases composed primary of a water-soluble cellulose compound being regarded as "island" phases and the phase composed substantially of other components being regarded as a "sea" phase. The island phases are phases composed substantially of core particles of the first component. Here, "substantially" means that the island phases may contain a trace amount of other components that having entered therein and, on the other hand, the sea phase may contain the first component, which is partially dissolved therein. Also, the sea phase may contain a methacrylic acid copolymer as the second component, a plasticizer, a light-shielding agent, a pigment, a colorant, a lubricant and so on. The island portions are not necessarily surrounded by the seas and isolated, and the capsule film may have a lamellar structure in which islands or seas are connected to each other. This can be taken as a two-phase structure on the order of μm or more. As shown in later in Examples, the "sea-island structure" can be confirmed by observing a transverse cross-section of the hard capsule film under a scanning electron microscope or the like. Also, the distributed state of each component in the islands or sea can be estimated by observation under a Raman microscope or the like.

In the present disclosure, the content α of the first component is 30 to 70% by mass and the content β of the enteric methacrylic acid copolymer as the second component is 30 to 60% by mass, in particular. It is presumed that sufficient enteric properties can be ensured even if the amount of the second component is relatively small because the core particles of the first component are covered with the molecules or colloidal particles of the second component. In other words, it is presumed that the core particles of the first component with a size on the order of 1 μm to 10 μm are each individually coated with an enteric coating and aggregated to form a film structure.

Such a multiphase, that is, "sea-island structure" cannot be formed without a kind of quasi-equilibrium state of a fluid dispersion in a solution state as described later. It is, therefore, presumed difficult to form such a sea-island structure by injection molding or extrusion molding utilizing the thermoplasticity of a film component polymer. It is also presumed difficult to form such a sea-island structure when the first component is once dissolved and then formed into a film through a hot gelation process.

The size of each island phase depends on the size of the solid fine particles of the water-soluble cellulose compound used for the preparation of the hard capsule. Usually, the minor axis extends in the thickness direction of the film, and is preferably ⅓ or less, more preferably ¼ or less, of the film thickness. The island phases in the hard capsule film preferably have a minor axis with a length of 0.1 μm or more and less than 30 μm. More preferably, the island phases have a minor axis with a length of 0.2 μm or more and less than 20 μm. To realize the size of the island phases, the dry ingredient powder of the water-soluble cellulose polymer (methylcellulose/hydroxypropyl methylcellulose) preferably has an average particle size of 1 to 100 μm. In the present disclosure, a laser diffraction method is used in which a particle is irradiated with a laser beam and a particle size of an equivalent sphere is obtained from a scattering pattern obtained therefrom. In particular, the volume fraction of the powder with a particle size of 100 μm or more is preferably less than 50%, more preferably less than 40%.

The laser diffraction method and the definitions of the particle size, average particle size, volume fraction and so on obtained by this method are in accordance with JIS Z 8825.

3. Enteric Hard Capsule Preparation Liquid and Method for Preparation Thereof

A second aspect of the present invention relates to a preparation liquid for preparing an enteric hard capsule (also referred to simply as "preparation liquid") as described in the above section 2. The hard enteric capsule of the present invention is composed of a film obtained by drying the preparation liquid of this aspect to remove a solvent therefrom.

Specifically, the second aspect relates to an enteric hard capsule preparation liquid containing a component i, which is methylcellulose and/or hydroxypropyl methylcellulose having a "viscosity value" of 6 mPa·s or more when in the form of a 2% aqueous solution at 20° C., a component ii, which is an enteric methacrylic acid copolymer, a basic neutralizing agent and a solvent.

Here, the solvent for use in the preparation liquid is preferably composed primarily of water, and, in particular, is purified water. However, in a dissolution process for obtaining a fluid dispersion from a solid powder of the water-soluble cellulose compound and/or the enteric methacrylic acid copolymer, a mixed solvent of water and at least one selected from ethanol and anhydrous ethanol may be used. During the preparation of the preparation liquid or a dipping step of the present invention, the ethanol is mostly evaporated. Thus, the preparation liquid during dipping actually has a moisture content of 80% by mass, more preferably 90% by mass or more. It is preferred to use a substantially 100% purified water excluding inevitably contained impurities.

As described above, in the case of the methylcellulose and hydroxypropyl methylcellulose for the component i, when undissolved fine particles (usually 1 to 100 μm in diameter) of the water-soluble cellulose are dissolved in water, if the particles are first dispersed at a cloud point TO (lower critical solution temperature) or above and the water temperature is then decreased to dissolve the particles, the fine particles gradually starts dissolving from the surfaces and swell. However, the particles do not dissolve completely and maintain a state in which the (swollen) solid fine particles are dispersed at about 30° C. or above. In other words, a fluid dispersion (suspension) is formed. When the temperature of the fluid dispersion is maintained in the range of 30 to 60° C. with stirring, the dispersed state remains stable for at least several days.

More preferably, it is preferred to use, as the component ii, a colloidal dispersion of an enteric methacrylic acid copolymer from which an aqueous emulsion containing very small colloidal particles having a diameter of more than about 0.01 μm and less than 1 μm is first formed through a copolymerization process in an aqueous solution from a monomer level by an emulsion polymerization process. As a result, a fluid dispersion of very fine colloidal particles having an average particle size of less than 1 μm can be obtained without a dissolution step by neutralization of the solid polymer component with a basic neutralizing agent. Alternatively, when an enteric methacrylic acid copolymer in the form of a solid powder obtained by evaporating to dryness the moisture of an aqueous emulsion produced by emulsion polymerization to extract only the solid content thereof is used, an aqueous dispersion can be obtained again by partially neutralizing it with a basic neutralizing agent in water.

The basic neutralizing agent is not particularly limited as long as it is a compound acceptable pharmaceutically or as a food additive. The basic neutralizing agent is at least one selected from the group consisting of alkaline metal salts, alkaline-earth metal salts, and ammonium salts. Preferably, the basic neutralizing agent is at least one metal hydroxide selected from the group consisting of sodium hydroxide, potassium hydroxide, calcium hydroxide, and magnesium hydroxide. More preferably, the basic neutralizing agent is sodium hydroxide.

In place of or in addition to these metal hydroxides or ammonia, disodium hydrogen phosphate ($Na_2HPO_4$), disodium sulfite ($Na_2SO_3$), trisodium citrate dihydrate ($C_6H_5Na_3O_7 \cdot 2H_2O$), calcium gluconate monohydrate ($C_{12}H_{22}CaO_{14} \cdot H_2O$), Disodium DL-malate n-hydrate ($NaOOCCH(OH)CH_2CONa \cdot nH_2O$) and the like can be also used as the salts. Among them, disodium hydrogen phosphate, disodium sulfite, and trisodium citrate are preferred, and disodium hydrogen phosphate is particularly preferred.

When the basic neutralizing agent is ammonia or ammonium carbonate, it is preferred to volatilize ammonia to remove the salt in the film as much as possible after the film formation.

The equivalent for complete neutralization of the component ii and the degree of neutralization thereof can be defined as follows.

Complete neutralization of the component ii is achieved by adding the basic neutralizing agent in such an amount that positive ions derived from the basic neutralizing agent are equivalent or more to one mole of carboxyl groups contained in the component ii. When the positive ions derived from the basic neutralizing agent are divalent or more, the amount is replaced with 1/valence. Complete neutralization refers to a case where the component iii and a basic neutralizing agent are dissolved in a solvent such that the positive ions derived from the basic neutralizing agent is substantially equivalent in amount to the carboxyl groups contained in the component ii. The number of moles of the equivalent positive ions, that is, "equivalent (equimolar amount)" refers to the number of moles of positive ion in such an amount that 100% of the number of moles (the number of groups) of carboxyl residues before neutralization contained in the enteric methacrylic acid copolymer can be blocked by neutralization, for example.

Specifically, it can be defined as the mass of KOH (molecular weight 56.10) necessary to neutralize Ig of an intended enteric methacrylic acid copolymer, that is, (KOH) mg/g (KOH equivalent). Also, the degree of neutralization is defined as the ratio of the mass of the basic neutralizing agent actually added to the equivalent of a basic neutralizing agent necessary for complete neutralization. The equivalent in the case where the basic neutralizing agent is sodium hydroxide NaOH (molecular weight 40.00), calcium hydroxide $Ca(OH)_2$ (molecular weight 74.09), ammonia $NH_3$ (molecular weight 17.03), or ammonium carbonate $(NH_4)_2CO_3$ (molecular weight 96.09) is obtained by conversion through the use of the following formula:

[(KOH equivalent)×(Molecular weight of basic neutralizing agent/valence)]/(KOH molecular weight)    [Mathematical Formula 2]

Usually, the equivalent of a basic neutralizing agent necessary for complete neutralization may be labeled by the manufacturer with a margin of about +10 to 20% as an acceptable range of the degree of substitution of carboxyl groups.

For example, when the component ii is Eudragit. L30D-55 or L100-55 manufactured by Evonik Industries AG, the KOH equivalent thereof is labeled as 301.2 mg/g. When the basic neutralizing agent is sodium hydroxide, the KOH equivalent is 214.8 mg/g. Also, when the basic neutralizing agent is ammonia, the KOH equivalent is 91.4 mg/g. When the component ii is Eudragit. FS30D manufactured by Evonik Industries AG, the KOH equivalent thereof is 56.7 mg/g. When the basic neutralizing agent is sodium hydroxide, the KOH equivalent is 40.4 mg/g. When the basic neutralizing agent is ammonia, the KOH equivalent is 17.2 mg/g. A more accurate neutralization equivalent can be determined by a general titration method.

The degree of neutralization is defined as the mass ratio of the basic neutralizing agent actually added to the amount of basic neutralizing agent corresponding to the neutralization equivalent;

Degree of neutralization (%)=(Mass of basic neutralizing agent added)/{(Neutralization equivalent, mass)×Mass of enteric polymer}×100    [Mathematical Formula 3]

For example, when E mg of NaOH is used for r g of the enteric methacrylic acid copolymer, L30D-55, the degree of neutralization is E/(241.8×Γ)×100(%). At the same time, the degree of neutralization is equal to the number of moles of carboxylic acid residues blocked through neutralization out of the number of moles of the residues.

Two or more types of basic neutralizing agents may be used in combination, in which case the sum of the degrees of neutralizations of individual neutralizing agents is regarded as the degree of neutralization. For example, when NaOH is added to L30D-55 such that the degree of neutralization corresponds to 8% and $Na_2HPO_4$ (KOH equivalent, 316 mg/g) is further added such that the degree of neutralization corresponds to 6%, the degree of neutralization as a whole can be regarded as 14%.

In the present invention, a colloidal dispersion of L30D-55, which is an example of the enteric methacrylic acid copolymer, has a pH of about 2 to 3, and has a pH in the range of 5 to 6 after partial neutralization.

When an enteric methacrylic acid copolymer provided as an aqueous dispersion (latex) that has been formed into colloidal particles in advance by emulsion polymerization is used, the basic neutralizing agent is further used not for further dissolution or refinement of colloid in the colloidal dispersion of the component ii but for realizing stability of the mixed fluid dispersion with the component i as described later. Thus, the basic neutralizing agent is sufficient in a small amount. The amount to be added may be at most 20% or less, preferably 15% or less in terms of the degree of neutralization for the enteric methacrylic acid copolymer. As a result, the pH of the capsule preparation liquid reaches the range of about 5 to 6.

In addition to the component i, the component ii and the basic neutralizing agent, a water-insoluble alkyl (meth) acrylate ester copolymer may be added as a component iii. A fluid dispersion of colloidal particles thereof is preferred. Some water-insoluble alkyl (meth)acrylate ester copolymers can be directly formed into a fluid dispersion of colloidal particles by an emulsion polymerization process. These are preferred because they are stable in a dispersed state and a stable aqueous dispersion can be obtained.

In addition, a plasticizer and a surfactant (emulsifier) acceptable pharmaceutically and as a food additive as described above may be contained as a component iv. The plasticizer and surfactant (emulsifier) acceptable pharmaceutically and as a food additive are also effective in adjusting the viscosity (reducing the viscosity) of the capsule preparation liquid and improving its stability in a dispersed state.

When the rates of the component i, the component ii, the component iii and the component iv contained in the enteric hard capsule preparation liquid based on the total mass thereof, which is taken as 100% by mass, are defined as $\alpha'$, $\beta'$, $\gamma'$ and $\delta'$% by mass, respectively ($\alpha'+\beta'+\gamma'+\delta'=100$), these rates are virtually equal to the rates $\alpha$, $\beta$, $\gamma$ and $\delta$, respectively, of the respective components in the hard capsule film obtained by dipping into a preparation liquid and subsequent drying. Thus, component rates preferred for the capsule film may be applied. Here, the mass of each component is the mass of the polymer component and does not include the mass of the solvent component when a fluid dispersion is used.

Also, the rate of the salt (Na, K, Ca, etc.) remaining in the capsule film after drying substantially corresponds to the degree of neutralization in the preparation liquid. In other words, almost the entire amount of the salt is incorporated into the film. Generally, dissolution at pH 1.2 is reduced by the effect of the remaining salt but dissolution at an intermediate pH of about 4 tends to increase. From this viewpoint as well, the degree of neutralization of the methacrylic acid copolymer is preferably to 20% or less.

Also, the total mass of the polymer components, i.e., the component i, the component ii, the component iii and the component iv, contained in the enteric hard capsule preparation liquid is not limited as long as a hard capsule preparation liquid can be prepared. Preferably, the rate of the total mass of the polymer components, i.e., the component i, the component ii, the component iii and the component iv (polymer component concentration), is preferably 10 to 30% by mass, more preferably 12 to 25% by mass based on the enteric hard capsule preparation liquid, which is taken as 100% by mass. When the rate the total mass of the polymer components, i.e., the component i, the component ii, the component iii and the component iv, is less than 10% by mass, dripping is liable to occur during drying because drying takes a very long time.

In particular, the concentration of the polymer components of the component i and the component ii (solid content) is preferably 7 to 20% by mass. Also, the concentration of the basic neutralizing agent in the capsule preparation liquid is preferably 0.02 to 0.7% by mass, more preferably 0.05 to 0.5% by mass.

In addition, when a lubricant, a metal sequestering agent, a coloring agent, a light-shielding agent and so on are contained, the sum of these is preferably 2% by mass or less, more preferably 1% by mass or less based on the enteric hard capsule preparation liquid, which is taken as 100% by mass.

Usually, dissolved or dispersed polymer components other than the components i to iv, i.e., components such as a light-shielding agent, and the basic neutralizing agent remain present in the capsule film with their component rates substantially maintained. In addition to those, some of moisture in the solvent remains in the film as described above.

In the present invention, it has been found, with regard to an enteric hard capsule preparation liquid containing a water-soluble cellulose compound at least partially dissolved therein and an enteric methacrylic acid copolymer dispersed therein, each of which have no cold gelation ability on its own, that it is possible to impart a cold gelation ability to the enteric hard capsule preparation liquid by mixing the above-mentioned two components. In particular, it has been found that the interaction between a high-concentration water-soluble cellulose compound as the component i and an enteric methacrylic acid copolymer as the component ii in the presence of an appropriate amount of a basic neutralizing agent is important. The enteric hard capsule preparation liquid of the present invention is preferably an enteric hard capsule preparation liquid that exhibits an abrupt increase in storage modulus and loss elastic modulus preferably at a fourth temperature T4 (temperature at which an abrupt increase in viscosity starts) below a second temperature T2 or a third temperature T3, and turns into a gel state, in other words, has a storage elastic modulus G' higher than a loss elastic modulus G" at around room temperature when the temperature is decreased from a temperature below the cloud point TO (cloud point or dissolution start temperature) of the water-soluble cellulose compound as the component i as shown in FIG. 1. What is important is that the relationship storage elastic modulus G'>loss elastic modulus G" is established at around room temperature with a large amount of moisture that has been hardly dried yet contained. The magnitude relationship between G' and G" from T0 to T4 is not particularly limited but it is preferred that G' is substantially equal to or smaller than G".

The abrupt increase in viscosity at around T4 during the process of cooling the capsule preparation liquid of the present invention does not usually occur in an aqueous solution of the component ii (a colloidal dispersion thereof), the component iii (a colloidal dispersion thereof), or the component iv alone, or in a mixed solution of the component ii, the component iii and the component iv. It is presumed that the abrupt increase in viscosity at around T4 is primarily caused by the structural viscosity due to the interaction between the dispersed fine particles of the partially dissolved water-soluble cellulose compound as the component i. The fact that the first component has a lower critical solution temperature is suitable for obtaining such a fluid dispersion. In particular, by the effect of the high-viscosity (that is, high-molecular weight) water-soluble cellulose compound used in the present invention, the viscosity has a pronounced tendency to increase abruptly by one digit or more in the temperature range T4 of about 30 to 60° C. during the cooling process. In order to utilize such an abrupt increase in viscosity during a temperature decrease, the rate $\alpha'$ of the component i contained in the preparation liquid is preferably 30% by mass or more and 70% by mass or less. The viscosity tends to increase slowly when the rate is less than 30% by mass (particularly when the viscosity value is less than 10 mPa·s), and the viscosity tends to be so high as to make molding by a dipping method as described later difficult when the rate is more than 70% by mass (particularly when the viscosity value is more than 100 mPa·s).

In order to achieve the cold gelation characteristics due to which the preparation liquid turns into a gel state, in other words, has the relationship storage elastic modulus G'>loss elastic modulus G", at least at around room temperature, the interaction between the component ii and the component i, both having a relatively high-concentration, is important. In fact, with the component i alone, the formed fluid dispersion exhibits an abrupt increase in viscosity due to structural viscosity in the temperature decreasing process but dissolution of the component i proceeds until the undissolved fine particles are all dissolved and the structural viscosity disappears when the temperature is further decreased to about 30° C. or lower. In other words, there is obtained a mere polymer solution with G'<G". The present inventors have found that the simultaneous presence of the component i and the component ii allows undissolved fine particles of component i to be present stably even at around room temperature. This is presumed to result in the cold gelation with G'>G".

The component i and the component ii are essential, and the rate of the sum of the components $(\alpha'+\beta')/(\alpha'+\beta'+\gamma'+\delta')$ is preferably 70% by mass or more. Also, in order to maintain the strength of the gel provided by the interaction between the component i and the component ii, it is preferred that the composition ratios of $\alpha'$ and $\beta'$ are not significantly different from each other. A composition in which $\alpha'$ is 30 to 60% by mass and $\beta$ is 30 to 60% by mass is preferred, and it is preferred, in particular, that $\alpha'$ is in the range of 40 to 60% by mass and $\beta'$ is in the range of 30 to 50% by mass.

As the component ii, the number of methacrylic acid monomer units in the copolymer is preferably 20% or more, more preferably 30% or more. More specifically, a copolymer composed of 40 to 60% by mass of methacrylic acid and 60 to 40% by mass of ethyl acrylate is preferred. The cold gelation less liable to occur when the rate of methacrylic acid monomer units is less than 20% by mass. Alternatively, it is desirable that methacrylic acid monomer units account for 6% by mass or more of the total mass $(\alpha'+\beta'+\gamma'+\delta')$.

In addition, the concentration of the component i in the preparation liquid is preferably 5% by mass or more, more preferably 10% by mass or more. When the concentration of the component i is low, the preparation liquid less liable to exhibit an abrupt increase in viscosity during the temperature decreasing process. On the other hand, in order for the viscosity of the preparation liquid at a temperature between TO and T4 to be suitable for molding of a capsule film by a dipping method, the concentration of the component i in the preparation liquid is preferably 20% by mass or less, preferably 15% by mass or less.

The cold gelation characteristics as shown in FIG. 1 are regarded as undesirable in coating such as spray coating because the gelation product causes clogging of the spraying nozzle and the like. Thus, a water-soluble cellulose compound and an enteric methacrylic acid copolymer, both having a high concentration and a viscosity of 6 mPa·s or more, are not usually combined selectively.

On the other hand, when the component i and the component ii are directly mixed with no basic neutralizing agent present in the solvent, the mixture immediately gelates and condenses. Thus, attentions must be paid regarding the preparation method as described later.

In other words, a third aspect of the present invention relates to a method for preparing an enteric hard capsule preparation liquid according to the second aspect.

Specifically, the third aspect relates to a method for preparing an enteric hard capsule preparation liquid, including mixing a component i and a component ii under a condition in which a basic neutralizing agent is present in a solvent. The component i is methylcellulose and/or hydroxypropyl methylcellulose having a viscosity value of 6 mPa·s or more, and the component ii is an enteric methacrylic acid copolymer. With regard to the enteric methacrylic acid copolymer, it is preferred to use a colloidal dispersion thereof.

As described above, in order to achieve an abrupt increase in viscosity and a cold gelation at around room temperature during a temperature decreasing process, it is important to use the water-soluble cellulose compound having a viscosity value in the range of 6 mPa·s or more as the component i and the enteric methacrylic acid copolymer as the component ii in combination. However, usually, when these are directly mixed with each other, aggregation occurs immediately and stable fluid dispersion may not be obtained. Thus, these must be mixed under a condition in which a basic neutralizing agent is present in the solvent. For this purpose, the degree of neutralization for the component ii is preferably 2% or more, more preferably 5% or more. On the other hand, because excessive neutralization inhibits cold gelation, the degree of neutralization is preferably 20% or less, more preferably 1% or less, still more preferably 10% or less. Although not bound by a theory, it is presumed that the interaction between colloidal particles of the enteric methacrylic acid copolymer and/or the interaction between carboxyl groups of the methacrylic acid contained in the enteric methacrylic acid copolymer and the hydroxyl groups of the water-soluble cellulose are involved in the aggregation phenomenon and the cold gelation phenomenon as described above.

More specifically, the third aspect includes the following aspect 3-1.

The aspect 3-1 according to the present invention relates to a method for preparing an enteric hard capsule preparation liquid containing a film component and a solvent, the method including:
  a step A: a step of providing a partially neutralized solution of a component ii, and
  a step B: a step of adding a component i to the partially neutralized solution of the component ii to provide a partially dissolved solution of the component i.

In each step, each component may be added to the solvent, or the component may be added to or mixed with a solution prepared in a previous step and already containing other components. A transition temperature between the respective steps, or the temperature regulation in mixing the solutions prepared in each step may be set as appropriate in accordance with the following requirements.

With regard to the methacrylic acid copolymer as the component ii, it is preferred to use a colloidal dispersion that can dispense with an additional dispersing step by neutralization. However, in order to prevent undesirable aggregation and precipitation caused by mixing with the component i or a partially dissolved dispersion of the component i to stabilize the dispersed state of the capsule preparation liquid, it is preferred to mix the component ii with the component i in the presence of a minimum basic neutralizing agent.

Thus, in the step A, a partially neutralized solution of the component ii is prepared by adding a basic neutralizing agent acceptable pharmaceutically or as a food additive in advance to the component ii, and the degree of neutralization thereof is preferably as relatively low as 2% or more, more preferably 5% or more. On the other hand, the degree of neutralization is preferably 20% or less, more preferably 18% or less, still more preferably 12% or less. When the degree of neutralization is excessively less than this, aggregation occurs immediately after the component i and the component ii are mixed, and a stable aqueous dispersion cannot be obtained. On the other hand, the degree of neutralization is too high, the cold gelation performance of the capsule preparation liquid tends to be impaired.

The optimum range can be adjusted by adjusting the composition ratio between the methacrylic acid monomer units and other alkyl (meth)acrylate ester monomer units in the methacrylic acid copolymer or the solid content concentration in the capsule preparation liquid. Specifically, when the component ii is a copolymer composed of 40 to 60% by mass of methacrylic acid and 60 to 40% by mass ethyl acrylate (more specifically, L30D-55), an adequate degree of neutralization is 2 to 20%.

After that, in the step B, the component i is added to the solution containing the basic neutralizing agent and the component ii to prepare a partially dissolved solution of the component i. The component i is added to the neutralized solution containing the component ii or a fluid mixture of the neutralized solution of the component ii and a fluid dispersion of the component iv at a first temperature T1 equal to or higher than the cloud point T0 of the component i to prepare a fluid dispersion in which the component i is partially dissolved at a second temperature T2 lower than the cloud point.

In the aspect 3-1, the first temperature T1 is equal to or higher than the cloud point T0, and is not limited as long as it is a temperature lower than the boiling point of the solvent. For example, the first temperature T1 can be in the range of 60° C. to 90° C. Preferably, the temperature T1 can be in the range of 70° C. to 90° C.

In the aspect 3-1, the second temperature T2 is preferably higher than room temperature (20° C. to 25° C.) and lower than the cloud point T0. For example, the second temperature T2 can be in the range of 30° C. to 60° C. Preferably, the temperature T2 can be in the range of 40° C. to 60° C.

In the aspect 3-1, the viscosity of the fluid dispersion in which the water-soluble cellulose compound is dispersed in an undissolved state at a temperature equal to or higher than T0 is very low and approximately less than 100 mPa·s. When the water-soluble cellulose compound starts dissolving, the viscosity gradually increases to reach a viscosity higher than 100 mPa·s, indicating that the fluid dispersion has passed T0 in the temperature decreasing process. A fluid dispersion in which undissolved solid fine particles of the water-soluble cellulose are stably present can be obtained within about 10° C. from T0. When the temperature is further decreased, the viscosity continues to show one- to two-digit abrupt increase until the viscosity reaches 1000 mPa·s or more. Further, when the temperature approaches room temperature, the solid fine particles of the water-soluble cellulose compound are dissolved almost entirely with the high viscosity is substantially maintained. When the water-soluble cellulose compound is dissolved almost completely in the solvent, the sea-island structure of the capsule film cannot be kept. Also, because the capsule preparation liquid has too high a viscosity (approximately 10,000 mPa·s or more), it is preferred that the temperature T2 is equal to or lower than T0 and does not fall below 30° C.

As described above, by suspending the water-soluble cellulose compound as the component i in a neutralized solution of the component iii at the temperature T1, which is equal to or higher than the cloud point T0, and decreasing the temperature to the second temperature T2, a fluid dispersion in which the component i is partially dissolved can be prepared. Because the dissolution proceeds more as the temperature difference between T0 and T2 is larger, the degree of partial dissolution can be controlled as appropriate using the temperature difference.

In the preparation liquid of the present invention and the process for preparing a preparation liquid of the present invention, a step C of adding a component iii may be added in the step A or step B. An alkyl(meth)acrylate ester copolymer as the component iii hardly has interaction that affects the viscosity or chemical stability with either the component i or the component ii and can be added as a water dispersion subsequently to either the step A or step B.

In addition, the aspect 3-1 may further include a step D of maintaining the solution obtained in the step B or C at a third temperature T3 lower than the cloud point of the component i. Also, the third temperature T3 is preferably higher than T2 and not lower than the cloud point T0 by 10° C. or more. As a result, the partially dissolved state of the component i can be kept stably. For example, the temperature T3 can be in the range of 30° C. to 60° C. Preferably, the temperature T3 can be in the range of 50° C. to 60° C.

The component iv of the preparation liquid of the present invention can be usually added subsequent to any of the steps B. C and D.

In addition, it is desirable to conduct stirring continuously in all the steps of the preparation in the aspect 3. For example, when the preparation process is performed in a cylindrical container, it is preferred to achieve stirring by rotating a propeller-shaped stirring blades at 1 to several hundred rpm.

The viscosity of the capsule preparation liquid can be adjusted mainly by adjusting the viscosity value and concentration of the component i and also by adjusting the degree of partial dissolution thereof. In other words, the viscosity can be adjusted utilizing the fact that the dissolution proceeds more and the viscosity increases as the difference between the dissolution temperature T0 and the temperature T2 or T3 is larger. Also, it is known that T0 is decreased by a salting out effect when a trace amount of an alkaline metal salt or alkaline earth metal salt, such as NaCl. KCl, disodium hydrogen phosphate, disodium sulfite or trisodium citrate, is added, and the degree of partial dissolution of the component i can be also adjusted by adjusting T0.

4. Method for Preparing Enteric Hard Capsule

A fourth aspect of the present invention relates to a method for preparing an enteric hard capsule. According to the present invention, the enteric hard capsule can be prepared using a capsule preparation machine for preparing other hard capsules. The hard capsule of the present invention is characterized by being formed by a dipping method, in particular by a "cold pin dipping method." A "cold pin dipping method" is characterized in that the surface temperature of the molding pin during dipping is lower than the temperature of the capsule preparation liquid.

The method for preparing (molding) an enteric hard capsule is not particularly limited as long as the method includes a step of preparing a capsule using the enteric hard capsule preparation liquid according to the present invention. In general, an enteric hard capsule is obtained with desired capsule shape and thickness by dipping a mold pin (capsule molding pin) serving as a mold for a capsule into an enteric hard capsule preparation liquid and curing and drying the film adhering to the mold pin when it is pulled up (dipping method). Specifically, the method for preparing an enteric hard capsule includes a provision step of preparing an enteric hard capsule preparation liquid by the above-mentioned method or purchasing an enteric hard capsule preparation liquid, for example, and a preparation step of dipping a mold pin into the enteric hard capsule preparation liquid, pulling up the mold pin, inverting the mold pin upside down, and drying the solution adhering to the mold pin.

More specifically, the enteric hard capsule used in the present invention can be produced through the following molding steps:

(1) a step of dipping a mold pin into an enteric hard capsule preparation liquid (dipping step), (2) a step of pulling up the mold pin from the enteric hard capsule preparation liquid (dipping liquid) and drying the enteric hard capsule preparation liquid adhering to an outer surface of the mold pin (drying step), and (3) a step of releasing the dried capsule film (film) from the capsule molding pin (releasing step).

Here, the enteric hard capsule preparation liquid is held at a temperature T5 that is lower than the cloud point of the water-soluble cellulose compound and higher than room temperature (20° C. to 25° C.) when the mold pin is dipped into it. T5 is preferably not lower than the cloud point T0 by 10° C. or more, is more preferably equal to or higher than T2. As a result, the partially dissolved state of the component i can be kept stably. For example, T5 is preferably within the range of 30° C. to 60° C. When the water-soluble cellulose compound is HPMC or MC, the temperature T5 can be within the range of 40° C. to 60° C. T3 and T5 can be similar to each other.

The viscosity of the capsule preparation liquid during dipping is preferably 100 mPa·s or more, more preferably 500 mPa·s or more, still more preferably 1000m Pa s or more at the temperature T5, at which the capsule preparation liquid is held.

Also, the viscosity of the capsule preparation liquid during dipping is preferably 10000 mPa·s or less, more preferably 5000 mPa·s or less, still more preferably 3000 mPa·s or less at the temperature T5, at which the capsule preparation liquid is held.

The viscosity of the capsule preparation liquid can be measured using a single cylinder type rotary viscometer (Brookfield type viscometer, B-type viscometer). For example, the viscosity can be measured with a M3 rotor (measurement range 0 to 10,000 mPa·s) placed in a capsule preparation liquid prepared in a 1 L beaker (liquid amount 600 ml) and maintained at 55° C. at a rotor rotational speed of 12 r.p.m. with a measurement time of 50 second.

In contrast, the mold pin during dipping preferably has a surface temperature T6 that is lower the liquid temperature T5 of the enteric hard capsule preparation liquid and lower than the temperature T4, at which an abrupt increase in viscosity due to cold gelation occurs. For example, the temperature T6 is in the range of 20° C. to 30° C., more preferably in the range of 20 to 28° C.

The drying step (2) is not particularly limited and can be conducted at room temperature (20 to 30° C.). Usually, the drying is achieved by blowing air at room temperature.

The undried film adhering to a surface of the mold pin immediately after it is pulled up from the capsule preparation liquid has a composition substantially the same as that of the preparation liquid and therefore has a moisture content of about 70 to 90%, for example. It is preferred to adjust the drying temperature, humidity and time so that the film after drying may have a moisture content of at least 2% or more.

The capsule film prepared in this way is cut to a predetermined length and can be provided as an enteric hard capsule with its paired body portion or cap portion fitted thereto or not.

Enteric hard capsules usually have a film thickness in the range of 50 to 250 μm. In particular, currently commercially available capsules have a sidewall portion usually having a thickness of 70 to 150 μm, more preferably 80 to 120 μm. There are No. 00. No. 0, No. 1, No. 2, No. 3, No. 4, No. 5 and so on as the sizes of enteric hard capsules. In the present invention, an enteric hard capsule of any size can be prepared.

5. Enteric Hard Capsule Formulation

When the enteric hard capsule of the present invention is used, it is possible to realize an enteric hard capsule formulation filled with an active drug and characterized by being configure to have a dissolution rate of the active drug of 10% or less after the elapse of two hours in a dissolution test using a solution having a pH of 1.2.

Examples of the active drug to be filled in the enteric hard capsule of the present invention include one component or two or more components selected from nutritional fortification healthcare agents, antipyretic, analgesic, and anti-inflammatory agents, psychotropic agents, anxiolytic agents, antidepressants, hypnosedatives, anticonvulsive agents, central nervous system agents, brain metabolism-improving agents, brain circulation-improving agents, antiepileptic agents, sympathomimetic stimulants, gastrointestinal agents, antacids, anti-ulcer agents, antitussive and expectorant agents, antiemetic agents, anapnoics, bronchodilators, anti-allergic agents, agents for dental and oral use, antihistamines, cardiotonic agents, agents for arrhythmia, diuretic agents, hypotensive agents, vasoconstrictive agents, coronary vasodilators, peripheral vasodilators, agents for hyperlipidemia, cholagogues, antibiotics, chemotherapeutic agents, agents for diabetes, agents for osteoporosis, antirheumatic agents, skeletal muscle relaxants, spasmolytic agents, hormonal agents, alkaloidal narcotics, sulfa drugs, arthrifuges, anticoagulant agents, and antineoplastic agent. These pharmaceutically effective components are not particularly limited and may include a variety of known components. These components may be used alone or as a compound drug with other components. Also, these components are filled in a fixed known amount as appropriate based on the condition, age and so on of the patient.

Examples of the nutritional fortification healthcare agents include vitamins such as vitamin A, vitamin D, vitamin E (e.g., d-α-tocopherol acetate), vitamin B1 (e.g., dibenzoyl thiamine, fursultiamine hydrochloride), vitamin B2 (e.g., riboflavin butyrate), vitamin B6 (e.g., pyridoxine hydrochloride), vitamin C (e.g., ascorbic acid, sodium L-ascorbate), and vitamin B12 (e.g., hydroxocobalamin acetate, cyanocobalamin); minerals such as calcium, magnesium and iron; proteins; amino acids; oligosaccharides; and crude drugs.

Examples of the antipyretic, analgesic, and anti-inflammatory agents include, but are not limited to, aspirin, acetaminophen, ethenzamide, ibuprofen, diphenhydramine hydrochloride, chlorpheniramine dl-maleate, dihydrocodeine phosphate, noscapine, methylephedrine hydrochloride, phenylpropanolamine hydrochloride, caffeine, caffeine anhydride, serrapeptase, lysozyme chloride, tolfenamic acid, mefenamic acid, diclofenac sodium, flufenamic acid, salicylamide, aminopyrine, ketoprofen, indomethacin, bucolome, and pentazocine.

In particular, the application of the enteric hard capsule is highly useful when the active drug causes a side effect on the stomach when dissolved in the stomach, or when the active drug is unstable to an acid but required not to be dissolved in the stomach but to be absorbed in the intestine. In other words, the enteric hard capsule formulation of the present invention is particularly useful for a formulation containing an active ingredient the efficacy of which is decreased by the gastric acid because the capsule can protect the active ingredient from the gastric acid and allows it to pass through the stomach effectively and to be delivered to the intestine.

For example, aspirin is known to have a side effect that causes gastric ulcer-like symptoms when administered in a large amount in the form of uncoated granules, for example, and is one of typical drugs to which the enteric hard capsule is desired to be applied.

On the other hand, examples of pharmaceutically effective components unstable to an acid include omeprazole, lansoprazole, rabeprazole sodium and esomeprazole magnesium hydrate known as proton pump inhibitors (PPIs). PPIs reach parietal cells through the blood stream and are activated upon contact with high-concentration hydrogen ions in the secretory canaliculus of the parietal cells. However, PPIs are drugs that are extremely unstable in an acidic environment, and cannot exhibit a sufficient effect when exposed to an acid before reaching the parietal cells. Thus, PPIs are usually formed into an enteric formulation in order to allow PPIs to exhibit their ability to inhibit acid secretion.

In particular, in order to protect an active drug sensitive to acids, it is preferred to use an enteric hard capsule that has a dissolution rate of 25% or less after the elapse of two hours in a dissolution test using a solution having a pH of 4.0 to provide a hard capsule formulation adapted to have a dissolution rate of the active drug of 30% or less, preferably 25% or less, after the elapse of two hours in a dissolution test using a solution having a pH of 4.0.

The meaning of pH of 4.0 is that it is generally known that the pH increases up to about 4.0 within about one hour in the stomach after a meal and it is preferred to prevent dissolution in the stomach even during this time.

Duloxetine, which is one of antidepressant drugs called serotonin noradrenaline reuptake inhibitors, is also sensitive to acids and an exemplary active pharmaceutical ingredient that is desired to be formed into an enteric formulation.

Healthy foods (including foods for specific health use or nutritional supplements, such as fucoidan, heme iron, and polyphenols) that may be filled in the enteric hard capsule of the present invention include, but are not limited to, peptides and amino acids (e.g., royal jelly, ornithine, citrulline, aminolevulinic acid, black vinegar, or hydrophobic amino acids such as methionine, valine, leucine and isoleucine), proteins (e.g., milk proteins such as lactoferrin, collagen and placenta), glycoproteins, enzyme-fermented foods (e.g., nattokinase), coenzymes (e.g., coenzyme Q10), vitamins (e.g., β-carotene), minerals, viable bacteria (e.g., yeasts, *lactobacillus* and bifidobactera), plant extracts (e.g., crude drugs and herbs, such as turmeric extract, carrot extract, Japanese plum extract, ginkgo leaf extract, blueberry extract and *Rubus suavissimus* extract), and natural organic substances such as propolis, or any combination thereof.

The enteric hard capsule may be filled with such a content using a per se known capsule filling machine, such as a fully automatic capsule filling machine (model name: LIQFIL super 80/150, manufactured by Qualicaps Co., Ltd.) and a capsule filling and sealing machine (model name: LIQFIL super FS, manufactured by Qualicaps Co., Ltd.). The body portion and the cap portion of the thus obtained hard capsule are joined to each other by covering the body portion with the cap portion and fitting them to each other after the contents are filled in the body portion. Then, when necessary, the filled capsule may be made tamper-resistant using an appropriate technique to permanently seal the seam. Typically, a sealing or banding technique may be used, and these techniques are well-known to those skilled in the art of the field of capsules. As a specific example, an enteric hard capsule formulation can be obtained by applying a sealing agent of a polymer solution once or a plurality of times, preferably once or twice, to a surface of the body portion and a surface of the cap portion in a circumferential direction of the body portion and the cap portion within a certain width on both sides of an end edge of the cap portion to seal the fitted portions. As the polymer solution, a diluted aqueous solution of an enteric polymer, or a solution of an enteric polymer in a water/ethanol or water/isopropanol solvent may be used. When a diluted aqueous solution of an enteric polymer or a solution of an enteric polymer in a solvent containing water is used, a basic neutralizing agent as described above may be used to partially dissolve the enteric polymer. Also, a plasticizer or surfactant may be added thereto.

A more specific aspect is a sealing liquid containing 10 to 50% by mass of L100-55, which a dried powder of the solid content of L30D-55, a (meth)acrylic acid copolymer used for the capsule film, 0.0 to 0.6% by mass of NaOH as a basic neutralizing agent, and 0.5 to 40% by mass of triethyl citrate with the balance being water/ethanol mixed solvent. Preferred is a sealing liquid containing 12.5 to 40.0% by mass of L100-55, 0.0 to 0.4% by mass of NaOH as a basic neutralizing agent, and 1.0 to 3.5% by mass of triethyl citrate with the balance being water/ethanol mixed solvent. More preferred is a sealing liquid containing 15.0 to 30.0% by mass of L100-55, 0.0 to 0.2% by mass of NaOH as a basic neutralizing agent, and 1.5 to 3.0% by mass of triethyl citrate with the balance being water/ethanol mixed solvent.

The rate of ethanol in the water/ethanol mixed solvent is 10 to 70% by mass, preferably 20 to 60% by mass, more preferably 30 to 50% by mass.

AS another aspect, hydroxypropyl methylcellulose acetate succinate (HPMCAS) may be used as the enteric polymer. More specifically, a sealing liquid containing 10 to 40% by mass of HPMCAS-MF (manufactured by Shin-Etsu Chemical Co., Ltd.) with the balance being ethanol may be used. Preferred is a sealing liquid containing 12.5 to 35% by mass of HPMCAS-MF with the balance being ethanol. More preferred is a sealing liquid containing 15 to 30% by mass of HPMCAS-MF with the balance being ethanol.

When the capsule is sealed, a band seal preparation liquid can be generally used at room temperature or under heating. From the viewpoint of preventing liquid leakage from the hard capsule, the use of a seal preparation liquid preferably in a temperature range of about 23 to 45° C., more preferably about 23 to 35° C., most preferably about 25 to 35° C. is desired. Although the temperature of the seal preparation liquid may be adjusted by a method which is per se known, such as a panel heater or hot-water heater, it is preferred to adjust the temperature using a circulating hot-water heater or a seal-pun unit of the above-mentioned integrated capsule filling and sealing machine which has been converted to a circulating hot-water heater type, for example, because the temperature width can be delicately regulated.

The thus obtained enteric hard capsule formulation of the present invention is designed to exhibit acid resistance in the stomach and release the content through dissolution of the capsule film after being transferred into the intestine when administered and taken into the body of a human or animal. Therefore, it is suitable as a formulation filled with a pharmaceutical product or food that is not desired to be released in the stomach.

In the present invention, in order to enhance the enteric function, to impart an additional drug delivery control function, or to control gas or moisture permeability, the capsule film may be coated from outside with one or more additional polymer layers.

Unless otherwise stated, a functional polymer layer means a layer containing a functional polymer that imparts a specific mechanical or chemical property to the capsule film coated therewith. The functional polymer is an enteric polymer and/or colon release polymer that has been conventionally used to coat a pharmaceutical solid dosage form (that is, a polymer used to disintegrate a coated dosage form in the colon region of the subject), for example.

Because the hard capsule of the present invention can control the difference in the dissolving rate (the rate of increase of the dissolution rate over time) in an intestinal environment, that is, after the pH reaches 6.8, it can be applied to the drug delivery in the aspects as described below.

In other words, there are the following aspects.

(Aspect 5-1)

This aspect relates to a hard capsule formulation that includes an enteric hard capsule filled with an active drug and is adapted to have a dissolution rate of the active drug of 75% or more after the elapse of 45 minutes in a dissolution test using a solution having a pH of 6.8.

In particular, the hard capsule formulation can improve the absorption efficiency of the active drug in the small intestine by delivering it to an upper section of the small intestine.

(Aspect 5-2)

This aspect relates to a hard capsule formulation that includes an enteric hard capsule filled with an active drug and is adapted to take 60 minutes or more before having a dissolution rate of the active drug of 75% or more in a dissolution test using a solution having a pH of 6.8.

In particular, the hard capsule formulation can deliver the active drug to a lower section of the small intestine or the large intestine and is therefore expected to be effective in suppression of inflammatory disorders in these sites. Alternatively, the hard capsule formulation has a longer active drug releasing time in the small intestine and can be expected to provide a sustained pharmaceutical effect.

(Aspect 5-3)

A novel application example using the enteric hard capsule according to the present disclosure is a hard capsule formulation characterized by containing an enteric hard capsule according to the present disclosure in a hard capsule dissolvable in an acidic condition. Hard capsules dissolvable in an acidic condition include, but are not limited to, gelatin capsules and hypromellose capsules, or pullulan capsules. In particular, in hypromellose hard capsules, water-soluble cellulose having a labeled viscosity (viscosity grade) value of 3 to 15 mPa·s is used (Japanese Unexamined Patent Application Publication Nos. Hei 08-208458, 2001-506692, 2010-270039 and 2011-500871). In these, water-soluble cellulose, in particular HPMC, accounts for almost 100% of the film (the film may contain about 0 to 5% by mass of a gelling agent, a gelation aid, a light-shielding agent, a colorant and so on, and about 0 to 10% by mass of residual moisture). An active ingredient B is filled in advance in the enteric hard capsule according to the present disclosure, and a pharmaceutically effective component A and the filled enteric hard capsule are filled in a hard capsule dissolvable in an acidic condition. Such a double capsule formulation enables selective delivery of different pharmaceutically effective components to a plurality of sites such that the active ingredient A is released in the stomach and the pharmaceutically effective component B is released after the capsule reaches the intestine. Each of the active ingredient A and the active ingredient B may be an active drug described in the above-mentioned section 5.

6. Hard Capsule Film Having Two-Phase Structure and Method for Preparing Hard Capsule Having the Film Structure The sea-island structure characteristic of the hard capsule film and the method (production process) for preparing a hard capsule having the film structure disclosed in this specification are not limited to an enteric hard capsule and may also encompass a novel functional hard capsule and a method for preparing the same as described below.

In other words, the disclosure of this specification includes the following:

A hard capsule composed of a hard capsule film having a two-phase structure consisting of core particle phases composed of fine particles of a water-soluble polymer free of an active drug and a binding phase covering surfaces of the core particles and/or binding the core particles, in which the binding phase primarily contains a functional polymer that is different from the water-soluble polymer and can control the dissolution characteristics of the core particle phases. Among the mechanical strengths required for hard capsules, the elastic modulus, in particular, is achieved by the water-soluble polymer for the core particle phases. For this purpose, the core particle phase component preferably accounts for 30% by mass or more, more preferably 40% by mass or more, of all the components of the film. On the other hand, the upper limit thereof is preferably 70% by mass or less. Alternatively, the total cross-sectional area of the core particle phases preferably accounts for 30% or more, more preferably 40% or more, of a cross-section of the hard capsule film. The core particle phases may be composed of two or more water-soluble polymers. The upper limit thereof is preferably 70% or less. On the other hand, the rate of the mass of the functional polymer to the mass of the entire capsule film is preferably 30 to 60% by mass. In addition, the sum of the core particle phase component and the functional polymer component is preferably 70% by mass or more of the mass of the entire film.

On the other hand, the function imparted to the hard capsule is achieved by the binding phase primarily containing a functional polymer. Here, the "function" is preferably intended to mean control of the dissolution characteristics of the capsule film. The control of dissolution characteristics refers to control of characteristics such as enteric properties utilizing the pi dependence, dissolvability in the lower intestine tract, which is an environment with a pH slightly higher than 7, and sustained-release properties. In general, the sustained-release properties often mean delivery of a drug to the lower intestine tract and its extended release therein, and are therefore achieved by the use of an enteric and sustained-release polymer or a combined use of an enteric polymer and a sustained-release polymer. These polymers are all poorly soluble in a neutral water solvent. Specific examples include a coating agent composed of an enteric or sustained-release (meth)acrylic acid copolymer, which is a copolymer of methacrylic acid with an alkyl (meth)acrylate ester. Also, a water-insoluble alkyl (meth)acrylate ester copolymer can be also used to reduce permeation of water and to impart a sustained-release function. More specific usable examples of the (meth)acrylic acid copolymer having an enteric function include a copolymer composed of 40 to 60% by mass of methacrylic acid and 60 to 40% by mass of ethyl acrylate as described above. Usable examples of the water-insoluble alkyl (meth)acrylate ester copolymer having a sustained-release function include a copolymer composed of 20 to 40% by mass of methyl methacrylate and 60 to 80% by mass of ethyl acrylate as also described above.

It is conventionally known that dissolution characteristics can be controlled by adjusting the blend ratio between an enteric polymer containing carboxyl groups, in particular, a methacrylic acid copolymer, and a neutral (water-insoluble) polymer (Patent Documents 27, 28 and 29). This method for controlling dissolution characteristics can be applied to the binding phase of the present hard capsule film to control the dissolution characteristics of the entire capsule film. However, in these Patent Documents, there is no suggestion about a composition further containing a significant amount, for example, 30% by mass or more, of a water-soluble polymer, in particular, water-soluble cellulose, and formation of a multiphase structure containing core particle phases thereof. Usually, a self-supporting film strength cannot be obtained with such a coating agent alone. Also, an enteric methacrylic acid copolymer coating agent, for example, is acidic itself and therefore cause a functional contradiction in which the coating agent, when directly coated on an active drug sensitive to an acid, denature and/or decompose the active drug (Non-Patent Document 8). Thus, a complicated formulation process is required in which a coating fluid composed primarily of an enteric polymer is coated on a core (usually uncoated tablet) containing an active drug not directly but after an intermediate layer is coated thereon to avoid direct contact with an acid.

In the film having the above-mentioned two-phase structure, the core particle phases of a water-soluble polymer can maintain the mechanical strength of the hard capsule film. In addition, it is possible to allow the hard capsule film to maintain sufficient mechanical strength on its own and control the dissolution characteristics thereof by mixing a relatively small amount of a functional polymer even without a complicated process in which an intermediate layer and a functional polymer are coated on an external surface of a hard capsule composed merely of a water-soluble polymer. Also, it is possible to avoid direct contact between the active drug filled in the hard capsule and a coating fluid, and it is therefore possible to prevent deterioration of the active drug caused by an enteric coating agent as described above. Thus, the rate of the mass of the core particles composed of a water-soluble polymer to the mass of the entire capsule film is preferably 30 to 70% by mass or more, more preferably 40% by mass or more. So far, there has been a formulation having desired disintegration and dissolution characteristics achieved by, for example, coating a powder or granules containing an active drug with a functional coating by a method such as spray-coating and compressing the coated powder or granules into a solid tablet after the addition of a binder (Non-Patent Document 9). However, a hard capsule obtained by coating core particles of a water-soluble polymer free of an active drug in advance followed by film formation in a single operation by a dipping method, in particular, is not known.

Here, in order to form the two-phase structure in a single dipping operation by a typical dipping method for a hard capsule, a hard capsule preparation liquid containing an aqueous solvent in which fine particles of a water-soluble polymer free of an active drug and acceptable pharmaceutically or as a food additive are dispersed and in which a functional polymer different from the water-soluble polymer is dissolved and/or colloidal particles of a functional polymer different from the water-soluble polymer are dispersed is used. In the capsule preparation liquid for dipping, it is preferred that at least some, preferably most, of the core particles of a water-soluble polymer remain undissolved to form a suspension (fluid dispersion of solid fine particles) and the functional polymer is dissolved or coexist as a fluid dispersion of stable colloids finer than the core particles in the solvent. The hard capsule film preferably has a thickness in the range of 50 to 250 μm. The water-soluble polymer ingredient for forming the core particles, which is usually supplied as a dry ingredient (powder), preferably has an average particle size in the range of 1 to 100 μm, which is sufficiently smaller than the thickness of the capsule film.

On the other hand, when the functional polymer forms colloidal particles, the colloidal particles preferably has an average particle size of less than 1 μm, more preferably less than 0.1 μm, which is about one digit smaller than that of the core particles.

Because the core particles are fine particles of the water-soluble polymer remaining undissolved, the functional polymer added separately cannot penetrate deep into the core particles as a dispersoid, and is mainly dissolved or dispersed as colloidal particles in the solvent between the core particle phases. The dispersion medium leads to formation of the binding phase. It is preferred that the surfaces of the solid particles are coated with the functional polymer in the aqueous solvent during loss on drying and prevented from further dissolution, and a stable fluid dispersion of the core particles is formed.

In forming such core particle phases, the water-soluble polymer is preferably a polymer that is used on its own as a material of a hard capsule film that quickly dissolves in water. Above all, a water-soluble polymer having a lower critical solution temperature (LCST)(sometimes referred to simply as dissolution temperature), that is T0, (hereinafter sometimes referred to as LCST polymer), is suitable for forming a (quasi)stable fluid dispersion of undissolved fine particles (core phase fluid dispersion) in a temperature decreasing process, in particular. When a dry ingredient powder of the above-mentioned water-soluble cellulose is uniformly dispersed in water at a temperature sufficiently higher than the lower critical solution temperature T0 and the temperature of the water is decreased, the fine particles of the powder (which will serve as core particles) gradually swell and start partially dissolving probably from their surfaces when the temperature passes around T0.

In the case of an aqueous solution of a water-soluble polymer having a lower critical solution temperature T0 (LCST polymer) alone, the water-soluble polymer initially dissolves partially to form a fluid dispersion of fine particles in the process of decreasing the temperature to T0 or lower. The fluid dispersion, if the dissolution concentration is appropriate, once exhibits an abrupt increase in viscosity presumed to be derived from a structural viscosity. Then, the viscosity decreases and disappears as the dissolution further proceeds, and the fluid dispersion turns into a high-concentration aqueous solution in which the water-soluble polymer is dissolved almost completely at around room temperature. The fluid dispersion in an early stage of the abrupt increase in viscosity forms a stable fluid dispersion of fine particles that will serve as core particles in the capsule film when the temperature is held constant to allow no further temperature decrease. The fluid dispersion does not need to be in a completely equilibrium and stable state as long as it is stable (in a quasi-stable state) for an approximate period for which it is usable industrially or under storage conditions.

On the other hand, the viscosity of an aqueous solution of an LCST polymer subjected to a continuous temperature decrease until the polymer is once completely dissolved becomes much lower than the viscosity of the partially dissolved dispersion. Also, even if the temperature is increased to a level lower than T0 again, the solution remains to be a completely dissolved aqueous solution. Thus, at least at a temperature lower than T0, core particle phases with a size on the order of μm are not formed again and the aqueous solution does not become cloudy again. This is a property of LCST polymers.

When the capsule preparation liquid is allowed to adhere to a mold pin at a temperature lower than the preparation liquid temperature and then dried on the pin surface, the core particle phases present in the preparation liquid on the pin surface are dissolved in the capsule preparation liquid completely and disappear during a further temperature decreasing process. In order to prevent this, it is required that the surfaces of the core particles are coated with molecules or colloidal particles of a functional polymer, that is, one end of the functional polymer is adsorbed on the surface of a core particle. In the capsule preparation liquid, when the core particle phases composed of an LCST polymer in a partially dissolved state have been coated with the functional polymer, the core particle phases are prevented from further dissolution in a further temperature decreasing process and the two-phase structure is preserved.

Coating the surfaces of the core particles with the functional polymer can be achieved by an interaction, such as hydrogen bonding, between the functional groups of the water-soluble polymer present on the surfaces of the core particles and the functional groups of the functional polymer in the capsule preparation liquid, for example. At the same time, it is desired that the surfaces of individual core particles are covered almost completely with molecules of the functional polymer as a result of this adsorption. If the functional polymer is dissolved, a dense surface adsorption layer will be naturally formed easily. Even when the functional polymer is in the form of an emulsion of colloidal particles, the fact that the colloidal particles have an average particle size that is smaller by about one digit or more than the average particle size of the core particles is advantageous and preferred for the formation of a dense surface adsorption layer on the surfaces of the core particles.

Examples of the water-soluble polymer include water-soluble cellulose compounds (water-soluble cellulose polymers). The phenomenon is known per se in which, in a fluid dispersion containing a diluted aqueous solution of a water-soluble cellulose polymer (with a concentration of less than about 5% by mass) and colloidal particles of another polymer dispersed therein (latex), the molecules of the dissolved water-soluble polymer adsorb on the colloidal particles (Non-Patent Documents 10 and 11). Also, there is a report suggesting an interaction between hydroxyl groups in water-soluble cellulose and carboxyl groups in a functional polymer (methacrylic acid copolymer) although in an organic solvent (hydrogen bonding is considered to be involved) (Non-Patent Document 12). These theories describe an interaction between molecules of dissolved water-soluble cellulose and surfaces of colloidal particles in a diluted solution (aqueous solution or organic solvent solution) of water-soluble cellulose with a concentration of less than about 5% by mass. Such an interaction is, as disclosed in this specification, believed to function also in the interaction between the surfaces of the core particles of the water-soluble polymer and the molecules or colloidal particles of the functional polymer in the high-concentration (about 10% by mass or more) aqueous dispersion of fine particles of the water-soluble polymer and the functional polymer. However, a specific example is not known in which such an interaction is controlled by a treatment such as an adequate degree of partial neutralization to utilize a temperature-dependent (cold gelation) viscoelasticity behavior. On the other hand, the hard capsule film having a two-phase structure as disclosed in this specification is not bound by the theory of the interaction (such as hydrogen bonding, electrostatic force or van der Waals' force) in an aqueous solution and the preparation method as described above.

Also, the interaction between the core particles and the functional polymer is sufficient when adsorption or coating of the functional polymer on the core particles dispersed in the aqueous solution for dipping is at least ensured, more preferably, the fluid dispersion is stable, and does not necessarily need to involve a phenomenon such as cold gelation. The gelation may be ensured by a gelling agent and a gelation aid added to the preparation liquid in addition to the functional polymer. The amount thereof to be added is preferably about 3% by mass or less, more preferably 1% by mass or less, based on the total amount of the capsule preparation liquid, which is taken as 100% by mass.

In order to take advantage of the intrinsic coating function of a functional polymer, the amount of the functional polymer (or colloidal particles thereof) to be adsorbed must be sufficient to at least cover the surface area of the core particles almost completely. The rate of the mass of the functional polymer to the mass of the entire capsule film is preferably 30 to 60% by mass although it is believed to depend also on the molecular weight of the functional polymer or the particle size of the colloidal particles of the functional polymer. The core particles are mostly undissolved, and therefore, in the binding phase, a composition composed primarily of the functional polymer is automatically achieved and functions effectively as a coating layer on the core particles.

On the other hand, in order to increase the adhesion between the core particle phases of the water-soluble polymer and the binding phase, the binding phase may contain a partially dissolved water-soluble polymer. For example, as described in the aspect 3-1, when an LCST polymer is used for the core particle phases, the degree of partial dissolution can be controlled, in other words, the concentration of the water-soluble polymer in the binding phase can be adjusted as appropriate by decreasing the LCST temperature to a temperature T2, which is slightly lower than T0. However, it is preferred that the binding phase is composed primarily of a functional polymer. In other words, the rate of the mass of the functional polymer is preferably 50% by mass, more preferably 60% by mass or more, still more preferably 70% by mass based on the total mass of the binding phase components, which is taken as 100% by mass. This ensures the solubility control function of the functional polymer as the entire binding phase.

Here, when the functional polymer is dispersed as colloidal particles, the colloidal particles may remain or may be partially dissolved. Thus, the binding phase itself does not necessarily form a single phase and may have a lower phase structure. In addition, the fine particles of the water-soluble polymer of the core particle phases may contain two or more types of water-soluble polymers. Furthermore, individual core particle phases may be surrounded by the binding phase and isolated, or the core particle phases may have a lamella structure in which the core particle phases are connected each other.

As water-soluble cellulose compounds having an LCST, cellulose derivatives are known in which some of hydroxyl groups in the cellulose molecules are substituted to impart water-solubility. More specifically, these are cellulose derivatives in which some of hydroxyl groups are substituted with methyl groups and/or hydroxypropyl groups, and, more specifically, are methylcellulose and hydroxypropyl methylcellulose. The LCST thereof is in the range of about 30 to 60° C.

The hard capsule film preferably has a thickness in the range of 50 to 250 μm as described above. Thus, the water-soluble polymer ingredient, which is usually supplied as a dry ingredient (powder), preferably has an average particle size sufficiently smaller than the thickness of the capsule film. The average particle size is preferably in the range of 1 to 100 μm.

More preferably, the water-soluble polymer is methylcellulose and/or hydroxypropyl methylcellulose having a viscosity value of 6 mPa·s or more.

A specific aspect of an enteric or sustained-release hard capsule composed of a hard capsule film having the above-mentioned two-phase structure that is formed in a single dipping operation by a general dipping method is an enteric or sustained-release hard capsule composed of a film containing a component I and a component II. The component I may be a water-soluble cellulose polymer having a lower critical solution temperature and an average particle size of 1 to 100 μm. The component II may be an enteric coating base and/or a sustained-release coating base that are water-soluble or form an aqueous dispersion of colloidal particles. The enteric or sustained-release hard capsule may be formed through a process including at least a first step of dipping a mold pin into a capsule preparation liquid maintained at a temperature close to the lower critical solution temperature of the component I, the mold pin having a surface temperature that is lower than the temperature of the preparation liquid and the preparation liquid being an aqueous dispersion containing undissolved fine particles of the component I and the component II; and a second step of pulling up the mold pin from the preparation liquid and drying the preparation liquid adhering to the mold pin.

As another aspect, a specific aspect of an enteric hard capsule composed of a hard capsule film having the above-mentioned two-phase structure that is formed in a single dipping operation by a general dipping method is an enteric hard capsule composed of a film containing a component I and a component II. The component I may be methylcellulose and/or hydroxypropyl methylcellulose having a viscosity value of 6 mPa·s or more. The component II may be an enteric methacrylic acid copolymer. The enteric hard capsule may be formed through a process including at least a first step of dipping a mold pin into an enteric hard capsule preparation liquid maintained at 30 to 65° C., the mold pin having a surface temperature that is lower than the temperature of the preparation liquid and the enteric hard capsule preparation liquid being composed of an aqueous dispersion containing fine particles of the component I and the component II and further containing a basic neutralizing agent that can partially neutralize the component II; and a second step of pulling up the mold pin from the preparation liquid and drying the preparation liquid adhering to the mold pin.

The discussion about one example of the presumed mechanism of the formation of the two-phase structure having core particle phases of a water-soluble polymer having an LCST as described above in this aspect may provide a theoretical ground for widespread application of the disclosure of this specification to the technical field of hard capsules without limiting it to the description in this specification in light of the examples described later. However, even if the microstructure itself of the hard capsule film in the present disclosure is novel, the above-mentioned one formation method and its theory do not necessarily bind the aspects disclosed in this specification.

EXAMPLES

I. Materials Used

The materials used in Examples, Reference Examples and Comparative Examples are as follows.

1. Water-Soluble Cellulose Compounds

As methylcellulose (MC) and hydroxypropyl methylcellulose (HPMC), METOLOSE (trademark) series or TC-5 (trademark) series and SH series from Shin-Etsu Chemical Co., Ltd. were used. As the hydroxypropyl cellulose (HPC), NISSO HPC series from Nippon Soda Co., Ltd. were used. Specific product names and their substitution degree types and "viscosity values" (labeled viscosities or viscosity grades) are as shown in Table 2.

The particle size distributions of the TC-5 series and SI series HPMCs were measured with a laser diffraction type particle size distribution measuring device ("Microtrack particle size distribution diameter MT3300II EX" manufactured by MicrotrackBEL Co., Ltd.). The average particle sizes were in the range of 50 to 100 μm. The volume fractions of the particles with a particle size of 100 μm or more were 50% or more.

TABLE 2

| Product name | Substitution degree type | Labeled viscosity mPa·s | Notation in the following examples (in conformity with manufacturer product number) |
|---|---|---|---|
| MC SM | — | 25, 100 | SM**, ** is labeled viscosity |
| HPMC 60SH | 2910 | 50, 4000 | 60SH**, ** is labeled viscosity |
| HPMC 65SH | 2906 | 50, 400 | 65SH**, ** is labeled viscosity |
| HPMC 90SH | 2208 | 100 | 90SH**SR, ** is labeled viscosity |
| HPMC TC-5 | 2910 | 4.5, 6, 15 | M, R and S correspond to labeled viscosities of 4.5, 6 and 15, respectively. |
| HPC HPC L | — | 6-10 | HPC - L |

2. Enteric Methacrylic Acid Copolymers

EUDRAGIT (trademark) series L30D-55 and FS30D from Evonik Industries AG were used. These are all water dispersions with a solid content of 30% by mass. The neutralization equivalent of L30D-55 to sodium hydroxide is 214.8 mg/g, and the neutralization equivalent of FS30D to sodium hydroxide is 40.4 mg/g.

3. Water-Insoluble Polymers

As an alkyl (meth)acrylate ester copolymer, Eudragit (trademark) series NE30D from Evonik Industries AG was used. It is supplied as a water dispersion with a solid content of 30% by mass. As the ethyl cellulose, Aquacoat (trademark)) ECD-30 from FMC Technologies Inc. was used. It is supplied as an aqueous dispersion with a solid content of 30% by mass.

4. Plasticizers and Surfactants (Emulsifiers)

Surfactants (emulsifiers) include Polyoxyl 40 stearate (Nikko Chemicals Co., Ltd.), which is solid at an ambient temperature, Tween 80 (generic name polysorbate 80, Kanto Chemical Co., Inc. or Nikko Chemicals Co., Ltd.), which is liquid at ambient temperature, HCO60 (generic name polyoxyethylene hydrogenated castor oil 60, Nikko Chemicals Co., Ltd.), which is solid at ambient temperature, SEFSOL 218 (generic name propylene glycol monocaprylate, Nikko Chemicals Co., Ltd.), which is liquid at ambient temperature, and dioctyl sodium sulfosuccinate (Kishida Chemical Co., Ltd.), which is solid at ambient temperature. These surfactants also have multiple use as, for example, a stabilizing agent, a plasticizer, a lubricant, a plasticizer, a base and a binder. PG (propylene glycol, Wako Pure Chemical Corporation) is a plasticizer that is liquid at ambient temperature.

5. Others

Sodium hydroxide, disodium hydrogen phosphate, disodium sulfite, and trisodium citrate were purchased from Wako Pure Chemical Corporation. Titanium oxide (TIPAQUE A-100) was purchased from Ishihara Sangyo Kaisha, Ltd.

II. Measurement and Test Methods

1. Capsule Dissolution Test

In the present invention, in principle, the dissolution test specified in the Japanese Pharmacopoeia revised 17th Edition was applied. However, because the Japanese Pharmacopoeia does not specify the solubility of an empty hard capsule itself, the solubility (dissolution characteristics) of a capsule itself was evaluated in the present invention by evaluating dissolution of fast-dissolving acetaminophen. Each capsule was filled with 40 mg of acetaminophen, 140 mg of lactose, and 20 mg of sodium starch glycolate, and the thus obtained enteric hard capsule formulations were tested in accordance with the dissolution test method (the 17th Pharmacopoeia, 6.10-1.2 Paddle Method (paddle rotational speed 50 revolution/min) specified in Japanese Pharmacopoeia using a sinker corresponding to FIG. 6. 10-2a thereof, and changes over time in the dissolution rate of acetaminophen were measured. For the dissolution test, a bath-type dissolution tester Model 2100 manufactured by Distek Ltd. was used. The dissolution rate was obtained from the absorbance at 244 nm of the solution in the dissolution tester bus, which increased with the progress of dissolution of acetaminophen from the capsule, based on the absorbance at 244 nm obtained when the same amount of acetaminophen was separately dissolved in the solution completely in the dissolution tester bus, which was defined as 100%. The n number was set to N=1 to 6, and, when n is equal to or larger than 2, the average thereof was used as the dissolution rate. Here, a first liquid and a second liquid as described below were used as buffer solutions, and the following aqueous solution was used as a buffer solution 3. In each case, the temperature of the solution in the bath was set to 37° C.

First liquid: 7.0 mL of hydrochloric acid and water were added to 2.0 g of sodium chloride and dissolved and the amount was adjusted to 1000 mL (pH about 1.2, hereinafter sometimes referred to as "acidic solution").

Second liquid: Prepared by adding one volume of water to one volume of phosphate buffer solution obtained by dissolving 3.40 g of potassium dihydrogen phosphate and 3.55 g of anhydrous disodium hydrogen phosphate in water to 1000 mL (pH about 6.8, hereinafter sometimes referred to as "neutral solution").

Buffer solution 3: Prepared by dissolving 3.378 g of citric acid hydrate and 2.535 g of anhydrous disodium hydrogen phosphate in water to 1000 mL.

2. Measurement of Dynamic Viscoelasticity of Capsule Preparation Liquid

The dynamic viscoelasticity of the capsule preparation liquid was measured with a rheometer (MCR102) manufactured by AntonPaar Ltd. For the measurement, a double cylindrical tube measurement jig (model No. CC27/T200/SS) and a temperature control system C-PTD200 were used. The amount of the liquid was set to about 19 mL. Also, in order to prevent moisture evaporation during the measurement, about 1 mL of cottonseed oil was dropped onto the outermost surface of the sample liquid in the cylindrical tube. The temperature dependence was measured while the temperature was decreased from 60° C. to 20° C. at a rate of 1° C./min, and the oscillation angle of strain was simultaneously decreased linearly from 1 to 0.1%. The angular frequency ω (rad/sec) was 2π/second. As the dynamic viscoelasticity, the values of storage elastic modulus G'(Pa), loss elastic modulus G"(Pa), complex viscosity $|\eta^*|=|G^*|/\omega=\sqrt{(G'^2+G''^2)}/\omega$(Pa·s), and viscosity $\eta''=G''/\omega$(Pa·s) were measured.

3. Viscosity of Capsule Preparation Liquid

The viscosity of the capsule preparation liquid (55° C.) was measured with a Brookfield viscometer (TVB-10M (Toki Sangyo Co., Ltd.)). For the measurement, a M3 rotor (measurement range 0 to 10,000 mPa·s) was used. After the capsule preparation liquid was prepared in a 1 L beaker (liquid amount 600 ml), the rotor was placed in the beaker and measurement was made at a rotor rotational speed of 12 r.p.m. with a measurement time of 50 seconds.

4. Observation of Film Structure

A scanning electron microscope (SEM) and microscopic Raman were used for observation of the film structure.
(1) SEM
As a scanning electron microscope, Ultra55 manufactured by Carl Zeiss was used.
In order to observe a cross-section of a capsule film, the prepared capsule film was cut transversely into a small piece, which was embedded in an epoxy resin and then thinly sliced with a microtome to obtain a section for observation (with a size of about 300 to 400 μm square and a thickness of 2 to 3 μm). The section was subjected to a vapor deposition treatment with PtPd. The section was irradiated with an electron beam at an acceleration voltage of 3 kV to scan it.
(2) Microscopic Raman
As a microscopic Raman device, Nicolet Almega XR manufactured by Thermo Fisher Scientific was used. The excitation wavelength was set to 532 nm, and the resolution was set to about 10/cm (10 kaisers). The irradiation diameter was set to 1 μmφ (100 power-objective lens, 25 μm pinhole: 1 μmφ in planar direction×2 μm in depth direction (=section thickness), information on a columnar inner portion is obtained), the excitation output was set to 100% (10 mW or less @ sample position), and the exposure time×number of scans was set to 10 sec×2.
The transversely cut capsule piece was embedded in an epoxy resin and then thinly sliced with a microtome to prepare a section with a thickness of 2 μm. The section was observed on a metal plate.

Also, for observation of the microstructure of the enteric capsule by imaging Raman spectroscopy, RAMAN plus manufactured by Nanophoton Corporation was used. It has an excitation wavelength of 532 nm, an NA of 0.9, a 100-power objective lens, and a resolution of about 4 cm$^{-1}$. The excitation output, exposure time and so on were adjusted as appropriate. Mapping was performed with focus on peaks at 1370 cm$^{-1}$ (δCH3) and 1730 cm$^{-1}$ (νC=O) as Raman shifts inherent to TC-SS and L30D-55, respectively.

5. Observation of Preparation Liquid

The preparation liquid was observed under an optical microscope (BX53 manufactured by Olympus Corporation) having a stage temperature regulation function. Transmission observation was performed using a 10-power eyepiece lens and a 10-power objective lens. The preparation solution at 55° C. was dropped onto a slide glass also preheated to 55° C. on the stage, and further covered with a cover glass also preheated to 55° C.

6. Residual Salt Concentration in Film

The salt (sodium) in the capsule film was subjected to a dry ashing treatment in accordance with the following procedure, and then quantified by atomic absorption spectrometry (AAS). A sample was precisely weighed into a platinum crucible, and concentrated sulfuric acid was added thereto. After that, the mixture was heated in an electric furnace at 650° C. until no organic substance remained. The remaining ash was dissolved in diluted hydrochloric acid, diluted as appropriate, and quantified with an atomic absorption spectrophotometer (Spectr AA-220 manufactured by Varian Medical Systems, Inc.).

7. Amount of Saturated Moisture

<Method for Measuring Water Content in Capsule Film by Loss-On-Drying Method>

A potassium carbonate saturated salt was placed in a desiccator to create an atmosphere in a constant-humidity state therein, and a sample (hard capsule or film) was placed in the desiccator. The desiccator was sealed and subjected to humidity conditioning at 25° C. for one week. In the presence of a saturated aqueous potassium acetate solution, an atmosphere with a relative humidity of about 43% can be created. After the mass (wet mass) of the sample after the humidity conditioning was measured, the sample was then dried by heating at 105° C. for two hours, and the mass (dry mass) of the sample was measured again. From the difference between the mass before drying (wet mass) and the mass after drying (dry mass), the rate of moisture amount decreased by the drying by heating at 105° C. for two hours (water content) was calculated according to the following equation.

[Mathematical Formula 4]

$$\text{Water content (\%)} = \frac{\text{(Wet mass of sample)} - \text{(Dry mass of sample)}}{\text{Wet mass of sample}} \times 100$$

8. Mechanical Strength of Capsule Film (Measurement of Elastic Modulus and Rate of Elongation at Break)

When the mechanical strength of a hard capsule film is evaluated, it is important to compare test films with the same thickness. Thus, the mechanical strength of a film, which depends on the component composition of the hard capsule, was evaluated using a cast film fabricated by a casting method using a preparation liquid having the same component composition as the component composition of each hard capsule preparation liquid instead of a hard capsule molded by a dipping. The film is excellent in uniformity of thickness and reproducibility of evaluation, and well reflects the mechanical strength as a capsule film.

The cast film was fabricated by setting a metal applicator on a surface of a glass or PET film held at room temperature, casting a preparation liquid at 50° C. to 60° C. thereon, and moving the metal applicator at a constant speed to form a uniform film with a thickness of 100 μm. After that, the film was dried at a temperature of room temperature to 30° C. for about ten hours. In order to obtain a film with a uniform thickness of 100 μm, applicators having gaps ranging from 0.4 mm to 1.5 mm were used appropriately.

The fabricated film was cut into a dumbbell shape of 5 mm×75 mm (specified in JIS K-7161-2-1BA), and then subjected to a tensile test using a compact tabletop tester (EZ-LX from Simadzu Corporation). Both ends of the film were set on a holder (gap length 60 mm), and the film was pulled at a tensile rate of 10 mm/min to show the elongation of the film and a curve between the stress that occurs in the film (tensile stress) and the rate of elongation (strain). An elastic modulus, which is an indicator of hardness, was obtained from the inclination of the curve in an elastic deformation region under low stress in FIG. 5, and a rate of elongation at a breakpoint was determined as a rate of elongation at break (Non-patent Document 1, Chapter 4).

First, humidity conditioning was performed under humidity conditioning conditions of 25° C. and a relative humidity of 22% (potassium acetate saturated salt was used) for one week or longer, and then the tensile test was conducted to evaluate the mechanical strength. The tensile test was also performed in a humidity conditioned environment with a temperature of 25° C. and a relative humidity of 22%. Also, the tensile test was performed after humidity conditioning was performed under humidity conditioning conditions of 25° C. and a relative humidity of 63% (potassium acetate saturated salt was used) for one week or longer. The tensile test was also performed in a humidity-conditioned environment with a temperature of 25° C. and a relative humidity of 63%.

III. Method for Preparing Preparation Liquid

A capsule preparation liquid was prepared in accordance with the following procedure. All the operations were performed while the solution was being stirred. In the following, the solid contents of the components i to iv are referred to as polymer components (in the case of the component iv, even a liquid polymer may be referred to as solid content). Also, the total solution mass corresponds to the total mass of the purified water as a solvent as well as the polymer component, the basic neutralizing agent and other solid contents (plasticizer, light-shielding agent etc.). The polymer component concentration refers to the rate of the total mass of the polymer component to the mass of the entire solution (% by mass).

III-1. Method for Preparing Preparation Liquid (Corresponding to Aspect 3-1)

a. Purified water at room temperature was provided in such an amount that the polymer solid content concentration would reach a predetermined concentration (about 20%) in consideration of the moisture amounts in the water dispersion of a methacrylic acid copolymer as a component ii (solid content concentration 30% by mass), the fluid dispersion of an alkyl (meth)acrylate ester copolymer as a component iii (solid content concentration 30% by mass) and the fluid dispersion of titanium oxide as a light-shielding agent (concentration 22% by mass) to be added later.

b. A predetermined amount of the methacrylic acid copolymer fluid dispersion was added to the above-mentioned purified water at room temperature. After that, sodium hydroxide (NaOH) and other salts are added as a basic neutralizing agent to prepare a partially neutralized solution. Unless otherwise stated, in the following examples, NaOH was used in an amount corresponding to partial neutralization of about 8% of carboxyl groups of the methacrylic acid copolymer. In other words, an amount corresponding to about 8% of the neutralization equivalent of MaOH, which is 214.2 mg/g, was added per gram of the solid content of the methacrylic acid copolymer. The other salts were additionally added in this step. The pH of the preparation liquid after the partial neutralization is generally in the range of 5 to 6. The component iii and the component iv were added at this stage.

c. After the temperature of this partially neutralized solution was increased to 83° C., the titanium oxide fluid dispersion was added, and the mixture was well stirred with a three-one motor. After that, the water-soluble cellulose compound was added, and uniformly dispersed so as not to form lumps to prepare a suspension. The suspension was defoamed.

d. The temperature of the solution was decreased to a temperature T2 equal to or lower than the dissolution temperature (cloud point, TO) of the water-soluble polymer to prepare a fluid dispersion in which the water-soluble cellulose compound was partially dissolved. T2 was set to 50 to 55° C.

e. The fluid dispersion prepared in the step d was held at a preparation liquid temperature T3 (55° C.). The fluid dispersion of the component iii and the component iv may be added at this stage. As a result, the viscosity measured with a Brookfield viscometer was in the range of about 1,000 to 3,000 mPa·s. The final concentration of all the polymer components was finely adjusted so that the viscosity could fell in this range through addition of warm pure water and evaporation. Also, stirring was performed at 100 to 1,000 rpm with propeller blades in all of the above-mentioned steps.

Here, in the step d, it can be determined whether or not dissolution of the water-soluble cellulose compound has been started based on a change in viscosity of the fluid dispersion as an indicator. Specifically, the viscosity of the fluid dispersion, which has been substantially the same as that of water until then, abruptly increases with the start of dissolution. Also, the while turbid fluid dispersion turns into an opaque white semi-transparent solution with the dissolution of some of the particles. Thus, the temperature at which the viscoelasticity increases abruptly or an approximate temperature T4 at which the fluid dispersion turns semi-transparent was measured in advance by dynamic viscoelasticity evaluation for a fluid dispersion of the water-soluble cellulose compound alone, and T2 and T3 were set to be located in front (on the high temperature side) of T4.

IV. Method for Molding Capsule

Using the capsule preparation liquid prepared in the above-mentioned section III, a hard capsule was prepared by a cold pin dipping method. A mold pin (size No. 2) left to stand at room temperature (about 25° C.) was dipped for several seconds in the capsule preparation liquid kept at an almost constant temperature with a holding temperature T3=55° C., and then pulled up into the atmosphere. The molding pin with the capsule preparation liquid adhering thereto was inverted upside down, and dried at room atmospheric temperature for ten hours or more.

V. Preparation Examples

V-1. Preparation Example V-1

In the following examples and comparative Examples, a capsule preparation liquid was prepared in accordance with Preparation Example 111-1 (preparation method of the aspect 3-1) and molding was performed according to the molding method IV. The percentages by mass of the solid contents of the component i, the component ii, the component iii and the component iv based on the total mass of these (total mass of polymer components), which was taken as 100% by mass, were represented by α, β, γ and δ, respectively. The mass ratio of the basic neutralizing agent (NaOH) and other salts and the mass ratio of titanium oxide (light-shielding agent) based on the above-mentioned total mass of the polymer components were represented by ε(%) and σ(%), respectively. The mass ratio of the polymer components of the components i to iv based on the total mass of the purified water as a solvent and the solid contents of the components i to iv was defined as polymer component concentration (%). Each specific composition is shown in Table 3. Also, in these tables, the degree of neutralization (for the second component) refers to the degree of neutralization for the solid content of the component ii in the step A of the preparation method.

1. Example 1, Comparative Example 1

The dissolution rates of the capsule at pH 1.2 (first liquid), 4 (buffer solution 3) and 6.8 (second liquid), and the elastic modulus, rate of elongation and moisture content of a cast film with the same composition as the capsule film are shown in Table 3. Also, two types of band sealing liquids, namely, a band sealing liquid containing 20% by mass of HPMCAS-MF with the balance being ethanol and a band sealing liquid containing 19.1% by mass of L100-55, 0.169% by mass of NaOH and 1.74% by mass of triethyl citrate in a water/ethanol mixed solvent containing 40% by mass of (anhydrous) ethanol, were prepared. The band sealing liquid was applied in the shape of a band with a width of about 5 mm to cover the joint parts of the cap and body of some of the capsules of Example 1, and dried at room temperature to form a band seal. No peeling or the like occurred during the dissolution test. Also, the dissolution rate after the elapse of two hours at pH 1.2 was able to be slightly decreased. Rather, the band seal was believed to be effective in preventing leakage of the content drug due to variation of the caps and bodies of individual capsules and reducing variation in average dissolution rate as a whole. This effect was believed to help the capsule to keep good seal in combination with the fact that the capsule film was slightly swollen to be effective in closing the above-mentioned gap with the lapse of time in the dissolution test.

When the surfactant of the fourth component was further replaced with SEFSOL 218, dioctyl sodium sulfosuccinate or HCO60 with the same composition ratios as those in Examples 1 to 9 maintained, it was also confirmed that improvement in crack resistance (increase in rate of elongation at break) was achieved without impairing the enteric properties. These can reduce the viscosity of the capsule preparation liquid and are therefore useful for the adjustment of viscosity during dipping. When these surfactants or plasticizers significantly exceeded 10% by mass, the elastic modulus at 63% RH tended to fall below 1 GPa·S.

In other words, the viscosity of the capsule preparation liquid containing the polymer components of each composition of Example 1 was in the range of 500 to 10000 mPa·s when measured with a B-type viscometer at 55° C. In Example 1-12, the addition of disodium hydrogen phosphate is effective in reducing the viscosity of the capsule preparation liquid due to its salting out effect. In fact, when disodium hydrogen phosphate was not added with the same composition ratio maintained, the viscosity value (degree of polymerization) of 60SH50, which is an HPMC, was so high that it was difficult to reduce the viscosity of the capsule preparation liquid to 10,000 mPa or less unless the solid content concentration was reduced to several percent by mass. Such a low solid content concentration is not preferred for capsule production by a dipping method because it takes too much time to evaporate the moisture. On the other hand, even when the disodium hydrogen phosphate was replaced with the same percent by mass of disodium sulfite or trisodium citrate dihydrate with the composition ratio of Example 1-12 maintained, the viscosity markedly decreased due to a salting out effect to a range suitable for capsule molding by a dipping method.

Comparative Example 1-1 was an example in which the first component had a viscosity value of 4.5 mPa·s. The film of Comparative Example 1-1 was very fragile and had insufficient mechanical strength.

Comparative Example 1-2 was an example in which the first component was a hydroxypropyl cellulose (HPC). Both the capsule film and cast film of Comparative Example 1-2 had a rough surface and a low rate of elongation, and was insufficient in mechanical strength as a hard capsule.

Comparative Example 1-3 was an example in which the rate of the sum of the first component and the second component was less than 70% by mass. In particular, when the proportion of the first component was less than 30% by mass, the cast film was very fragile and it was difficult to mold a hard capsule. Here, very fragile refers to a case where molding of a hard capsule is practically difficult and the rate of elongation is presumed to falls much below 2%.

Comparative Example 1-4 was an example in which the rate of the sum of the first component and the second component was less than 70% by mass. In particular, when the rate the second component was less than 30% by mass, the film was insufficient in dissolution-reducing effect at a pH of 1.2 and shown to be not suitable for a hard capsule.

Comparative Examples 1-5 and 1-6 were examples in which the rate of the sum of the first component and the second component was 70% by mass or more but the rate of the second component was less than 30% by mass. In this case, the film was insufficient in dissolution-reducing effect at a pH of 1.2 and shown to be not suitable for a hard capsule.

Comparative Example 1-7 was an example in which the rate of the sum of the first component and the second component was 70% by mass or more and the rate of the second component was 60% by mass or more. In this case, the cast film was very fragile and molding of a hard capsule was difficult.

When the first component and the second component both accounted for less than 30% by mass, a self-supporting dry film was not able to be obtained and it was difficult to form a capsule, or either the dissolution characteristics or mechanical characteristics did not satisfy the requirements for an enteric hard capsule.

Comparative Examples 1-8, 1-9 and 1-10 were examples of cast films composed only of the second component (L30D-55) and the third component (NE30D) without containing an HPMC as the first component. Such films are often used for coating of tablets, for example. Even when the composition ratio between the second component and the third component were varied in these examples, mechanical strength suitable for a hard capsule film was not able to be obtained. The films were too insufficient in strength as a self-supporting film to undergo the tensile test, and either extremely soft or fragile.

TABLE 3

| | First component | | Second component Methacrylic | | Third component | | Fourth component | | Polymer component | Basic neutralizing agent | | Degree of neutralization |
| --- | --- | --- | --- | --- | --- | --- | --- | --- | --- | --- | --- | --- |
| | Water-soluble cellulose | Viscosity value mpa·s | α (%) | acid co-polymer | β (%) | Water-insoluble polymer | γ (%) | Plasticizer, surfactant | δ (%) | concentration (%) | Substance name | ε (%) | (%) |
| Ex. 1-1 | SM-25 | 25 | 37.7 | L30D-55 | 41.5 | NE30D | 20.8 | Nil | 0.0 | 18.3 | NaOH | 0.7 | 7.8 |
| Ex. 1-2 | SM-100 | 100 | 37.7 | L30D-55 | 41.5 | NE30D | 20.8 | Nil | 0.0 | 18.3 | NaOH | 0.7 | 7.8 |
| Ex. 1-3 | TC-5S | 15 | 58.5 | L30D-55 | 41.5 | Nil | 0.0 | Nil | 0.0 | 14.5 | NaOH | 0.7 | 7.8 |
| Ex. 1-4 | TC-5R | 6 | 58.5 | L30D-55 | 41.5 | Nil | 0.0 | Nil | 0.0 | 18.8 | NaOH | 0.7 | 7.8 |
| Ex. 1-5 | 60SH-50 | 50 | 37.7 | L30D-55 | 41.5 | NE30D | 20.8 | Nil | 0.0 | 15.4 | NaOH | 0.7 | 7.8 |
| Ex. 1-6 | TC-5S | 15 | 48.1 | L30D-55 | 41.5 | Nil | 0.0 | PG | 10.4 | 14.4 | NaOH | 0.7 | 7.8 |
| Ex. 1-7 | 60SH-50 | 50 | 53.3 | L30D-55 | 41.5 | Nil | 0.0 | Polyoxyl 40 stearate | 5.2 | 14.4 | NaOH | 0.7 | 7.8 |
| Ex. 1-8 | TC-5S | 15 | 48.0 | L30D-55 | 36.4 | NE30D | 15.6 | Nil | 0.0 | 17.8 | NaOH | 0.8 | 10.6 |
| Ex. 1-9 | TC-5S | 15 | 48.0 | L30D-55 | 36.4 | NE30D | 12.5 | Tween80 | 3.1 | 19.0 | NaOH | 0.8 | 10.6 |

TABLE 3-continued

| | | | | | | | | | | | | |
|---|---|---|---|---|---|---|---|---|---|---|---|---|
| Ex. 1-10 | TC-5S | 15 | 48.0 | L30D-55 FS30D | 36.3 15.6 | Nil | 0.0 | Nil | 0.0 | 15.3 | NaOH | 0.8 | 10.0 |
| Ex. 1-11 | TC-5S | 15 | 48.1 | L30D-55 | 36.4 | Aquacoat ECD-30 | 15.6 | Nil | 0.0 | 16.4 | NaOH | 0.8 | 10.0 |
| Ex. 1-12 | 60SH-50 | 50 | 58.0 | L30D-55 | 42.0 | Nil | 0.0 | Nil | 0.0 | 13.8 | NaOH Na2HPO4 | 0.8 1.0 | 8.0 6.0 |
| Ex. 1-13 | 60SH-50 | 50 | 52.8 | L30D-55 | 42.0 | NE30D | 5.2 | Nil | 0.0 | 14.8 | NaOH Na2HPO4 | 0.8 1.0 | 8.0 6.0 |
| Ex. 1-14 | 60SH-50 | 50 | 52.8 | L30D-55 | 42.0 | Nil | 0.0 | Propylene glycol | 5.2 | 13.8 | NaOH Na2HPO4 | 0.8 1.0 | 8.0 6.0 |
| Comp. Ex. 1-1 | TC-5M | 4.5 | 58.5 | L30D-55 | 41.5 | Nil | 0.0 | Nil | 0.0 | 21.2 | NaOH | 0.7 | 7.8 |
| Comp. Ex. 1-2 | HPC-LFP | 6~10 | 58.5 | L30D-55 | 41.5 | Nil | 0.0 | Nil | 0.0 | 19.3 | NaOH | 0.7 | 7.8 |
| Comp. Ex. 1-3 | 60SH-50 | 50 | 27.3 | L30D-55 | 41.5 | NE30D | 31.1 | Nil | 0.0 | 17.8 | NaOH | 0.7 | 7.8 |
| Comp. Ex. 1-4 | 60SH-50 | 50 | 45.7 | L30D-55 | 20.0 | NE30D | 34.3 | Nil | 0.0 | 14.0 | NaOH | 0.3 | 8.0 |
| Comp. Ex. 1-5 | 60SH-50 | 50 | 66.7 | L30D-55 | 20.0 | NE30D | 13.3 | Nil | 0.0 | 11.0 | NaOH | 0.4 | 8.1 |
| Comp. Ex. 1-6 | TC-5S | 15 | 80.0 | L30D-55 | 20.0 | NE30D | 0.0 | Nil | 0.0 | 11.0 | NaOH | 0.2 | 4.0 |
| Comp. Ex. 1-7 | 60SH-50 | 50 | 10.0 | L30D-55 | 70.0 | NE30D | 20.0 | Nil | 0.0 | 29.9 | NaOH | 0.3 | 2.0 |
| Comp. Ex. 1-8 | Nil | 0 | 0.0 | L30D55 | 75.0 | NE30D | 25.0 | Nil | 0.0 | 25.0 | NaOH | 1.4 | 8.0 |
| Comp. Ex. 1-9 | Nil | 0 | 0.0 | L30D55 | 50.0 | NE30D | 50.0 | Nil | 0.0 | 25.0 | NaOH | 0.9 | 8.0 |
| Comp. Ex. 1-10 | Nil | 0 | 0.0 | L30D55 | 25.0 | NE30D | 75.0 | Nil | 0.0 | 25.0 | NaOH | 0.5 | 8.0 |

| | Others | | pH 1.2 Dissolution rate after elapse of two hours (%) | pH 4.0 Dissolution rate after elapse of two hours (%) | pH 6.8 | | Elastic modulus/ 60% RH (GPa) | Rate of elongation/ 22% RH (%) | Moisture value/ 60% RH (%) | Moisture value/ 22% RH (%) | Moisture value/ 43% RH (calculated %) |
|---|---|---|---|---|---|---|---|---|---|---|---|
| | Substance name | σ (%) | | | Time (min) | Dissolution rate (%) | | | | | |
| Ex. 1-1 | Titanium oxide | 3.1 | 3.9 | 22.2 | 30.0 | 96.4 | 2.5 | 3.5 | 6.2 | 3.3 | 4.8 |
| Ex. 1-2 | Titanium oxide | 3.1 | 2.1 | 16.0 | 45.0 | 98.8 | 2.7 | 5.4 | 6.3 | 3.1 | 4.7 |
| Ex. 1-3 | Titanium oxide | 3.1 | 6.3 | 16.9 | 30.0 | 100.0 | 3.3 | 6.2 | 7.3 | 3.5 | 5.4 |
| Ex. 1-4 | Titanium oxide | 3.1 | 6.5 | 44.0 | 30.0 | 100.0 | 3.2 | 2.6 | 7.4 | 3.4 | 5.4 |
| Ex. 1-5 | Titanium oxide | 3.1 | Less than 1% | 12.0 | 30.0 | 99.8 | 2.3 | 5.1 | 6.0 | 3.1 | 4.5 |
| Ex. 1-6 | Titanium oxide | 3.1 | 5.3 | 21.6 | 30.0 | 100.0 | 1.4 | 7.3 | 8.3 | 3.9 | 6.1 |
| Ex. 1-7 | Titanium oxide | 3.1 | 8.1 | 23.6 | 30.0 | 97.8 | 2.9 | 6.5 | 7.0 | 3.2 | 5.1 |
| Ex. 1-8 | Titanium oxide | 3.1 | 6.2 | 34.6 | 30.0 | 97.9 | 2.0 | 4.2 | 6.3 | 2.8 | 4.6 |
| Ex. 1-9 | Titanium oxide | 3.1 | 9.2 | 46.7 | 30.0 | 97.5 | 1.7 | 6.0 | 6.4 | 2.7 | 4.6 |
| Ex. 1-10 | Titanium oxide | 3.1 | 4.7 | 23.6 | 30.0 | 97.5 | 3.1 | 3.9 | 6.7 | 3.1 | 4.9 |
| Ex. 1-11 | Titanium oxide | 3.1 | 5.5 | 26.1 | 30.0 | 95.2 | 2.7 | 2.4 | 6.6 | 2.9 | 4.8 |
| Ex. 1-12 | Titanium oxide | 3.1 | 9.6 | 30.3 | 30.0 | 98.2 | 3.2 | 11.3 | 8.2 | 3.7 | 6.0 |
| Ex. 1-13 | Titanium oxide | 3.1 | 5.1 | 27.5 | 30.0 | 98.0 | 2.9 | 6.4 | 7.9 | 3.6 | 5.7 |

TABLE 3-continued

| | | | | | | | | | | | |
|---|---|---|---|---|---|---|---|---|---|---|---|
| Ex. 1-14 | Titanium oxide | 3.1 | 6.9 | 30.0 | 30.0 | 96.3 | 2.6 | 6.3 | 8.1 | 3.4 | 5.7 |
| Comp. Ex 1-1 | Titanium oxide | 3.1 | 9.2 | 74.8 | 30.0 | 99.0 | 3.3 | 1.0 | 7.7 | 3.6 | 5.6 |
| Comp. Ex. 1-2 | Titanium oxide | 3.1 | — | — | — | — | 2.3 | 1.5 | 6.1 | 2.8 | 4.5 |
| Comp. Ex. 1-3 | Titanium oxide | 3.1 | — | — | — | — | Very fragile | | | | |
| Comp. Ex. 1-4 | Titanium oxide | — | At pH of 1.2, 25% or more was dissolved out after the elapse of two hours | | | | — | — | — | — | — |
| Comp. Ex. 1-5 | Titanium oxide | — | At pH of 1.2, 25% or more was dissolved out after the elapse of two hours | | | | — | — | — | — | — |
| Comp. Ex. 1-6 | Titanium oxide | — | At pH of 1.2, 25% or more was dissolved out after the elapse of two hours | | | | — | — | — | — | — |
| Comp. Ex. 1-7 | Titanium oxide | — | — | — | — | — | Very fragile | | | | |
| Comp. Ex. 1-8 | Titanium oxide | — | — | — | — | — | Very fragile | | | | |
| Comp. Ex. 1-9 | Titanium oxide | — | — | — | — | — | Very fragile | | | | |
| Comp. Ex. 1-10 | Titanium oxide | — | — | — | — | — | Very soft | | | | |

Figure 2:
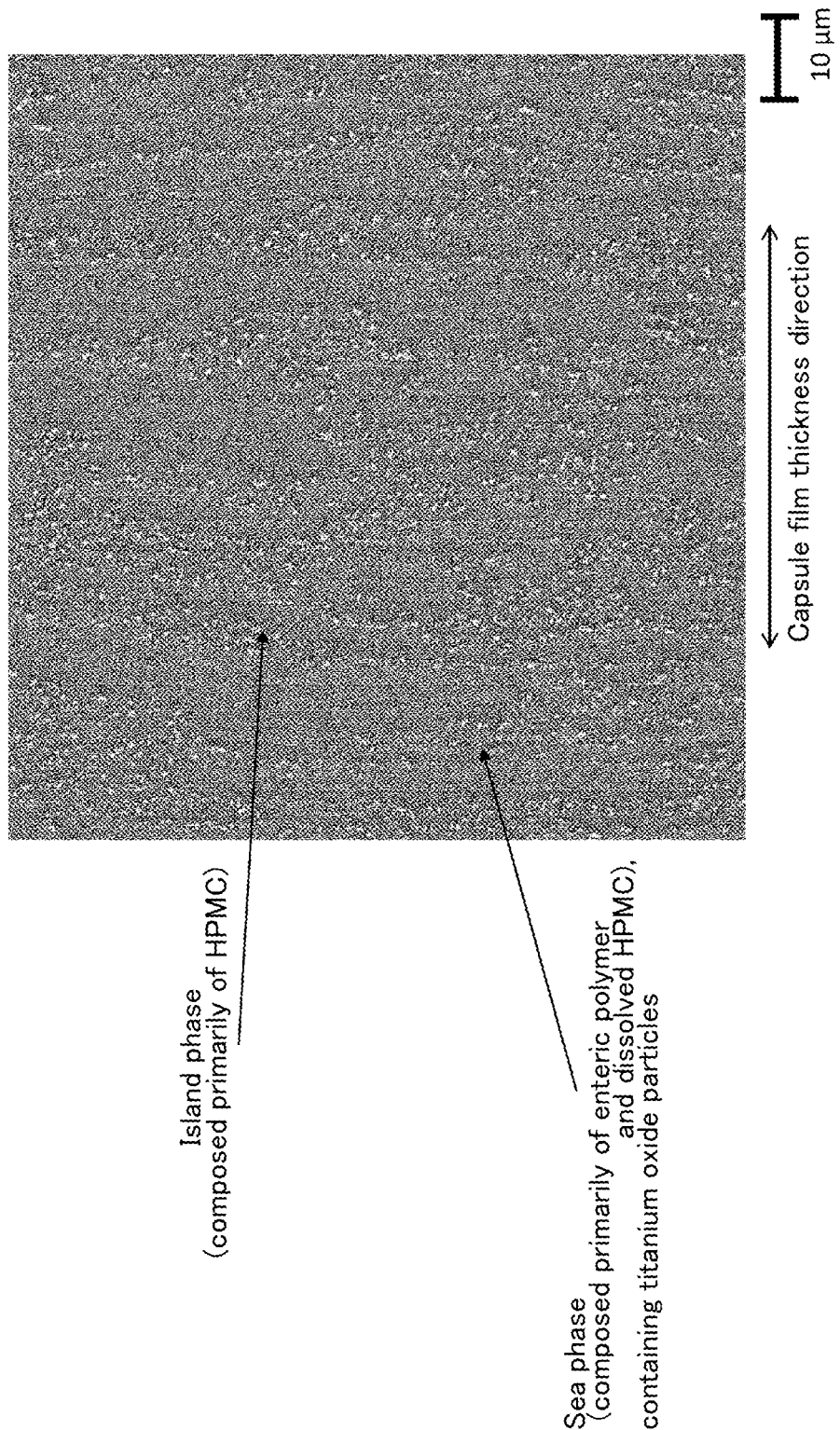
FIG. 2 is a diagram showing a scanning electron microscope image of a transverse cross-section of a capsule film of Example 2-2.

Next, when a piece was cut out from a transverse cross-section of the capsule film of Example 1-3 and observed under the scanning electron microscope, a structure consisting of elongated island phases and a sea phase as shown in FIG. 2 was observed. When the components of each phase were analyzed by microscopic Raman analysis, it was found that the phase in which dark particles are present in the diagram is the sea phase, and the dark particles were aggregates of titanium oxide dispersed in the sea phase. It is presumed that the particles were too coarse or aggregated to enter the island portions of the undissolved HPMC. The composition of the residual sodium in the capsule film measured with an atomic absorption spectrometer was almost the same in amount as the NaOH concentration in a jerry solution. From this, it was presumed that almost the entire amount of NaOH formed a salt (—COONa) and was incorporated in the film. The capsule was stored in a dry oven at 60° C. for three days, no change such as yellowing was observed. Also, there was almost no change in the results of the dissolution test. It is believed that no adverse effect of the salt on the film was observed because the amount of partially neutralized enteric methacrylic acid copolymer in the entire enteric polymer was as sufficiently small as about 8%.

In addition, observation of the microstructure of an enteric capsule performed on a film sample to which titanium oxide had not been added in Example 1-3 by imaging Raman spectroscopy revealed the separation between a region in which almost only a peak inherent to the HPMC was detected and a region in which peaks of both the HPMC and L30D-55 were simultaneously detected. In other words, two types of phases, that is, phases composed primarily of the HPMC (island phases) and a phase in which the HPMC and L30D55 were mixed (sea phase), were observed. The presumption that solid fine particles of undissolved HPMC remain to form islands and HPMC and L30D-55 partially dissolved into the water solvent form a sea phase surrounding each island in the capsule preparation liquid of the present invention is confirmed. It is presumed that because the degree of neutralization is about 8%, most of L30D-55 is contained as colloidal particles. It is also presumed that the peak intensity ratio between HPMC (1370 cm$^{-1}$ ($\delta$CH3)) and L30D-55 (1730 cm$^{-1}$ ($\nu$C=O)) in the sea phase is about 32.5 versus 62.5, and therefore L30D-55 is the primary component and the sea phase ensures the enteric function.

Further, it is presumed that the coexistence of HPMC dissolved in the sea phase and the enteric polymer contributes to enhancing the adhesion between the island phases (undissolved HPMC particles) to enhance the mechanical strength of the capsule film as a whole.

Figure 3:
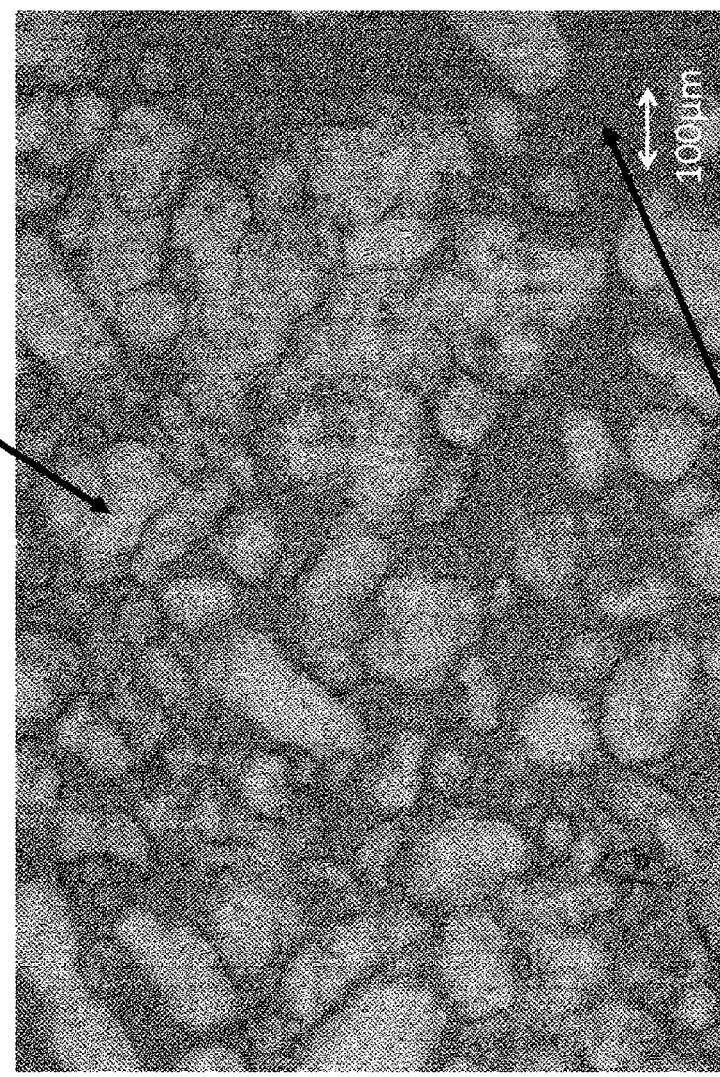
FIG. 3 is a diagram showing an optical microscope image of a capsule preparation liquid (55° C.) of Example 2-2.

Next, the preparation liquid used in Example 1-3 was dropped onto a slide glass on the stage kept at a temperature of 55° C. and further sealed with a cover glass preheated to 55° C. A transmission image of the preparation liquid obtained by an optical microscope is shown in FIG. 3. The whitish parts in the image are solid fine particles of undissolved HPMC. The surrounding dark region is an aqueous solution composed primarily of the enteric polymer, which contains titanium oxide and therefore looks dark. In addition, observation was performed with the above-mentioned preparation liquid sandwiched between the cover glass and the slide glass held on the microscope stage while the temperature was decreased at a rate of 10° C./min. Then, almost all fine particles of undissolved HPMC remained until the temperature reached room temperature although the fine particles showed changes in particle size and particle shape due to swelling probably caused by permeation of water. On the other hand, in a fluid dispersion of HPMC particles (component i), undissolved particles disappeared and the entire amount of undissolved particles was dissolved when the temperature fell below about 30° C. In the process of preparing a hard capsule, the moisture in the dispersed fine particles, which have been swollen as described above, evaporates during the drying step and the fine particles are compressed in the film thickness direction until the diameter thereof in the thickness direction is sufficiently smaller than the thickness of the capsule film (about 100 μm). As can be seen from the cross-sectional view of the film in FIG. 2, the diameter in the thickness direction has reduced to about 30 μm or less.

When the capsule preparation liquid was stored in a stirring container at 55° C., this fluid dispersion of HPMC solid fine particles was confirmed to be stable for at least more than one week. During this period, the viscosity was also stable except for initial fluctuations.

Figure 4:
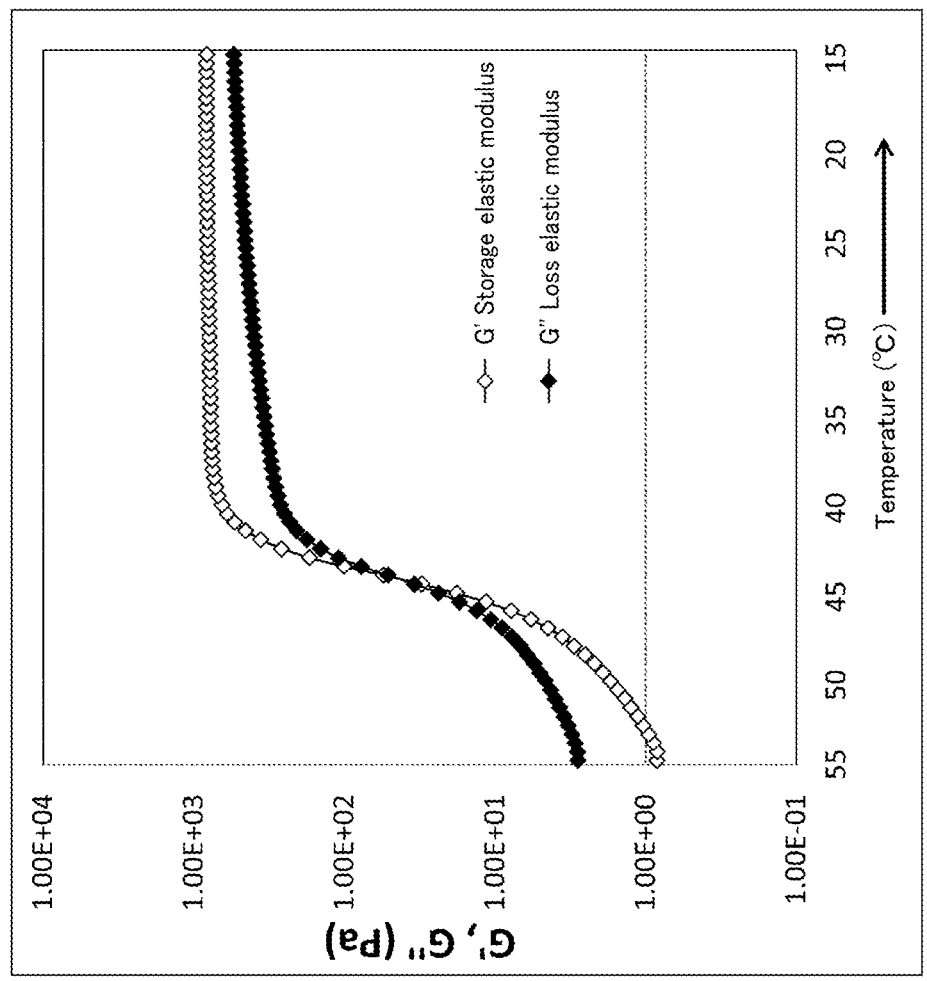
FIG. 4 is a diagram showing a dynamic viscoelasticity behavior of a capsule preparation liquid of Example 2-2 during a temperature decrease. For example, 1.00 E+2 on the vertical axis indicates 100, and 1.00 E+3 (訳注：上と同様) indicates 1000.

In addition, FIG. 4 shows changes in storage elastic modulus G'(Pa) and loss elastic modulus G"(Pa) observed when the temperature of the preparation liquid used in Example 1-3 was decreased from the temperature T1 to room temperature. The storage elastic modulus G'(Pa)

exceeded the loss elastic modulus G"(Pa) between 40° C. and 45° C., and remained higher than the loss elastic modulus G"(Pa) until the temperature reached about room temperature. This demonstrated that the preparation liquid is suitable for preparation of a hard capsule by a cold gelation method.

TABLE 4

| | Description | Component i HPMC or MC | Component i α (%) | Component ii Methacrylic acid copolymer | Component ii β (%) | Component iii Substance name | Component iii γ (%) | Basic neutralizing agent Substance name | Basic neutralizing agent ε (%) | Degree of neutralization (%) For component ii | Polymer component concentration (%) | Gelation at around room temperature (G' > G") | Abrupt increase in viscosity at 30 to 50° C. | Self-supporting dry film formation |
|---|---|---|---|---|---|---|---|---|---|---|---|---|---|---|
| Ref. Ex. 1-1 | Component i fluid dispersion | TC-5S | 58.5 | Water substitution | 41.5 | Nil | 0.0 | NaOH | 0.00 | 0.0 | | x | x | ○ |
| Ref. Ex. 1-2 | Component ii fluid dispersion | Water substitution | 58.5 | L30D55 | 41.5 | Nil | 0.0 | NaOH | 0.00 | 0.0 | | x | x | x |
| Ref. Ex. 1-3 | Component i + component ii fluid dispersion (without neutralizing agent) | TC-5S | 58.5 | Water substitution | 41.5 | Nil | 0.0 | NaOH | 0.00 | 0.0 | Aggregated immediately after mixing | Aggregated immediately after mixing | ○ |
| Ref. Ex. 1-4 | Component i + component ii fluid dispersion (partial neutralization) (titanium oxide is excluded in Example 1-3) | TC-5S | 58.5 | L30D55 | 41.5 | Nil | 0.0 | NaOH | 0.70 | 7.9 | 14.5 | ○ | ○ | ○ |
| Ref. Ex. 1-5 | Component i + component ii neutralized solution (complete neutralization) | TC-5S | 58.5 | L30D55 | 41.5 | Nil | 0.0 | NaOH | 8.95 | 100.4 | 14.5 | x | x | x |
| Ref. Ex 2-1 | Complete i fluid dispersion | 60SH-50 | 37.7 | Water substitution | 41.5 | Water substitution | 20.8 | NaOH | 0.00 | 0.0 | | x | ○ | ○ |
| Ref. Ex 2-2 | Component i fluid dispersion + component iii fluid dispersion | Water substitution | 37.7 | L30D55 | 41.5 | NE30D | 20.8 | NaOH | 0.00 | 0.0 | | x | x | x |
| Ref. Ex 2-3 | Component i + component ii fluid dispersion (without neutralizing agent) + component iii | 60SH-50 | 37.7 | L30D-55 | 41.5 | NE30D | 20.8 | NaOH | 0.00 | 0.0 | Aggregated immediately after mixing | Aggregated immediately after mixing | ○ |
| Ref. Ex 2-4 | Component i + component ii fluid dispersion (partial neutralization) + component iii (titanium oxide is excluded in Example 1-5) | 60SH-50 | 37.7 | L30D-55 | 41.5 | NE30D | 20.8 | NaOH | 0.70 | 7.8 | | ○ | ○ | ○ |
| Ref. Ex 2-5 | Component i + component ii fluid dispersion (complete neutralization) + component iii | 60SH-50 | 37.7 | L30D-55 | 41.5 | NE30D | 20.8 | NaOH | 8.92 | 100.0 | | x | x | x |

TABLE 4-continued

| | Description | Component i HPMC or MC | α (%) | Component ii Methacrylic acid copolymer | β (%) | Component iii Substance name | γ (%) | Basic neutralizing agent Substance name | ε (%) | Degree of neutralization (%) For component ii | Polymer component concentration (%) | Gelation at around room temperature (G' > G") | Abrupt increase in viscosity at 30 to 50° C. | Self-supporting dry film formation |
|---|---|---|---|---|---|---|---|---|---|---|---|---|---|---|
| Ref. Ex 3-1 | Component i + component ii fluid dispersion (partial neutralization) + component iii | TC-5S | 47.7 | L30D55 | 41.8 | NE30D | 10.5 | NaOH | 0.18 | 2.0 | 14.4 | Slightly aggregated | | ○ |
| Ref. Ex 3-2 | Component i + component ii fluid dispersion (partial neutralization) + component iii | TC-5S | 47.7 | L30D55 | 41.8 | NE30D | 10.5 | NaOH | 0.36 | 4.0 | 14.4 | ○ | ○ | ○ |
| Ref. Ex 3-3 | Component i + component ii fluid dispersion (partial neutralization) + component iii | TC-5S | 47.7 | L30D55 | 41.8 | NE30D | 10.5 | NaOH | 1.08 | 12.0 | 14.4 | ○ | ○ | ○ |
| Ref. Ex 3-4 | Component i + component ii fluid dispersion (partial neutralization) + component iii | TC-5S | 47.7 | L30D55 | 41.8 | NE30D | 10.5 | NaOH | 1.40 | 15.6 | 14.4 | ○ | ○ | ○ |
| Ref. Ex 3-5 | Component i + component ii fluid dispersion (partial neutralization) + component iii | TC-5S | 47.7 | L30D55 | 41.8 | NE30D | 10.5 | NaOH | 1.80 | 20.0 | 14.4 | x | ○ | ○ |

2. Reference Examples 1, 2 and 3

In order to confirm that the component i, the component ii, and an appropriate amount of a basic neutralizing agent are all necessary for the preparation liquid for a cold pin dipping method and the hard capsule of the present invention, various solutions were prepared, and their suitability as a capsule preparation liquid was determined. Reference Examples 1-1 to 1-5, and Reference Examples 2-1 to 2-5 were based on the same composition as that of Example 1-3 and Example 1-5, respectively, except that no titanium oxide was added, and any of the components was omitted and simply replaced with the same mass of purified water in the preparation method of the aspect 3-1.

Table 4 shows the compositions of the preparation liquids (no titanium oxide is contained in each case), the results of dynamic viscoelasticity measurement with a rheometer during a temperature decrease, that is, the presence or absence of gelation at about room temperature (if G'>G" in the rheometer measurement, gelation is determined to have occurred and indicated by "o." The case where G'<G" or G'>G" but G' is so small that the solidification is virtually impossible is indicated by "x."), and the presence or absence of an abrupt increase in viscosity at 30 to 50° C. Also, it was evaluated whether a self-supporting film can be obtained by a casting method as "Self-supporting dry film formation." This evaluation shows whether a self-supporting can be formed without any other support material, and whether the empty hard capsule film has appropriate mechanical strength. In Table 4, the case where a self-supporting film was able to be formed is indicated by o. The case where the film was too fragile or soft as a self-supporting film to peel from a substrate to which the preparation liquid had been applied even when the polymer component concentration was adjusted to some extent in a casting method was indicated by x.

The dynamic viscoelasticity behavior during a temperature decrease was compared between the capsule preparation liquid of the present invention, which contained both of a combination of HPMC (TC-5S, 60SH-50) as the component i with a fluid dispersion of Eudragit L30D-55 as the component ii and a basic neutralizing agent necessary for appropriate partial neutralization (Reference Examples 1-4 and 2-4), and solutions which lacked in any of the components (Reference Examples 1-1 to 1-3 and 2-1 to 2-3). The omitted component was simply replaced with the same mass of purified water.

Fluid dispersions in which the component i was partially dissolved (Reference Examples 1-1 and 2-1) exhibited an increase in viscosity presumed to be due to structural viscosity at 30 to 50° C. but did not exhibit gelation (G'>G") at about room temperature. A fluid dispersion of the component ii alone (Reference Example 2-2) exhibited a liquid-like behavior almost completely over the entire temperature range, and its G' and G" were both very low and about less than 100 mPa·s from 55° C. to room temperature. In other words, it exhibited neither an appropriate increase in viscosity in the temperature decreasing process nor a cold gelation ability at around room temperature. Further, a liquid mixture of the component ii and the component iii (Reference Example 2-2) also showed neither an appropriate increase in viscosity in the temperature decreasing process nor a cold gelation ability.

A capsule preparation liquid containing only the component i and a fluid dispersion of the component ii free of a basic neutralizing agent (without neutralizing agent) (Reference Example 1-3) was inadequate as a capsule preparation liquid because significant aggregation occurred immediately after both the components were mixed. This phenomenon was hardly affected by the presence of the component iii or the component iv. When the component i, the component ii and the component iii were contained but the component ii was completely neutralized with a neutralizing agent (Reference Examples 1-5 and 2-5), a slight increase in viscosity was observed during a temperature decrease but the viscosity was very low (about 100 mPa·s or less) as a whole and preferred cold gelation properties were lost. Only when the component i and the component ii with a degree of neutralization of about 8% were mixed (Reference Examples 1-4 and 2-4), an appropriate cold gelation property was obtained. From those facts, it is believed to be important that a capsule preparation liquid for preparing an enteric hard capsule contains all of the component i, the component ii and a basic neutralizing agent capable of partially neutralize the component ii.

In addition, examples in which the degree of neutralization for L30D-55 with NaOH were varied are shown in Reference Examples 3-1 to 3-5. When the degree of neutralization was 2%, a small amount of aggregates started to appear. When the degree of neutralization was 20%, G' once exceeded G" in the temperature decreasing process, indicating that gelation occurred. However, a tendency was observed in which the curves finally crossed again at around room temperature, in particular at 25° C. or less, and G' fell below G". Capsule molding was still possible but the cold gelation properties were impaired. When the degree of neutralization is higher than this, liquid dripping made capsule molding difficult. It was confirmed that an adequate degree of neutralization is required for cold gelation.

When FS30D was used as the component ii, aggregation immediately occurred by a similar phenomenon when it was mixed with the component i if the degree of neutralization was less than 2%.

Naturally, the enteric properties of the film after drying cannot be ensured without the presence of the component ii as an enteric base. With the component ii itself, or with the component ii and the component iii alone, the resulting film was too fragile and formation of a self-supporting film was difficult. In the present invention, in particular, the rate of the component i among the film components can be increased 20% by mass or more, preferably 30% by mass or more, still more preferably 40% by mass or more, and a self-supporting film can be achieved only with the component i and the component ii (and a small amount of a basic neutralizing agent).

3. Example 2

A capsule formulation was provided by filling an acetaminophen mixed powder in an enteric hard capsule of Example 1-3 according to the present disclosure (No. 3 size) and used as an inner capsule. A capsule formulation having a double capsule structure was provided by filling 100 mg of caffeine and the above-mentioned inner capsule into a hypromellose capsule (Quali-V (trademark), No. 0 size). After a two-hour dissolution test in the first liquid with a pH of 1.2, the capsule was taken out and subsequently subjected to a dissolution test in the second liquid with a pH of 6.8. The changes in dissolution rate of the caffeine and acetaminophen over time are shown in FIG. 6. In the first liquid, only the hypromellose capsule, which has no pH dependence, was quickly dissolved and almost 100% of the caffeine contained therein alone was dissolved out within a short period of time. However, the enteric hard capsule according to the present disclosure inside was not dissolved and less than 10% of acetaminophen was dissolved out. It was shown that the acetaminophen started to be dissolved out quickly after the capsule was transferred into the second liquid, and 100% of the acetaminophen was dissolved out within about 30 minutes.

4. Reference Example 4

In Reference Example 4-1, a cloudy opaque capsule preparation liquid with fine particles of HPMC dispersed therein was fabricated from the composition as shown in Table 5 through the same preparation process as that in Example 1, and kept warm at 55° C. On the other hand, in Reference Example 4-2, a transparent aqueous solution was prepared by first adding only an HPMC ingredient powder to warm water at about 80° C., and decreasing the temperature to room temperature to dissolve the HPMC particles almost completely. Then, a partially neutralized solution was fabricated by adding sodium hydroxide to a slightly clouded colloidal dispersion of L50D-55 at room temperature, and mixed with the HPMC aqueous solution. A fluid dispersion of titanium oxide was added last, and the mixture was kept at room temperature. The preparation liquid of Reference Example 4-2 has no cold gelation function on its own. Using the preparation liquids of Reference Examples 4-1 and 4-2 held at 55° C. and room temperature, respectively, films were fabricated by a casting method.

microscopic observation of the preparation liquids of Reference Examples 4-1 and 4-2 held at 55° C. and room temperature, respectively. In other words, in the preparation liquid of Reference Example 4-1, undissolved HPMC particles that will become core particles after drying and a solution part that will become a binding phase after drying are observed. On the other hand, in the preparation liquid of Reference Example 4-2, an optically uniform solution is observed.

It is believed that when HPMC core particles are once dissolved completely without any residue, the HPMC molecules and the enteric polymer are uniformly mixed (even if colloidal particle structure of several nm may remain to some extent) and phase structures on the order of µm or more disappear. In this case, with a functional (enteric) polymer content of about 40% by mass, sufficient functionality (acid resistance) cannot be ensured. In order to ensure the functionality, a functional polymer must be a primary component, that is, it is necessary to add about 60% by mass or more of a functional polymer (L30D-55), in which case the resulting film is very brittle and film strength suitable as a hard capsule is difficult to obtain.

On the other hand, it was found that, by binding core particles of water-soluble HPMC with a phase primarily composed of an enteric polymer, the core particles are covered with a phase primarily composed of an enteric polymer almost completely, and a desired (acid resistance)

TABLE 5

| | | Component i | | Component ii Methacrylic acid copolymer | | Component iii | | Basic neutralizing agent | | Degree of neutralization (%) | Polymer component concen- | Others | |
|---|---|---|---|---|---|---|---|---|---|---|---|---|---|
| | Description | HPMC | α (%) | | β (%) | Substance name | γ (%) | Substance name | ε (%) | For component ii | tration (%) | Substance name | σ (%) |
| Ref. Ex. 4-1 | HPMC partially dissolved | TC-5S | 58.3 | L30D55 | 41.7 | NE30D | 0.0 | NaOH | 0.72 | 8.0 | 16.9 | Titanium oxide | 3.1 |
| Ref. Ex. 4-2 | HPMC completely dissolved | TC-5S | 58.3 | L30D55 | 41.7 | NE30D | 0.0 | NaOH | 0.72 | 8.0 | 13.9 | Titanium oxide | 3.1 |

Figure 7A:
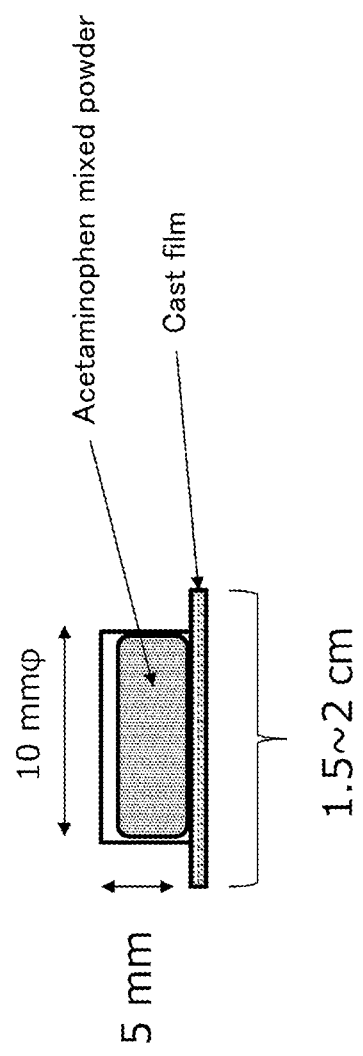
FIG. 7(a) is a diagram showing a cross-sectional structure of a test sample used in a film dissolution test in Reference Example 4.
Figure 7B:
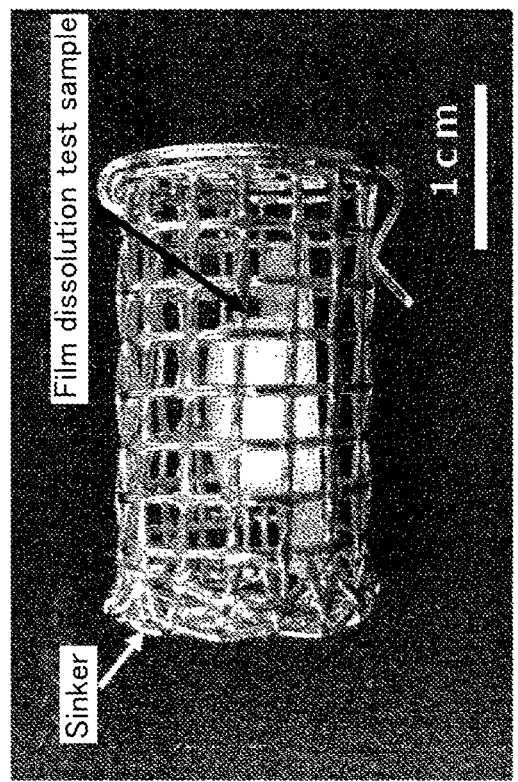
FIG. 7(b) is a photograph showing the state of the test sample enclosed in a sinker.
Figure 8B:
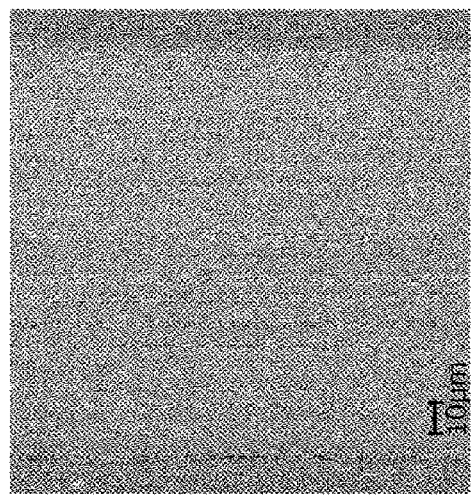
FIG. 8(b) is a cross-sectional view of a film of Reference Example 4-2.
Figure 8A:
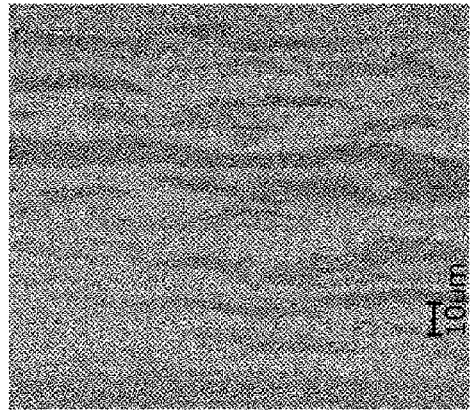
FIG. 8(a) is a cross-sectional view of a film of Reference Example 4-1.

As shown in the cross-sectional view of FIG. 7(a), a test sample was provided by bonding the above-mentioned film to an opening of a blister pack container (made of polyvinyl chloride, height about 5 mm, opening diameter 10 mmφ) with 198.45 mg of an acetaminophen mixed power for use in a dissolution test contained therein. Then, as shown in FIG. 7(b), the test sample was enclosed in a sinker, and a dissolution test was conducted in a dissolution test liquid (37° C.) with a pH=1.2 (hereinafter referred to as film dissolution test).

The dissolution rates after the elapse of two hours were 3.5% and 11.5% for Reference Examples 4-1 and 4-2, respectively.

When SEM observation was performed on a cross-section of the films formulated as in Reference Examples 4-1 and 4-2 without titanium oxide, the film of Reference Example 4-1 had a two-phase structure having core phases of undissolved HPMC particles according to the present invention. On the other hand, in the film of Reference Example 4-2, such a multiphase structure was not formed because HPMC had been once dissolved completely. It was found that all the components were dissolved almost uniformly and dried into a film without any change. This can be also confirmed by function can be imparted with a smaller amount of a functional (enteric) copolymer.

The invention claimed is:
1. An enteric hard capsule comprising a film
   (a) containing a first component and a second component, or
   (b) containing a first component and a second component, and further containing at least one component selected from a third component and a fourth component,
   wherein the first component is at least one water-soluble cellulose compound selected from the group consisting of methylcellulose and hydroxypropyl methylcellulose and has a viscosity value of 6 mPa·s or more and less than 100 mPa·s, wherein the viscosity value is obtained by measuring a viscosity value of a 2 mass % aqueous solution of the water-soluble cellulose compound at 20° C.±0.1° C. using an Ubbelohde method,
   the second component is an enteric methacrylic acid copolymer and at least some of carboxyl groups contained in the second component form a salt thereof that is acceptable pharmaceutically or as a food additive,
   the third component is a water-insoluble alkyl (meth) acrylate ester copolymer and/or ethyl cellulose, and the fourth component is at least one selected from the group consisting of a plasticizer and a surfactant acceptable pharmaceutically or as a food additive, wherein the first component is contained at a rate of 30 to 70% by mass and the second component is contained at a rate of 30 to 60% by mass with the sum of the rates of the first component and the second component being 70% by mass or more based on the total mass of the first component, the second component, the third component and the fourth component contained in the film, which is taken as 100% by mass, and wherein the enteric hard capsule is prepared by a cold gelation method comprising:

dipping a mold pin into an enteric hard capsule preparation liquid comprising the first component, the second component, a basic neutralizing agent acceptable pharmaceutically or as a food additive, and a solvent, wherein the mold pin has a surface temperature lower than a temperature of the enteric hard capsule preparation liquid; and pulling up the mold pin from the enteric hard capsule preparation liquid and drying the enteric hard capsule preparation liquid adhering to an outer surface of the mold pin.

2. The enteric hard capsule according to claim 1, wherein the first component has a viscosity value of 10 mPa·s or more.

3. The enteric hard capsule according to claim 1, wherein the first component is hydroxypropyl methylcellulose of substitution degree type 2910 or substitution degree type 2906.

4. The enteric hard capsule according to claim 1, wherein the enteric methacrylic acid copolymer of the second component is a copolymer composed of 40 to 60% by mass of methacrylic acid and 60 to 40% by mass of ethyl acrylate.

5. The enteric hard capsule according to claim 1, wherein the film has a moisture content of 2 to 10% by mass.

6. The enteric hard capsule according to claim 1, wherein the third component is contained at a rate of 0 to 30% by mass based on the total mass of the first component, the second component, the third component and the fourth component contained in the film, which is taken as 100% by mass.

7. The enteric hard capsule according to claim 1, wherein the fourth component is contained at a rate of 0 to 12% by mass based on the total mass of the first component, the second component, the third component and the fourth component contained in the film, which is taken as 100% by mass.

8. The enteric hard capsule according to claim 1, wherein the carboxyl groups forming a salt is contained at a rate of 2 to 20 mol % based on the total number of moles of the carboxyl groups forming a salt and carboxyl groups not forming a salt in the second component contained in the film, which is taken as 100 mol %.

9. The enteric hard capsule according to claim 1, wherein the salt is a sodium salt.

10. The enteric hard capsule according to claim 1, wherein the film has a thickness of 50 to 250 μm.

11. The enteric hard capsule according to claim 1, wherein the film has an elastic modulus of 1 GPa to 5 GPa after humidity conditioning at a relative humidity of 63% at 25° C., and the elastic modulus is measured by preparing a sample film having a dumbbell shape of 5 mm×75 mm and a thickness of 100 μm and subjecting the sample film to humidity conditioning for one week or longer under humidity conditioning conditions at 25° C. and a relative humidity of 63% using potassium acetate saturated salt; setting both ends of the sample film on a holder with a gap length of 60 mm; performing a tensile test by pulling the sample film at a tensile rate of 10 mm/min thereby obtaining an elongation of the sample film and a curve between a stress that occurs in the sample film and an elongation rate; and determining the elastic modulus from an inclination of the curve in an elastic deformation region at a time of a low stress under an environment with a temperature of 25° C. and a relative humidity of 63%.

12. The enteric hard capsule according to claim 1, wherein the film has a rate of elongation at break of 2% to 30% after humidity conditioning at a relative humidity of 22% at 25° C., and the elongation at break is obtained by preparing a sample film having a dumbbell shape of 5 mm×75 mm and a thickness of 100 μm and subjecting the sample film to humidity conditioning for one week or longer under humidity conditioning conditions at 25° C. and a relative humidity of 22% using potassium acetate saturated salt; setting both ends of the sample film on a holder with a gap length of 60 mm; and performing a tensile test by pulling the sample film at a tensile rate of 10 mm/min thereby obtaining an elongation rate at a breakpoint as the elongation at break, under an environment with a temperature of 25° C. and a relative humidity of 22%.

13. The enteric hard capsule according to claim 1, wherein the film of the enteric hard capsule has a multiphase structure separated into a phase composed of the first component and a mixed phase of the first component and the second component.

14. The enteric hard capsule according to claim 13, wherein the mixed phase further contains the third and fourth components.

15. The enteric hard capsule according to claim 14, wherein the phase containing the first component has a minor axis with a length of 0.1 μm or more and less than 30 μm.

16. The enteric hard capsule according to claim 1, wherein the enteric hard capsule has a dissolution rate of 10% or less after the elapse of two hours in a dissolution test using a solution having a pH of 1.2.

17. The enteric hard capsule according to claim 16, wherein the enteric hard capsule has a dissolution rate of 75% or more after the elapse of 45 minutes in a dissolution test using a solution having a pH of 6.8.

18. The enteric hard capsule according to claim 17, wherein the enteric hard capsule takes 60 minutes or more before reaching a dissolution rate of 75% or more in a dissolution test using a solution having a pH of 6.8.

19. The enteric hard capsule according to claim 18, wherein the enteric hard capsule has a dissolution rate of 30% or less after the elapse of two hours in a dissolution test using a solution having a pH of 4.0.

20. An enteric hard capsule formulation, comprising the enteric hard capsule according to claim 1 sealed with a sealing liquid, wherein the sealing liquid comprises 10 to 50% by mass of the enteric methacrylic acid copolymer used for the film of the enteric hard capsule, 0.0 to 0.6% by mass of NaOH as a basic neutralizing agent, 0.5 to 40% by mass of triethyl citrate, and a water/ethanol mixed solvent as the balance.

21. An enteric hard capsule formulation, comprising the enteric hard capsule according to claim 1 sealed with a sealing liquid, wherein the sealing liquid comprises 10 to 40% by mass of hydroxypropyl methylcellulose acetate succinate, and ethanol as the balance.

22. A hard capsule formulation, comprising the enteric hard capsule according to claim 1 filled with an active drug, wherein the hard capsule formulation has a dissolution rate of the active drug of 10% or less after the elapse of two hours in a dissolution test using a solution having a pH of 1.2.

23. A hard capsule formulation, comprising the enteric hard capsule according to claim 1 filled with an active drug, wherein the hard capsule formulation has a dissolution rate of the active drug of 10% or less after the elapse of two hours in a dissolution test using a solution having a pH of 1.2, and a dissolution rate of the active drug of 75% or more after the elapse of 45 minutes in a dissolution test using a solution having a pH of 6.8.

24. A hard capsule formulation, comprising the enteric hard capsule according to claim 1 filled with an active drug, wherein the hard capsule formulation has a dissolution rate of the active drug of 10% or less after the elapse of two hours in a dissolution test using a solution having a pH of 1.2, and takes 60 minutes or more before having a dissolution rate of the active drug of 75% or more in a dissolution test using a solution having a pH of 6.8.

25. A hard capsule formulation, comprising the enteric hard capsule according to claim 1 filled with an active drug, wherein the hard capsule formulation has a dissolution rate of the active drug of 10% or less after the elapse of two hours in a dissolution test using a solution having a pH of 1.2, a dissolution rate of the active drug of 75% or more after the elapse of 45 minutes in a dissolution test using a solution having a pH of 6.8, and a dissolution rate of the active drug of 30% or less after the elapse of two hours in a dissolution test using a solution having a pH of 4.0.

26. A double hard capsule formulation, comprising the enteric hard capsule according to claim 1 within a hard capsule dissolvable under an acidic condition.

\* \* \* \* \*